US007115597B2

(12) United States Patent
Bilodeau et al.

(10) Patent No.: US 7,115,597 B2
(45) Date of Patent: Oct. 3, 2006

(54) TYROSINE KINASE INHIBITORS

(75) Inventors: Mark T. Bilodeau, Lansdale, PA (US); George D. Hartman, Lansdale, PA (US); Jacob M. Hoffman, Jr., Lansdale, PA (US); John T. Sisko, Lansdale, PA (US); Peter J. Manley, Harleysville, PA (US); Anthony M. Smith, Green Lane, PA (US); Thomas J. Tucker, North Wales, PA (US); William C. Lumma, Jr., Helena, MT (US); Leonard Rodman, New York, NY (US)

(73) Assignee: Merck & Co., Inc., Rahway, NJ (US)

( * ) Notice: Subject to any disclaimer, the term of this patent is extended or adjusted under 35 U.S.C. 154(b) by 215 days.

(21) Appl. No.: 10/677,687

(22) Filed: Oct. 2, 2003

(65) Prior Publication Data

US 2004/0063720 A1  Apr. 1, 2004

Related U.S. Application Data

(63) Continuation of application No. 09/990,473, filed on Nov. 21, 2001, now abandoned.

(60) Provisional application No. 60/251,006, filed on Dec. 4, 2000.

(51) Int. Cl.
*C07D 417/12* (2006.01)
*A61K 31/427* (2006.01)
*C07D 241/04* (2006.01)

(52) U.S. Cl. ............... 514/217.06; 514/218; 514/227.8; 514/235.8; 514/249; 514/252.19; 514/256; 540/492; 540/575; 540/601; 544/60; 544/121; 544/122; 544/328

(58) Field of Classification Search ................ 540/492, 540/575, 601; 544/60, 121, 122, 328; 514/217.06, 514/218, 227.8, 235.8, 249, 252.19, 256
See application file for complete search history.

(56) References Cited

FOREIGN PATENT DOCUMENTS

| EP | 1040831 A2 | 4/2000 |
|---|---|---|
| WO | WO 95/33750 | 12/1995 |
| WO | WO 99/65884 | 6/1999 |
| WO | WO 00/39101 | 7/2000 |
| WO | WO 00/62778 | 10/2000 |

OTHER PUBLICATIONS

Roodhooft, PubMed Abstract (Bull Soc Belge Ophthalmol. 276:83-92), 2000.*
J. Rak et al. Cancer Research, 55:4575-4580, 1995.
G. Gasparini and A.L. Harris, J. Clin. Oncol., 1995, 13:765-782.
M. Toi et al., Japan. J. Cancer Res., 1994, 85:1045-1049.
A.J. Dickinson et al., Br. J. Urol., 1994, 74:762-766.
L.M. Ellis et al., Surgery, 1996, 120(5):871-878.
J.K. Williams et al., Am. J. Surg., 1994, 168:373-380.
A. Amirkhosravi et al., Platelets, 10:285-292 (1999).
S.P. Gunningham, et al., Can. Research, 61:3206-3211 (2001).
A. Giatromanolaki et al., J. Pathol. 2001; 194:101-108.
Michael Detmar, J. Dermatological Sci., 24 Suppl. 1, S78-S84 (2000).
Hasegawa et al., Skeletal Radiol., vol. 28, pp. 41-45, 1999.
Brockelsby et al., Laboratory Investigation 79:1101-1111 (Sep. 1999).
Paul et al., Nature Med 7:222-227 (2001).
Matsuyama et al., J. Neurol. Sci. 186:75-79 (2001).
van der Flier et al., J. Infectious Diseases, 183:149-153 (2001).
Stephen K. Smith, Trends in Endocrinology & Metabolism, vol. 12, No. 4, pp. 147-151, May/Jun. 2001.
Levis et al., Blood, vol. 98, No. 3, pp. 885-887 (2001).
Rajesh K. Jain, Nature Medicine, vol. 7. No. 9, pp. 987-989 (Sep. 2001).
Giulio Jori, Lasers Med. Sci., 1990; 5: 115-120.
Chuannong Zhou, J. Photochem. and Photobiol. 1989; 3: 299-318.
Hendrich et al., Knee Surg Sports Traumatol Arthroscopy 5: 58-63 (1997).
Hall et al., Am J Hum Genet 61:785-789, 1997.
Li et al., Gene Therapy, 1998; 5:1105-13.
Fathallah-Shaykh et al., J Immunol 2000; 164:217-222.
Dougherty et al., J. Natl. Cancer Inst., 1998, 90(12): 889-905.
Van Bruggen et al., J. Clin. Invest,. 104:1613-1620 (1999).
Gerber et al., Nature Medicine, vol. 5, No. 6, pp. 623-628, 1999.
David A. Greenberg, Drug News Perspect 11(5):265-270 (1998).
Nakagawa et al., FEBS Let. 473:161-164 (2000).
Peter Traxler, Exp. Opin. Ther. Patents 8 (12) 1599-1625(1998).
Peter M. Traxler, Exp. Opin. Ther. Patents 7(6) 571-588 (1997).
Joseph V. Simone, Cecil Textbook of Medicine 20th Edition, vol. 1, pp. 1004-1010 (1996).

* cited by examiner

*Primary Examiner*—Deepak Rao
(74) *Attorney, Agent, or Firm*—Dianne Brown; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

31 Claims, No Drawings

TYROSINE KINASE INHIBITORS

DOMESTIC PRIORITY CLAIM

This continuation claims priority to application Ser. No. 09/990,473, filed on Nov. 21, 2001, now abandoned, which claims the priority of U.S. Provisional Application No. 60/251,006, filed on Dec. 4, 2000.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

Tyrosine kinases are a class of enzymes that catalyze the transfer of the terminal phosphate of adenosine triphosphate to tyrosine residues in protein substrates. Tyrosine kinases play critical roles in signal transduction for a number of cell functions via substrate phosphorylation. Though the exact mechanism of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene*, 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol.* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993). VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D'Amore, *Cytokine & Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti- VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Accordingly, the identification of small compounds which specifically inhibit, regulate and/or modulate the signal transduction of tyrosine kinases is desirable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

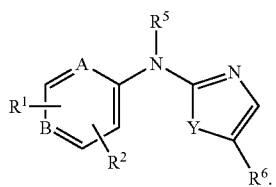

I

DETAILED DESCRIPTION OF THE INVENTION

The compounds of this invention are useful in the inhibition of kinases and are illustrated by a compound of Formula I:

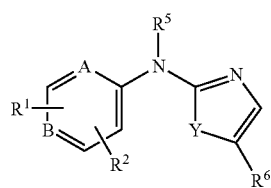

I or a pharmaceutically acceptable salt or stereoisomer thereof, wherein
A and B are independently N or $N^+$—$O^-$;
Y is O, S or N—$R^4$;
$R^1$ and $R^2$ are independently:
 1) H,
 2) $O_r(C_1$–$C_6)$perfluoroalkyl,
 3) OH,
 4) CN,
 5) halogen,
 6) (C=O)$_r$O$_s$(C$_1$–C$_{10}$)alkyl,
 7) (C=O)$_r$O$_s$(C$_2$–C$_{10}$)alkenyl,
 8) (C=O)$_r$O$_s$(C$_2$–C$_{10}$)alkynyl,
 9) (C=O)$_r$O$_s$aryl,
 10) (C=O)$_r$O$_s$heterocyclyl,
 11) (C$_0$–C$_6$)alkyl-NR$^a$R$^b$, or
 12) (C$_1$–C$_6$)heterocyclyl,
  wherein r and s are independently 0 or 1, and said alkyl, alkenyl, alkynyl, aryl, and heterocyclyl is optionally substituted with one or more substituents selected from $R^7$;
$R^4$ is H, aryl or (C$_1$–C$_6$)alkyl;
$R^5$ is:
 1) H,
 2) SO$_2$R$^c$,
 3) (C=O)$_r$R$^c$, wherein r is 0 or 1, or
 4) CO$_2$R$^c$;
$R^6$ is:
 1) aryl,
 2) CN,
 3) halogen,
 4) (C=O)NR$^a$R$^b$,
 5) (C$_1$–C$_{10}$)alkyl,
 6) (C$_2$–C$_8$)alkenyl,
 7) (C$_2$–C$_8$)alkynyl, or
 8) heterocyclyl,
  wherein r and s are independently 0 or 1, and said aryl, alkyl, alkenyl, alkynyl and heterocyclyl optionally substituted with one or more substituents selected from $R^7$;
$R^7$ is:
 1) O$_r$(C=O)$_s$NR$^a$R$^b$,
 2) (C=O)$_r$O$_s$aryl,
 3) (C=O)$_r$O$_s$-heterocyclyl,
 4) halogen,
 5) OH,
 6) oxo,
 7) O(C$_1$–C$_3$)perfluoroalkyl,
 8) (C$_1$–C$_3$)perfluoroalkyl,
 9) (C=O)$_r$O$_s$(C$_1$–C$_6$)alkyl,
 10) CHO,
 11) CO$_2$H,
 12) CN,
 13) (C$_1$–C$_6$)alkyl-NR$^a$R$^b$, or
 14) (C$_1$–C$_6$)alkyl-heterocyclyl,
  wherein r and s are independently 0 or 1, and said aryl, heterocyclyl and alkyl are optionally substituted with one to three substituents selected from R$^d$;
$R^a$ and $R^b$ are independently
 1) H,
 2) (C=O)$_r$(C$_1$–C$_{10}$)alkyl,
 3) S(O)$_2$R$^c$,
 4) (C=O)$_r$heterocyclyl,
 5) (C=O)$_r$aryl, or
 6) CO$_2$R$^c$,
  wherein r is 0 or 1 and said alkyl, heterocyclyl, and aryl optionally substituted with one or more substituents selected from R$^d$, or $R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^d$;

$R^c$ is $(C_1–C_6)$alkyl, aryl, or heterocyclyl; and $R^d$ is:
1) $(C=O)_rO_s(C_1–C_{10})$alkyl, wherein r and s are independently 0 or 1, optionally substituted with up to three substituents selected from OH, $(C_1–C_6)$alkoxy, halogen, heterocyclyl, CN, oxo, $N(R^e)_2$ and $S(O)_2R^c$,
2) $O_r(C_1–C_3)$perfluoroalkyl,
3) $(C_0–C_6)$alkylene-$S(O)_mR^c$, wherein m is 0, 1, or 2,
4) oxo,
5) OH,
6) halo,
7) CN,
8) $(C_0–C_6)$alkylene-aryl, optionally substituted with up to three substituents selected from $R^e$,
9) $(C_0–C_6)$alkylene-heterocyclyl, optionally substituted with up to three substituents selected from $R^e$,
10) $C(O)R^c$,
11) $CO_2R^c$,
12) $C(O)H$,
13) $N(R^e)_2$, or
14) $CO_2H$;

$R^e$ is:
1) H,
2) $(C_1–C_6)$alkyl, optionally substituted with one or more substituents selected from OH, heterocyclyl, $(C_1–C_6)$alkoxy, halogen, CN, oxo, $N(R^f)_2$ and $S(O)_2R^c$,
3) aryl, optionally substituted with one or more substituents selected from OH, heterocyclyl, $(C_1–C_6)$alkoxy, halogen, CN, $N(R^f)_2$ and $S(O)_2R^c$,
4) heterocyclyl, optionally substituted with one or more substituents selected from OH, heterocyclyl, $(C_1–C_6)$alkoxy, halogen, CN, oxo, $N(R^f)_2$ and $S(O)_2R^c$, or
6) $S(O)_2R^c$, or if two $R^e$'s are on a nitrogen atom, they can be taken together with the nitrogen to form a heterocycle with 5–7 atoms, optionally containing, in addition to the nitrogen, one or two additional heteroatoms selected from N, O and S, said heterocycle optionally substituted with one or more substituents selected from OH, $(C_1–C_6)$alkoxy, halogen, CN, oxo, $N(R^f)_2$ and $S(O)_2R^c$; and $R^f$ is H, aryl or $(C_1–C_6)$alkyl.

Another embodiment of the present invention is the compound of Formula I as described above, wherein Y is S;

$R^1$ is H, $(C_1–C_6)$alkyl, or $O(C_1–C_6)$alkyl;

$R^2$ is:
1) H, provided that both $R^1$ and $R^2$ are not H at the same time,
2) $O_r(C_1–C_6)$perfluoroalkyl,
3) OH,
4) CN,
5) halogen,
6) $(C=O)_rO_s(C_1–C_{10})$alkyl,
7) $(C=O)_rO_s(C_2–C_{10})$alkenyl,
8) $(C=O)_rO_s(C_2–C_{10})$alkynyl,
9) $(C=O)_rO_s$aryl,
10) $(C=O)_rO_s$heterocyclyl,
11) $(C_0–C_6)$alkyl-$NR^aR^b$, or
12) $(C_1–C_6)$heterocyclyl, wherein r and s are independently 0 or 1, and said alkyl, alkenyl, alkynyl, aryl, and heterocyclyl is optionally substituted with one or more substituents selected from $R^7$;

$R^6$ is:
1) aryl,
2) CN,
3) halogen,
4) $(C=O)NR^aR^b$,
5) $(C_1–C_6)$alkyl,
6) $(C_2–C_6)$alkenyl,
7) $(C_2–C_6)$alkynyl, or
8) heterocyclyl, wherein r and s are independently 0 or 1, and said aryl, alkyl, alkenyl, alkynyl and heterocyclyl optionally substituted with one to three substituents selected from $R^7$;

$R^7$ is:
1) $O_r(C=O)_sNR^aR^b$,
2) $(C=O)_rO_s$aryl,
3) $(C=O)_rO_s$-heterocyclyl,
4) halogen,
5) OH,
6) oxo,
7) $O(C_1–C_3)$perfluoroalkyl,
8) $(C_1–C_3)$perfluoroalkyl,
9) $(C=O)_rO_s(C_1–C_6)$alkyl,
10) CHO,
11) $CO_2H$,
12) CN,
13) $(C_1–C_6)$alkyl-$NR^aR^b$, or
14) $(C_1–C_6)$alkyl-heterocyclyl, wherein r and s are independently 0 or 1, and said aryl, heterocyclyl and alkyl are optionally substituted with one to three substituents selected from $R^d$;

$R^a$ and $R^b$ are independently:
1) H,
2) $(C=O)_r(C_1–C_{10})$alkyl,
3) $S(O)_2R^c$,
4) $(C=O)_r$heterocyclyl,
5) $(C=O)_r$aryl, or
6) $CO_2R^c$, wherein r is 0 or 1 and said alkyl, heterocyclyl, and aryl optionally substituted with one or more substituents selected from $R^d$, or $R^a$ and $R^b$ are taken together with the nitrogen to which they are attached to form a monocyclic 5–7 membered heterocycle optionally containing, in addition to the nitrogen, one or two additional heteroatoms selected from N, O and S, said heterocycle optionally substituted with one to three substituents selected from $R^d$; and $R^d$ is:
1) $(C=O)_rO_s(C_1–C_6)$alkyl, wherein r and s are independently 0 or 1, optionally substituted with up to three substituents selected from OH, $(C_1–C_6)$alkoxy, halogen, CN, oxo, $N(R^e)_2$ and $S(O)_2R^c$,
2) $O_r(C_1–C_3)$perfluoroalkyl,
3) $(C_0–C_6)$alkylene-$S(O)_mR^c$, wherein m is 0, 1, or 2,
4) oxo,
5) OH,
6) halo,
7) CN,
8) $(C_0–C_6)$alkylene-aryl, optionally substituted with up to three substituents selected from $R^e$,
9) $(C_0–C_6)$alkylene-heterocyclyl, optionally substituted with up to three substituents selected from $R^e$,
10) $(C_0–C_6)$alkylene-$N(R^e)_2$,
11) $C(O)R^c$,
12) $CO_2R^c$, 13) C(O)H, or
14) CO$_2$H.

A third embodiment is represented by the compound of Formula I described above further defined such that A and B are N; and R$^6$ is phenyl, CN, or pyridyl said phenyl and pyridyl optionally substituted with one to three substituents selcted from R$^7$.

And yet another embodiment is compound of Formula I described above wherein R$^1$ is H and R$^2$ is O$_r$(C$_1$–C$_6$)alkyl, wherein r is 0 or 1, optionally substituted with one to three substituents selected from R$^7$; or (C$_0$–C$_6$)alkyl-NR$^a$R$^b$.

A further embodiment is a compound selected from:
2-({6-[4-(2-morpholin-4-ylethyl)piperazin-1-yl]pyrimidin-4-yl}amino)-1,3-thiazole-5-carbonitrile;
2-({6-[4-(2-morpholin-4-yl-2-oxoethyl)piperazin-1-yl]pyrimidin-4-yl}amino)-1,3-thiazole-5-carbonitrile;
N-(tert-butyl)-2-(4-{6-[(5-cyano-1,3-thiazol-2-yl)amino]pyrimidin-4-yl}piperazin-1-yl)acetamide;
2-({6-[4-(1,1-dioxidotetrahydrothien-3-yl)piperazin-1-yl]pyrimidin-4-yl}amino)-1,3-thiazole-5-carbonitrile;
2-(4-{6-[(5-cyano-1,3-thiazol-2-yl)amino]pyrimidin-4-yl}piperazin-1-yl)-N-isopropylacetamide;
2-(1-{6-[(5-cyano-1,3-thiazol-2-yl)amino]pyrimidin-4-yl}piperidin-4-yl)-N-isopropylacetamide; and
2-({6-[4-(2-oxopiperidin-3-yl)piperazin-1-yl]pyrimidin-4-yl}amino)-1,3-thiazole-5-carbonitrile; or a pharmaceutically acceptable salt or stereoisomer thereof.

And still another embodiment is a compound which is 2-({6-[4-(1,1-dioxidotetrahydrothien-3-yl)piperazin-1-yl]pyrimidin-4-yl}amino)-1,3-thiazole-5-carbonitrile

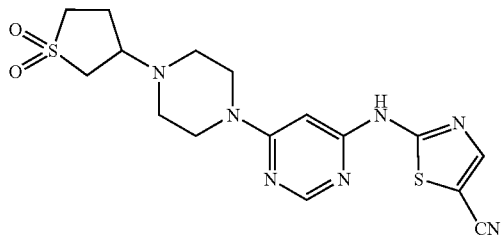

or a pharmaceutically acceptable salt or stereoisomer thereof.

Also encompassed by the present invention is a compound which is N-(tert-butyl)-2-(4-{6-[(5-cyano-1,3-thiazol-2-yl)amino]pyrimidin-4-yl}piperazin-1-yl)acetamide

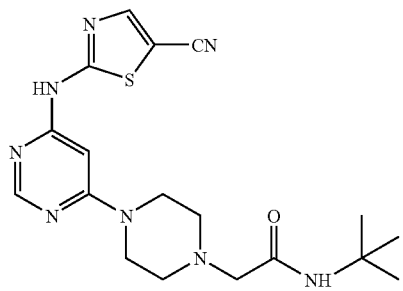

or a pharmaceutically acceptable salt thereof.

Further encompassed by the instant invention is a compound which is the (R) or (S) enantiomer of 2-({6-[4-(1,1-dioxidotetrahydrothien-3-yl)piperazin-1-yl]pyrimidin-4-yl}amino)-1,3-thiazole-5-carbonitrile in enantiomerically pure form as characterized by an enatiomeric excess of at least 98%, or a pharmaceutically acceptable salt thereof.

And yet another embodiment of the invention is a compound which is 2-(4-{6-[(5-cyano-1,3-thiazol-2-yl)amino]pyrimidin-4-yl}piperazin-1-yl)-N-isopropylacetamide

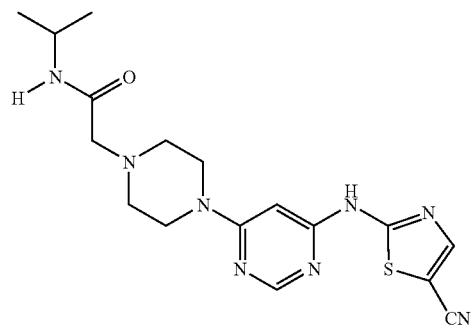

or a pharmaceutically acceptable salt thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like). In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a claimed compound. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. A further preferred group of cancers for treatment with the present compounds is a cancer selected from lung cancer, prostate cancer, breast cancer and colorectal cancer.

The utility of angiogenesis inhibitors in the treatment of cancer is known in the literature, see J. Rak et al. *Cancer Research*, 55:4575–4580, 1995, for example. The role of angiogenesis in cancer has been shown in numerous types of cancer and tissues: breast carcinoma (G. Gasparini and A. L. harris, *J. Clin. Oncol.*, 1995, 13:765–782; M. Toi et al., *Japan. J. Cancer Res.*, 1994, 85:1045–1049); bladder carcinomas (A. J. Dickinson et al., *Br. J. Urol.*, 1994, 74:762–766); colon carcinomas (L. M. Ellis et al., *Surgery*, 1996, 120(5):871–878); and oral cavity tumors (J. K. Williams et al., *Am. J. Surg.*, 1994, 168:373–380).

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets*, 10:285–292 (1999)). In fact, angiogenesis is essential for tumor growth and metastasis. (S. P. gunningham, et al., *Can. Research*, 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formual I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108.) For the role of VEGF in skin angiogenesis, see Michael Detmar, *J. Dermatological Sci.*, 24 Suppl. 1, S78–S84 (2000).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.*, 28, pp. 41–45, 1999; Gerber et al., *Nature Medicine*, Vol. 5, No. 6, pp. 623–628, June 1999.) And since VEGF directly promotes osteoclastic bone resorption through KDR/Flk-1 expressed in mature osteoclasts (FEBS Let. 473:161–164 (2000); *Endocrinology*, 141:1667 (2000)), the instant compounds are also useful to treat and prevent conditions related to bone resorption, such as osteoporosis and Paget's disease.

A method of treating or preventing preeclampsia is also within the scope of the present invention, which comprises administering a therapeutically effective amount of a compound of Formula I. Studies have shown that the action of VEGF on the Flt-1 receptor is pivotal in the pathogenesis of preeclampsia. (*Laboratory Investigation* 79:1101–1111 (September 1999).) Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of the present invention. The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med* 7:222–227 (2001)).

The instant compounds can also be used to prevent or treat tissue damage during bacterial meningitis, such as tuberculous meningitis. (Matsuyama et al., *J. Neurol. Sci.* 186: 75–79 (2001)). The instant invention therefore encompasses a method of treating or preventing tissue damage due to bacterial meningitis which comprises administering a therapeutically effective amount of a claimed compound. Studies have shown that VEGF is secreted by inflammatory cells during bacterial meningitis and that VEGF contributes to blood-brain barrier disruption. (van der Flier et al., *J. Infectious Diseases*, 183:149–153 (2001)). The claimed compounds can inhibit VEGF-induced vascular permeability and therefore serve to prevent or treat blood-brain barrier disruption associated with bacterial meningitis.

The present invention further encompasses a method to treat or prevent endometriosis comprised of administering a therapeutically effective amount of a claimed compound. An increase in VEGF expression and angiogenesis is associated with the progression of endometriosis (Stephen K. Smith, *Trends in Endocrinology & Metabolism*, Vol. 12, No. 4, May/June 2001). Inhibition of VEGF by the current compounds would therefore inhibit angiogenesis and treat endometriosis.

A further embodiment of the present invention is a method of treating acute myeloid leukemia (AML) which comprises administering a therapeutically effective amount of a claimed compound. Activation of FLT3 on leukemic cells by FLT3 ligand leads to receptor dimerization and signal transduction in pathways that promote cell growth and inhibit apoptosis (*Blood*, Vol. 98, No. 3, pp. 885–887 (2001)). The present compounds are therefore useful to treat AML via inhibition of the tyrosine kinase domain of Flt-3.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, EHV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186). The use of angiogenesis inhibitors with other chemotherapeutic agents is especially desirable since the normalization of tumor vasculature improves the delivery of the other therapeutic agents. (Nature Medicine, Vol. 7. No. 9, pp. 987–989 (September 2001)). "Estrogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(H)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7] indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl) sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy- 14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N-4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

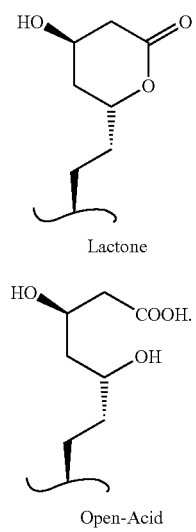

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)-quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl)methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl) 4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2'] bipyridin-5'-ylmethyl]-3H-imidazol-4-ylmethyl}benzonitrile, 4-{3-[4-(2-oxo-2H-[1,2']bipyridin- 5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl]benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriaza-cyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo[d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394–1401 (1999).

Examples of HIV protease inhibitors include amprenavir, abacavir, CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp. 963–968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an IC50 for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, U.S. Pat. No. 5,710,140, issued Jan. 20, 1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

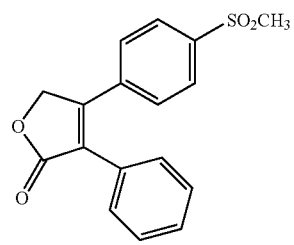

5-chloro-3-(4-methylsulfonyl)phenyl-2-(2-methyl-5-pyridinyl)pyridine;

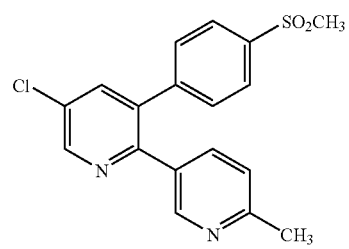

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

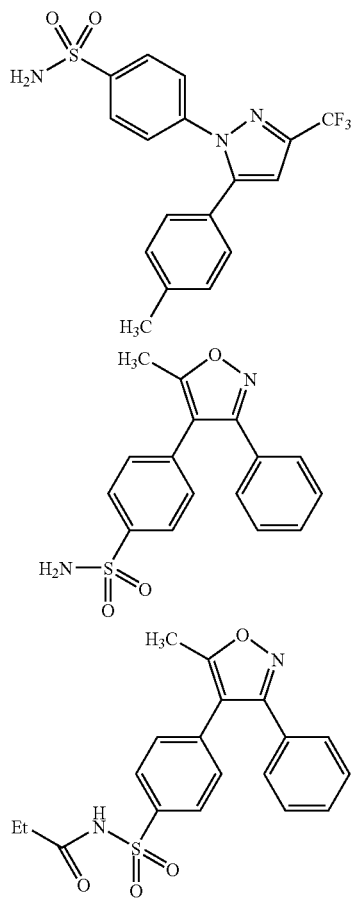

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604, 260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RP14610, NX31838, sulfated mannopentaose phosphate, 7,7-(carbonyl-bis[imino-N-methyl-4,2-pyrrolocarbonyl-imino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\mu_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

Combinations with compounds other than anti-cancer compounds are also encompassed to treat conditions other than cancer. For example, combinations of the instantly claimed compounds with PPAR-γ (i.e., PPAR-gamma) agonists are useful in the treatment of diabetic retinopathy. PPAR-γ is the nuclear peroxisome proliferator-activated receptor γ. The expression of PPAR-γ on endothelial cells and its involvement in angiogenesis in corneal and choroidal experimental systems has been reported in the literature (see *J. Cardiovasc. Pharmacol.* 1998; 31:909–913; *J. Biol.*

Chem. 1999;274:9116–9121; Invest. Ophthalmol Vis. Sci. 2000; 41:2309–2317). More recently, PPAR-γ agonists have been shown to inhibit the angiogenic response to VEGF in vitro; both troglitazone and rosiglitazone maleate inhibit the development of retinal neovascularization in mice. (Arch. Ophthalmol. 2001; 119:709–717). Examples of PPAR-γ aganoists and PPAR-γ/α aganoists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697). Thus, a method of treating or preventing diabetic retinopathy which comprises administering a therapeutically effective amount of a claimed compound in combination with a PPAR-γ agonist is also within the scope of the present invention.

Another aspect of the invention is illustrated by a composition comprising a therapeutically effective amount of the disclosed tyrosine kinase inhibitors and a steroidal anti-inflammatory. Steroidal anti-inflammatories include, but are not limited to, corticosteroids, mineralocorticoids, dexamethasone, prednisone, prednisolone, methylpred, and betamethasone. This combination is particularly useful in ophthalmic formulations which may, in some cases, be associated with irritation of the ocular tissues.

A particularly useful combination for the treatment of diseases wherein aberrant angiogensis is present invioves administering a therapeutically effective amount of the instantly disclosed tyrosine-kinase inhibiting compounds in combination with photodynamic therapy and a photosensitive drug such as verteoporfin (BPD-MA) (Carruth, Clinical Applications of Photodynamic Therapy, Int. J. Clin. Pract. 1998; 52(1):39–42). Such diseases include, but are not limited to, age-related macular degeneration (Bressler, Treatment of Age-Related Macular Degeneration with Photodynamic Therapy Investigation Using Verteoporfin, Invest. Ophthalmol. Vis. Sci. 1998; 39 S242); cancer, especially melanoma and non-melanoma skin cancer, including basal cell and squamous cell carcinomas, (Hassan and Parrish, Photodynamic Therpay in Cancer, Cancer Med 1997; Dougherty et al., Photodynamic Therapy for the Treatment of Cancer: Current Status and Advances in Photodynamic Therapy of Neoplastic Disease. Kessel (Ed.), CRC Press, 1989; 1–19); Dougherty et al., Photodynamic Therpay, J. Natl. Cancer Inst., 1998, 90(12): 889–905; Jori, Factors Controlling the Selectivity and Efficiency of Tumour Damage in Photodynamic Therapy, Laser Med. Sci. 1990; 5: 115–120; Zhou, Mechanism of Tumour Necrosis Induced by Photodynamic Therapy, J. Photochem. Photobiol. 1989; 3: 299–318), psoriasis (Bissonnette et al., Photodynamic Therapy of Psoriasis and Psoriatic Arthritis with BPD verteporfin. 7$^{th}$ Biennial Congress, International Photodynamic Association, Nantes, France 1998:73), and rheumatoid arthritis (Hendrich et al., Photodynamic Therapy for Rheumatoid Arthritis. Lasermedizin 11: 73–77 (1995); Hendrich et al. Photodynamic Laser Therapy for Rheumatoid Arthritis: Cell Culture Studies and Animal Experiments, Knee Surg Sports Traumatol Arthroscopy 5: 58–63 (1997).

Another embodiment of the instant invention is the use of the presently disclosed compounds in combination with gene therapy for the treatment of cancer. For an overview of genetic strategies to treating cancer see Hall et al (Am J Hum Genet 61:785–789, 1997) and Kufe et al (Cancer Medicine, 5th Ed, pp 876–889, BC Decker, Hamilton 2000). Gene therapy can be used to deliver any tumor suppresing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8): 1105–13), and interferon gamma (J Immunol 2000; 164:217–222).

VEGF receptor tyrosine kinase have been reported to cause a sustained increase in blood pressure in rats when administered more than once, particularly when administered chronically. It is desirable, however, to produce an antiangiogenic effect without causing hypertension. This can be achieved by treating a disease state associated with angiogenesis with a therapeutically effective amount of a combination of an anti-angiogenic agent, such as those presently disclosed, and an anti-hypertensive agent (see WO 01/74360, hereby incorporated by reference). The present invention therefore encompasses a pharmaceutical composition comprising a therapeutically effective amount of a combination of a compound of Formula I and an anti-hypertensive compound.

An anti-hypertensive is any agent which lowers blood pressure. There are numerous categories of anti-hypertensive agents including calcium channel blockers, angiotensin converting enzyme inhibitors (ACE inhibitors), angiotensin II receptor antagonists (A-II antagonists), diuretics, beta-adrenergic receptor blockers (β-blockers), vasodilators, alpha-adrenergic receptor blockers (α-blockers), selective neutral endopeptidase (NEP) inhibitors and dual ACE-NEP inhibitors. Any anti-hypertensive agent may be used in accordance with this invention and examples from each class are given below.

Calcium channel blockers which are within the scope of this invention include, but are not limited to: amlodipine (U.S. Pat. No. 4,572,909); bepridil (U.S. Pat. No. 3,962,238 or U.S. Reissue No. 30,577); clentiazem (U.S. Pat. No. 4,567,175); diltiazem (U.S. Pat. No. 3,562,257); fendiline (U.S. Pat. No. 3,262,977); gallopamil (U.S. Pat. No. 3,261, 859); mibefradil (U.S. Pat. No. 4,808,605); prenylamine (U.S. Pat. No. 3,152,173); semotiadil (U.S. Pat. No. 4,786, 635); terodiline (U.S. Pat. No. 3,371,014); verapamil (U.S. Pat. No. 3,261,859); aranidipine (U.S. Pat. No. 4,446,325); bamidipine (U.S. Pat. No. 4,220,649); benidipine (European Patent Application Publication No. 106,275); cilnidipine (U.S. Pat. No. 4,672,068); efonidipine (U.S. Pat. No. 4,885, 284); elgodipine (U.S. Pat. No. 4,952,592); felodipine (U.S. Pat. No. 4,264,611); isradipine (U.S. Pat. No. 4,466,972); lacidipine (U.S. Pat. No. 4,801,599); lercanidipine (U.S. Pat. No. 4,705,797); manidipine (U.S. Pat. No. 4,892,875); nicardipine (U.S. Pat. No. 3,985,758); nifedipine (U.S. Pat. No. 3,485,847); nilvadipine (U.S. Pat. No. 4,338,322); nimodipine (U.S. Pat. No. 3,799,934); nisoldipine (U.S. Pat. No. 4,154,839); nitrendipine (U.S. Pat. No. 3,799,934); cinnarizine (U.S. Pat. No. 2,882,271); flunarizine (U.S. Pat. No. 3,773,939); lidoflazine (U.S. Pat. No. 3,267,104); lomerizine (U.S. Pat. No. 4,663,325); bencyclane (Hungarian Patent No. 151,865); etafenone (German Patent No. 1,265,758); and perhexiline (British Patent No. 1,025,578). The disclosures of all such patents and patent applications are incorporated herein by reference.

Angiotensin Converting Enzyme Inhibitors (ACE-Inhibitors) which are within the scope of this invention include, but are not limited to: alacepril (U.S. Pat. No. 4,248,883); benazepril (U.S. Pat. No. 4,410,520); captopril (U.S. Pat. Nos. 4,046,889 and 4,105,776); ceronapril (U.S. Pat. No. 4,452,790); delapril (U.S. Pat. No. 4,385,051); enalapril (U.S. Pat. No. 4,374,829); fosinopril (U.S. Pat. No. 4,337, 201); imidapril (U.S. Pat. No. 4,508,727); lisinopril (U.S. Pat. No. 4,555,502); moveltipril (Belgium Patent No. 893, 553); perindopril (U.S. Pat. No. 4,508,729); quinapril (U.S. Pat. No. 4,344,949); ramipril (U.S. Pat. No. 4,587,258); spirapril (U.S. Pat. No. 4,470,972); temocapril (U.S. Pat. No. 4,699,905); and trandolapril (U.S. Pat. No. 4,933,361). The disclosures of all such patents are incorporated herein by reference.

Angiotensin-II receptor antagonists (A-II antagonists) which are within the scope of this invention include, but are not limited to: candesartan (U.S. Pat. No. 5,196,444); eprosartan (U.S. Pat. No. 5,185,351); irbesartan (U.S. Pat. No. 5,270,317); losartan (U.S. Pat. No. 5,138,069); and valsartan (U.S. Pat. No. 5,399,578. The disclosures of all such U.S. patents are incorporated herein by reference.

β-Blockers which are within the scope of this invention include, but are not limited to: acebutolol (U.S. Pat. No. 3,857,952); alprenolol (Netherlands Patent Application No. 6,605,692); amosulalol (U.S. Pat. No. 4,217,305); arotinolol (U.S. Pat. No. 3,932,400); atenolol (U.S. Pat. Nos. 3,663, 607 and 3,836,671); befunolol (U.S. Pat. No. 3,853,923); betaxolol (U.S. Pat. No. 4,252,984); bevantolol (U.S. Pat. No. 3,857,891); bisoprolol (U.S. Pat. No. 4,25 8,062); bopindolol (U.S. Pat. No. 4,340,541); bucumolol (U.S. Pat. No. 3,663,570); bufetolol (U.S. Pat. No. 3,723,476); bufuralol (U.S. Pat. No. 3,929,836); bunitrolol (U.S. Pat. No. 3,541,130); bupranolol (U S. Patent No. 3,309,406); butidrine hydrochloride (French Patent No. 1,390,056); butofilolol (U.S. Pat. No. 4,302,601); carazolol (German Patent No. 2,240,599); carteolol (U.S. Pat. No. 3,910,924); carvedilol (U.S. Pat. No. 4,503,067); celiprolol (U.S. Pat. No. 4,034,009); cetamolol (U.S. Pat. No. 4,059,622); cloranolol (German Patent No. 2,213,044); dilevalol (Clifton et al., Journal of Medicinal Chemistry, 1982, 25, 670); epanolol (U.S. Pat. No. 4,167,581); indenolol (U.S. Pat. No. 4,045,482); labetalol (U.S. Pat. No. 4,012,444); levobunolol (U.S. Pat. No. 4,463,176); mepindolol (Seeman et al, Helv. Chim. Acta, 1971, 54, 2411); metipranolol (Czechoslovakian Patent Application No. 128,471); metoprolol (U.S. Pat. No. 3,873,600); moprolol (U.S. Pat. No. 3,501,769); nadolol (U.S. Pat. No. 3,935,267); nadoxolol (U.S. Pat. No. 3,819, 702); nebivalol (U.S. Pat. No. 4,654,362); nipradilol (U.S. Pat. No. 4,394,382); oxprenolol (British Patent No. 1,077, 603); penbutolol (U.S. Pat. No. 3,551,493); pindolol (Swiss Patents Nos. 469,002 and 472,404); practolol (U.S. Pat. No. 3,408,387); pronethalol (British Patent No. 909,357); propranolol (U.S. Pat. Nos. 3,337,628 and 3,520,919); sotalol (Uloth et al., Journal of Medicinal Chemistry, 1966, 9, 88); sulfinalol (German Patent No. 2,728,641); talinolol (U.S. Pat. Nos. 3,935,259 and 4,038,313); tertatolol (U.S. Pat. No. 3,960,891); tilisolol (U.S. Pat. No. 4,129,565); timolol (U.S. Pat. No. 3,655,663); toliprolol (U.S. Pat. No. 3,432,545); and xibenolol (U.S. Pat. No. 4,018,824). The disclosures of all such patents, patent applications and references are incorporated herein by reference.

α-Blockers which are within the scope of this invention include, but are not limited to: amosulalol (U.S. Pat. No. 4,217,305); arotinolol; dapiprazole (U.S. Pat. No. 4,252, 721); doxazosin (U.S. Pat. No. 4,188,390); fenspiride (U.S. Pat. No. 3,399,192); indoramin (U.S. Pat. No. 3,527,761); labetolol; naftopidil (U.S. Pat. No. 3,997,666); nicergoline (U.S. Pat. No. 3,228,943); prazosin (U.S. Pat. No. 3,511, 836); tainsulosin (U.S. Pat. No. 4,703,063); tolazoline (U.S. Pat. No. 2,161,938); trimazosin (U.S. Pat. No. 3,669,968); and yohimbine. The disclosures of all such U.S. patents are incorporated herein by reference.

The term "vasodilator" as used herein is meant to include cerebral vasodilators, coronary vasodilators and peripheral vasodilators. Cerebral vasodilators within the scope of this invention include, but are not limited to: bencyclane; cinnarizine; citicoline; cyclandelate (U.S. Pat. No. 3,663,597); ciclonicate (German Patent No. 1,910,481); diisopropylamine dichloroacetate (British Patent No. 862,248); eburnamonine (Hermann et al., Journal of the American Chemical Society, 1979, 101, 1540); fasudil (U.S. Pat. No. 4,678, 783); fenoxedil (U.S. Pat. No. 3,818,021); flunarizine (U.S. Pat. No. 3,773,939); ibudilast (U.S. Pat. No. 3,850,941); ifenprodil (U.S. Pat. No. 3,509,164); lomerizine (U.S. Pat. No. 4,663,325); nafronyl (U.S. Pat. No. 3,334,096); nicametate (Blicke et al., Journal of the American Chemical Society, 1942, 64, 1722); nicergoline; nimodipine (U.S. Pat. No. 3,799,934); papaverine (Goldberg, Chem. Prod. Chem. News, 1954, 17, 37 1; pentifylline (German Patent No. 860,217); tinofedrine (U.S. Pat. No. 3,767,675); vincamine (U.S. Pat. No. 3,770,724); vinpocetine (U.S. Pat. No. 4,035, 750); and viquidil (U.S. Pat. No. 2,500,444). The disclosures of all such patents and references are incorporated herein by reference. Coronary vasodilators within the scope of this invention include, but are not limited to: amotriphene (U.S. Pat. No. 3,010,965); bendazol (Feitelson, et al., J. Chem. Soc. 1958, 2426); benfurodil hemisuccinate (U.S. Pat. No. 3,355,463); benziodarone (U.S. Pat. No. 3,012,042); chloracizine (British Patent No. 740,932) chromonar (U.S. Pat. No. 3,282,938); clobenfural (British Patent No. 1,160,925); clonitrate; cloricromen (U.S. Pat. No. 4,452,811); dilazep (U.S. Pat. No. 3,532,685); dipyridamole (British Patent No. 807,826); droprenilamine (German Patent No. 2,521,113); efloxate (British Patents Nos. 803,372 and 824,547); erythrityl tetranitrate; etafenone (German Patent No. 1,265,758); fendiline (U.S. Pat. No. 3,262,977); floredil (German Patent No. 2,020,464); ganglefene (U.S.S.R. Patent No. 115,905); hexestrol bis(P-diethylaminoethyl) ether (Lowe et al., J. Chem. Soc. 1951, 3286); hexobendine (U.S. Pat. No. 3,267, 103); itramin tosylate (Swedish Patent No. 168,308); khellin (Baxter et al., Journal of the Chemical Society, 1949, S 30); lidoflazine (U.S. Pat. No. 3,267,104); mannitol hexanitrate; medibazine (U.S. Pat. No. 3,119,826); nitroglycerin; pentaerythritol tetranitrate; pentrinitrol (German Patent No. 638,422-3); perhexiline; pimefylline (U.S. Pat. No. 3,350, 400); prenylamine (U.S. Pat. No. 3,152,173); propatyl nitrate (French Patent No. 1,103,113); trapidil (East German Patent No. 55,956); tricromyl (U.S. Pat. No. 2,769,015); trimetazidine (U.S. Pat. No. 3,262,852); trolnitrate phosphate; visnadine (U.S. Pat. Nos. 2,816,118 and 2,980,699. The disclosures of all such patents and references are incorporated herein by reference. Peripheral vasodilators within the scope of this invention include, but are not limited to: aluminium nicotinate (U.S. Pat. No. 2,970,082); bamethan (Corrigan et al., Journal of the American Chemical Society, 1945, 67, 1894); bencyclane; betahistine (Walter et al, Journal of the American Chemical Society, 1941, 63); bradykinin; brovincamine (U.S. Pat. No. 4,146,643); bufeniode (U.S. Pat. No. 3,542,870); buflomedil (U.S. Pat. No. 3,895,030); butalamine (U.S. Pat. No. 3,338,899); cetiedil (French Patent No. 1,460,571); ciclonicate (German Patent No. 1,910,481); cinepazide (Beiguim Patent No. 730,345); cinnarizine; cyclandelate; diisopropylamine dichloroacetate; eledoisin (British Patent No. 984,810); fenoxedil; flunarizine; hepronicate (U.S. Pat. No. 3,384,642); ifenprodil; iloprost (U.S. Pat. No. 4,692,464); inositol niacinate (Badgett et al., Journal of the American Chemical Society, 1947, 69, 2907); isoxsuprine (U.S. Pat. No. 3,056,836); kallidin (Nicolaides et al., Biochem. Biophys. Res. Commun., 1961, 6, 210); kallikrein (German Patent No. 1,102,973); moxisylyte (German Patent No. 905,738); nafronyl; nicametate; nicergoline; nicofaranose (Swiss Patent No. 366,523); nylidrin (U.S. Pat. Nos. 2,661,372 and 2,661,373); pentifylline; pentoxifylline (U.S. Pat. No. 3,422,107); piribedil (U.S. Pat. No. 3,299,067); prostaglandin E1 (Merck Index, Twelfth Edition, Budaveri, Ed, New Jersey 1996, page 1353); suloctidil (German Patent No. 2,334,404); tolazoline (U.S. Pat. No. 2,161,938); and xanthinol niacinate (German Patent No. 1,102,750). The disclosures of all such patents and references are incorporated herein by reference.

The term "diuretic" as used herein includes but is not limited to diuretic benzothiadiazine derivatives, diuretic organomercurials, diuretic purines, diuretic steroids, diuretic sulfonamide derivatives, diuretic uracils and other diuretics such as amanozine (Austrian Patent No. 168,063); amiloride (Belgium Patent No. 639,386); arbutin (Tschitschibabin et al., Annalen, 1930, 479, 303); chlorazanil (Austrian Patent No. 168,063); ethacrynic acid (U.S. Pat. No. 3,255,241); etozolin (U.S. Pat. No. 3,072,653); hydracarbazine (British Patent No. 856,409); isosorbide (U.S. Pat. No. 3,160,641); mannitol; metochalcone (Freudenberg et al., Ber., 1957, 90, 957); muzolimine (U.S. Pat. No. 4,018,890); perhexiline; ticrynafen (U.S. Pat. No. 3,758,506); triamterene (U.S. Pat. No. 3,081,230); and urea. The disclosures of all such patents and references are incorporated herein by reference. Diuretic benzothiadiazine derivatives within the scope of this invention include, but are not limited to: althiazide (British Patent No. 902,658); bendroflumethiazide (U.S. Pat. No. 3,392, 168); benzthiazide (U.S. Pat. No. 3,440,244); benzyl hydrochlorothiazide (U.S. Pat. No. 3,108,097); buthiazide (British Patents Nos. 861,367 and 885,078); chlorothiazide (U.S. Pat. Nos. 2,809,194 and 2,937,169); chlorthalidone (U.S. Pat. No. 3,055,904); cyclopenthiazide (Belgium Patent No. 587,225); cyclothiazide (Whitehead et al Journal of Organic Chemistry, 1961, 26, 2814); epithiazide (U.S. Pat. No. 3,009,911); ethiazide (British Patent No. 861,367); fenquizone (U.S. Pat. No. 3,870,720); indapamide (U.S. Pat. No. 3,565,911); hydrochlorothiazide (U.S. Pat. No. 3,164, 588); hydroflumethiazide (U.S. Pat. No. 3,254,076); methyclothiazide (Close et al., Journal of the American Chemical Society, 1960, 82, 1132); meticrane (French Patents Nos. M2790 and 1,365,504); metolazone (U.S. Pat. No. 3,360, 518); paraflutizide (Belgium Patent No. 15 620,829); polythiazide (U.S. Pat. No. 3,009,911); quinethazone (U.S. Pat. No. 2,976,289); teclothiazide (Close et al., Journal of the American Chemical Society, 1960, 82, 1132); and trichlormethiazide (deStevens et al., Experientia, 1960, 16, 113). The disclosures of all such patents and references are incorporated herein by reference. Diuretic sulfonamide derivatives within the scope of this invention include, but are not limited to: acetazolamide (U.S. Pat. No. 2,554,816); ambuside (U.S. Pat. No. 3,188,329); azosemide (U.S. Pat. No. 3,665,002); bumetamide (U.S. Pat. No. 3,806,534); butazolamide (British Patent No. 769,757); chloraminophenamide (U.S. Pat. Nos. 2,909,194; 2,965,655; and 2,965, 656); clofenamide (Olivier, Rec. Trav. Chim., 1918, 37, 307); clopamide (U.S. Pat. No. 3,459,756); clorexolone (U.S. Pat. No. 3,183,243); disulfamide (British Patent No. 851,287); ethozolamide (British Patent No. 795,174); furosemide (U.S. Pat. No. 3,058,882); mefruside (U.S. Pat. No. 3,356,692); methazolamide (U.S. Pat. No. 2,783,241); piretamide (U.S. Pat. No. 4,010,273); torsemide (U.S. Pat. No. 4,018,929); tripamide (Japanese Patent No. 305,585); and xipamide (U.S. Pat. No. 3,567,777). The disclosures of all such patents and references are incorporated herein by reference.

Selective neural endopeptidase inhibitors are taught by Delaney et al. in U.S. Pat. Nos. 4,722,810 and 5,223,516 and the use of selective neutral endopeptidase inhibitors alone or in combination with angiotensin converting enzyme inhibitors to treat hypertension are disclosed by Delaney et al. U.K. Patent Application 2,207,351 and by Haslanger et al. in U.S. Pat. No. 4,749,688. Compounds possessing both neutral endopeptidase and angiotensin converting enzyme inhibition activity are disclosed by Flynn et al. in U.S. Pat. No. 5,366,973, European Patent Application 481,522 and PCT Patent Applications WO 93/16103, and WO 94/10193, Warshawsky et al. European Patent Applications 534,363, 534, 396 and 534,492, Fournie-Zaluski European Patent Application 524,553, Karanewsky et al. European Patent Application 599,444, Karanewsky European Patent Application 595, 610, Robl et al., European Patent Application 629,627, Robl U.S. Pat. No. 5,362,727 and European Patent Application 657,453. The disclosures of all such patents and publications are incorporated herein by reference.

Further, the anti-hypertensive agents which may be used in accordance with this invention and the pharmaceutically acceptable salts thereof may occur as prodrugs, hydrates or solvates. Said hydrates and solvates are also within the scope of the present invention. Preferred anti-hypertensive agents of the invention include, calcium channel blockers, A-II antagonists, ACE inhibitors and β-blockers. More preferred anti-hypertensive agents of the invention include ACE inhibitors, particularly lisinopril, enalapril and captopril, and A-II antagonists, particularly losartan. The anti-hypertensives described herein are generally commercially available, or they may be made by standard techniques including those described in the references cited above.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invetion therefore encompasses the use of the instantly claimed compounds in combination with a second agent selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be used as the second agent are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-(chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer which comprises administering a therapeutically effective amount of a claimed compound in combination with radiation therapy and/or in combination with an agent selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formual I in combination with paclitaxel or trastuzumab.

The invention further encompasses a method of treating or preventing cancer which comprises administering a therapeutically effective amount of a claimed compound in combination with a COX-2 inhibitor.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

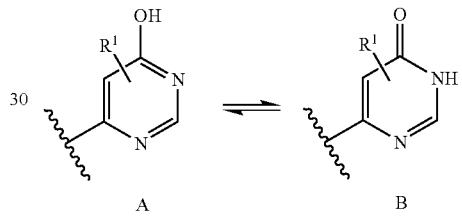

When any variable (e.g. $R^d$, $R^e$, $R^7$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched, straight-chain, and cyclic saturated aliphatic hydrocarbon groups having the specified number of carbon atoms. For example, $C_1$–$C_{10}$, as in "$C_1$–$C_{10}$ alkyl" is defined to include groups having 1, 2, 3, 4, 5, 6, 7, 8, 9 or 10 carbons in a linear, branched, or cyclic arrangement. For example, "$C_1$–$C_{10}$ alkyl" specifically includes methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least 1 carbon to carbon triple bond. Up to 3 carbon-carbon triple bonds may be present. Thus, "$C_2$–$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

In certain instances, substituents may be defined with a range of carbons that includes zero, such as ($C_0$–$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. If the heterocycle contains a nitrogen, it is understood that the corresponding N-oxides thereof are also emcompassed by this definition.

The alkyl, alkenyl, alkynyl, cycloalkyl, aryl, heteroaryl and heterocyclyl substituents may be unsubstituted or unsubstituted, unless specifically defined otherwise. For example, a ($C_1$–$C_6$)alkyl may be substituted with one or more substituents selected from OH, oxo, halogen, alkoxy, dialkylamino, or heterocyclyl, such as morpholinyl, piperidinyl, and so on. In the case of a disubstituted alkyl, for instance, wherein the substituents are oxo and OH, the following are included in the definition: —(C=O)$CH_2$CH(OH)$CH_3$, —(C=O)OH, —$CH_2$(OH)$CH_2$CH(O), and so on.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1–19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Preferably Y is O or S. More preferably Y is S.

A preferred definition of $R^2$ is ($C_1$–$C_{10}$)alkylene-$NR^aR^b$, wherein the alkylene is optionally substituted with one or more substituents selected from $R^7$.

Preferably $R^1$ is H or ($C_1$–$C_6$)alkyl. More preferably $R^1$ is H.

Preferably $R^4$ is H or $(C_1-C_6)$alkyl. More preferably $R^4$ is H.

Preferably $R^5$ is H.

Preferably $R^6$ is CN, halogen, phenyl, or heterocyclyl. Preferred definitions for heterocyclyl as defined in $R^6$ are thienyl, pyrimidinyl, pyridazinyl, pyrazinyl, and pyridyl. Most preferably $R^6$ is CN. A and B are preferably N.

In certain instances, $R^a$ and $R^b$ are defined such that they can be taken together with the nitrogen to which they are attached to form a monocyclic or bicyclic heterocycle with 5–7 members in each ring and optionally containing, in addition to the nitrogen, 1 or 2 additional heteroatoms selected from N, O and S, said heterocycle optionally substituted with one or more substituents selected from $R^d$. Examples of the heterocycles that can thus be formed include, but are not limited to the following, keeping in mind that the heterocycle is optionally substituted with one or more substituents chosen from $R^d$ and that the corresponding N-oxides are also encompassed by the claims:

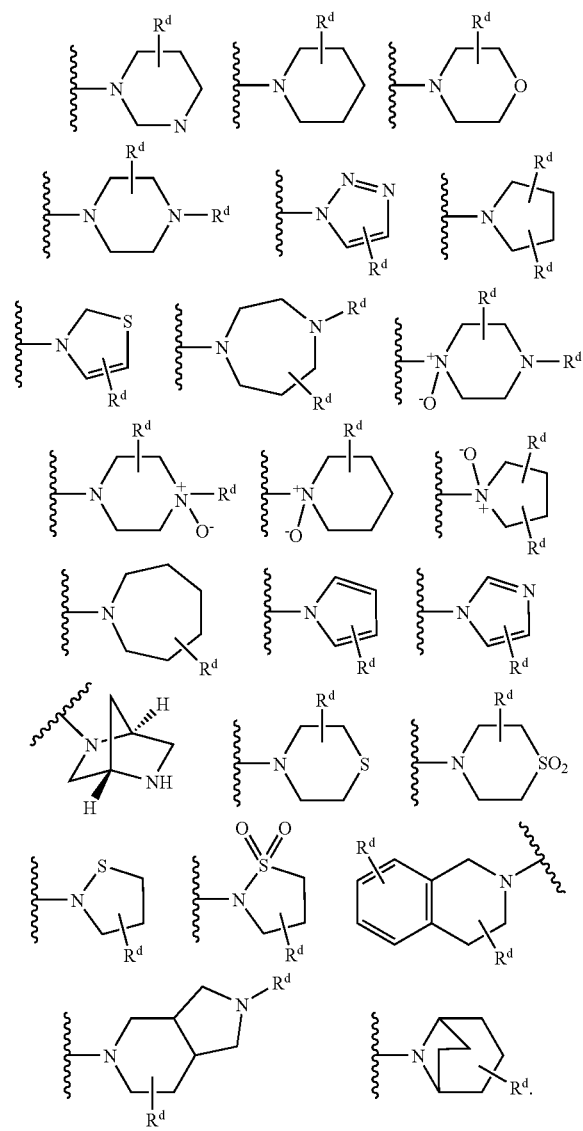

When $R^d$ is heterocyclyl, preferred definitions include pyridyl, pyrrolidinyl, pyrrolyl, piperidyl, morpholinyl, piperazinyl, furanyl, tetrahydrofuranyl, dioxidotetrahydrothienyl, thiomorpholinyl, dioxothiomorpholinyl, imidazolidinyl, oxoimidazolidinyl, dioxidothietanyl, and dioxyl, optionally substituted with one, two or three substituents selected from $R^e$, and the corresponding N-oxides of the N-containing heterocycles.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

Synopsis of Schemes

The compounds of the instant invention may be prepared from the appropriate thiourea A-2. The thioureas are available commercially or can be synthesized by one of the three alternate routes shown in Scheme A, where R represents the appropriate pyrimidinyl substituent.

SCHEME A

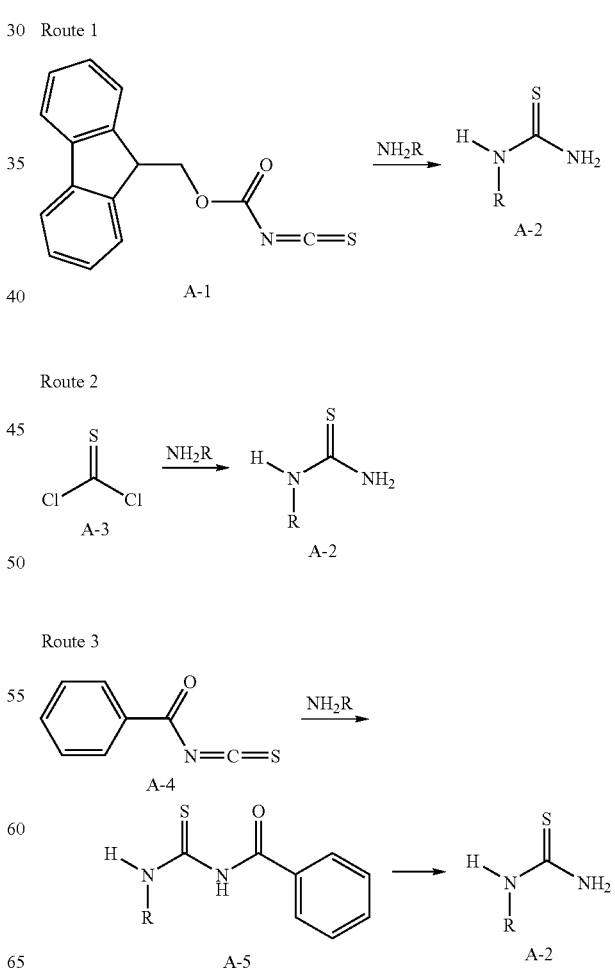

The target thiazoles B-3 and B-5 can then be arrived at by reacting the appropriate thiourea B-2 with a bromo acetal, B-1, or chloroacetaldehyde, B-4, as shown in Scheme B. The analogous oxazole compounds can be synthesized via methods well known in the art.

SCHEME B

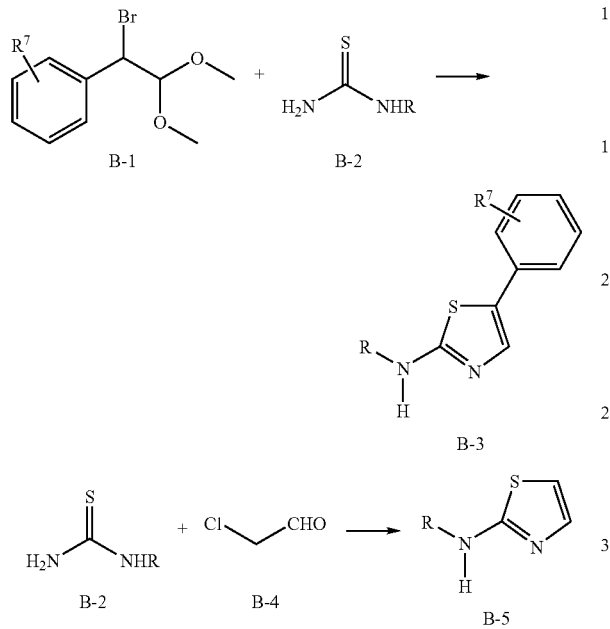

As shown in Scheme C, the resulting aminothiazole B-5 can be halogenated and C—C coupled to form adducts of general structure C-2.

SCHEME C

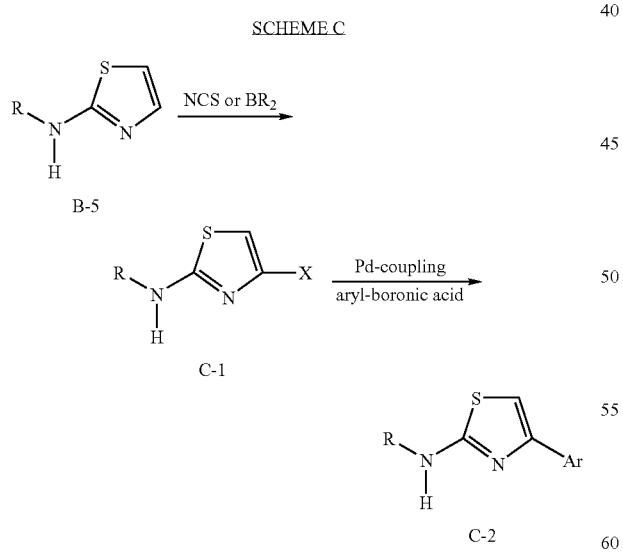

Alternatively, the protocol illustrated in Scheme D can be used to obtain compoundsof general Formula D-3. Scheme E illustrates one possible approach using this strategy in the preparation of the alkyleneamine substituted pyirimidines, E-6, of the present invention.

SCHEME D

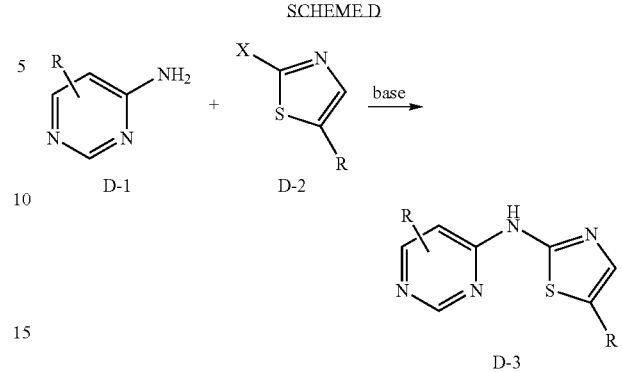

SCHEME E

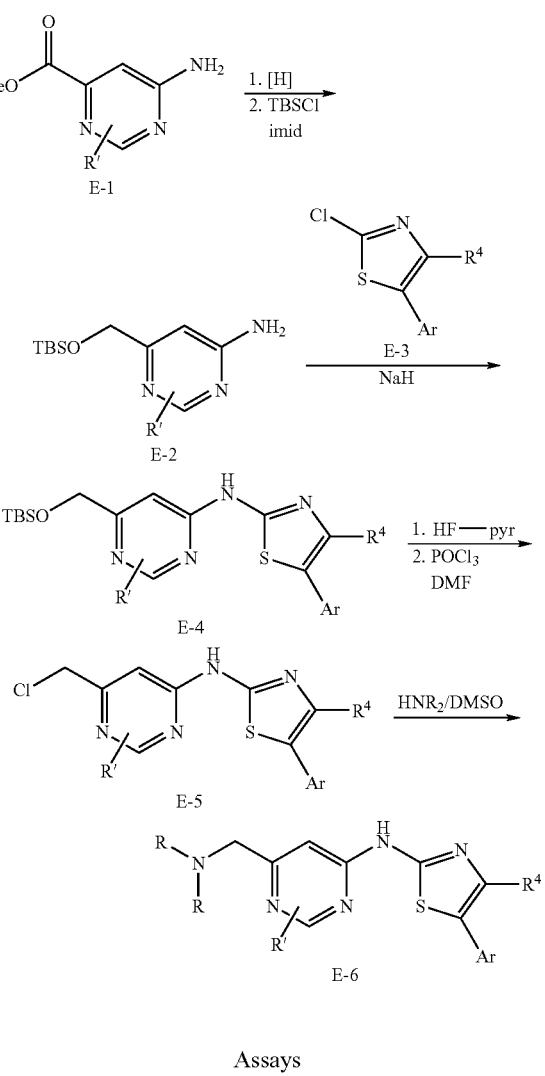

Assays

The compounds of the instant invention described in the Examples were tested by the assays described below and were found to have kinase inhibitory activity. Other assays are known in the literature and could be readily performed by those of skill in the art (see, for example, Dhanabal et al., Cancer Res. 59:189–197; xin et al., *J. Biol. Chem.* 274: 9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4, 0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4, 0.5 M NaCl, 5 mM DTT, 1 mM EDTA, 0.05% triton X-100, 50% glycerol, 10 mg/mL of each leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris pH 7.4, 0.1 M NaCl, 1 mM DTT, 10% glycerol, 100 mg/mL BSA.

10× Substrate: 750 μg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 μl of inhibitor or control to the assay in 50% DMSO.

2. Add 35 μl of reaction mix containing 5 μl of 10× reaction buffer, 5 μl 25 mM ATP/10 μCi [$^{33}$P]ATP (Amersham), and 5 μl 10× substrate.

3. Start the reaction by the addition of 10 μl of KDR (25 nM) in enzyme dilution buffer.

4. Mix and incubate at room temperature for 15 minutes.

5. Stop by the addition of 50 μl stop solution.

6. Incubate for 15 minutes at 4° C.

7. Transfer a 90 μl aliquot to filter plate.

8. Aspirate and wash 3 times with wash solution.

9. Add 30 μl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HWEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HWVECs frozen as primary culture isolates are obtained from Clonetics Corp. Cells are maintained in Endothelial Growth Medium (EGM; Clonetics) and are used for mitogenic assays described in passages 1–5 below.

Culture Plates: NUNCLON 96-well polystyrene tissue culture plates (NUNC #167008).

Assay Medium: Dulbecco's modification of Eagle's medium containing 1 mg/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human $VEGF_{165}$ (500 ng/mL; R&D Systems) and bFGF (10 ng/mL; R&D Systems) are prepared in Assay Medium.

10× [$^3$H]Thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) $Na_2CO_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% $CO_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.

3. After the 2-hour pretreatment period, cells are stimulated by addition of 10 μL/well of either Assay Medium, 10×VEGF solution or 10×bFGF solution. Cells are then incubated at 37° C. and 5% $CO_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of the present invention are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01–5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp. 915–924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.
2. The appropriate amount of reaction mix was prepared at room temperature:
   10× Buffer (20 mM Tris pH 7.4/0.1 M NaCl/1 mM DTT final)
   0.1M $MnCl_2$ (5 mM final)
   pEY substrate (75 μg/mL)
   ATP/[$^{33}$P]ATP (2.5 μM/1 μCi final)
   BSA (500 μg/mL final).
3. 5 μL of the diluted inhibitor was added to the reaction mix. (Final volume of 5 μL in 50% DMSO). To the positive control wells, blank DMSO (50%) was added.
4. 35 μL of the reaction mix was added to each well of a 96 well plate.
5. Enzyme was diluted into enzyme dilution buffer (kept at 4° C.).
6. 10 μL of the diluted enzyme was added to each well and mix (5 nM final). To the negative control wells, 10 μL 0.5 M EDTA was added per well instead (final 100 mM).
7. Incubation was then carried out at room temperature for 30 minutes.
8. Stopped by the addition of an equal volume (50 μL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 μL per wash).
12. Allowed to dry under vacuum for 2–3 minutes.
13. Dryed in hood for ~20 minutes.
14. Assembled Wallac Millipore adapter and added 50 μL of scintillant to each well and counted.

IV. FLT-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:

1. Dilute inhibitors (account for the final dilution into the assay, 1:20)
2. Prepare the appropriate amount of reaction mix at room temperature.
   10× Buffer (20 mM Tris pH 7.4/0.1 M NaCl/1 mM DTT final)
   0.1M $MnCl_2$ (5 mM final)
   pEY substrate (75 μg/mL)
   ATP/[$^{33}$P]ATP (0.5 μM/L μCi final)
   BSA (500 μg/mL final)
3. Add 5 μL of the diluted inhibitor to the reaction mix. (Final volume of 5 μL in 50% DMSO). Positive control wells—add blank DMSO (50%).
4. Add 35 μL of the reaction mix to each well of a 96 well plate.
5. Dilute enzyme into enzyme dilution buffer (keep at 4° C.).
6. Add 10 μL of the diluted enzyme to each well and mix (5–10 nM final). Negative control wells—add 10 μL 0.5 M EDTA per well instead (final 100 mM)
7. Incubate at room temperature for 60 min.
8. Stop by the addition of an equal volume (50 μL) of 30% TCA/0.1M Na pyrophosphate.
9. Incubate for 15 min to allow precipitation.
10. Transfer to Millipore filter plate.
11. Wash 3× with 15% TCA/0.1M Na pyrophosphate (125 μL per wash).
12. Allow to dry under vacuum for 2–3 min.
13. Dry in hood for ~20 min.
14. Assemble Wallac Millipore adapter and add 50 μL of scintillant to each well and count.

EXAMPLES

Examples provided are intended to assist in a further understanding of the invention. Particular materials employed, species and conditions are intended to be further illustrative of the invention and not limiting of the reasonable scope thereof.

SCHEME 1

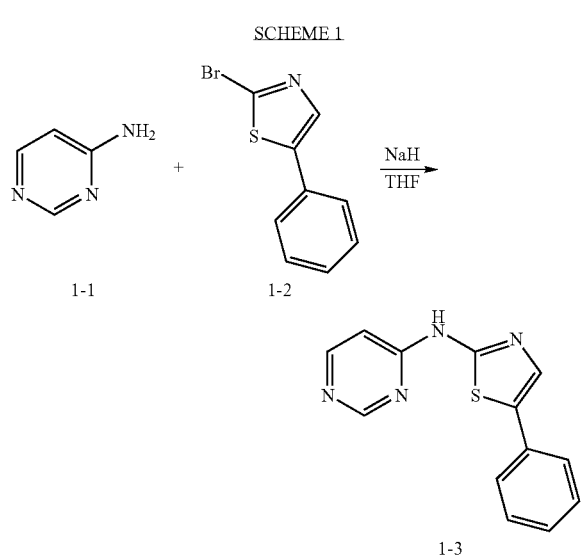

(5-Phenyl-thiazol-2-yl)-pyrimidin-4-yl-amine (1-3)

4-aminopyrimidine (30 mg, 0.32 mmol) was dissolved in 1 mL anhydrous THF in a flame dried flask under Ar. Sodium hydride (6 mg, 60% dispersion, 0.2 mmol) was then added to the flask at room temperature. When the bubbling stopped, 2-bromo-5-phenylthiazole (50 mg, 0.21 mmol) was added and the reaction was heated to reflux overnight. The solvent was removed under reduced pressure, water was added, and the resulting precipitate filtered. The compound was then dissolved in DMSO, purified by reverse phase preparative HPLC (C18), free-based with NaHCO$_3$ (aq.), extracted with 3×DCM, and concentrated. $^1$H-NMR (300 MHz, DMSO-d$_6$) 8.87 (1H, s), 8.47 (1H, d, J=5.6), 7.88 (1H, s), 7.63 (2H, d, J=7.1), 7.42 (2H, t, J=7.8), 7.29 (1H, t, J=7.6), 7.07 (1H, d, J=6.1). MS M+1=255.3. MP>250° C.

The following compounds were prepared in the same manner.

(5-Phenyl-thiazol-2-yl)-[2-methyl-5-methylaminoacetyl-pyrimidin-4-yl]amine (1-4)

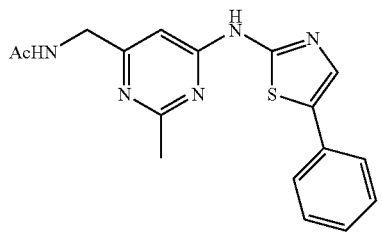

(4-Amino-2-2methyl-5-pyrimidinylmethyl)-N-acetimide (50 mg, 0.3 mmol) was suspended in dry dimethylforamide and sodium hydride (44.0 mg of 60%, 1.1 mmol) was added. After the effervescence had subsided 2-chloro-5-phenylthiazole was added. The reaction was heated at 60° C. for two hours. The dimethylforamide was removed under high vac. And the residue dissolved in methanol (4.0 mL)/water (0.5 mL)/trifluoroacetic acid (0.25 mL). This mixture was then purified by reverse phase preparative HPLC (C18) to give the above compound as its TFA salt. $^1$H-NMR (400 MHz, CD$_3$OD) 8.06 (1H, br-s), 7.87 (1H, br-s), 7.68 (1H, br-s), 7.66 (1H, br-s), 7.47 (2H, m), 4.43 (2H, s), 2.74 (3H, s), 2.03 (3H, s). MS(M+1)=340.

(5-Phenyl-thiazol-2-yl)-[2,6-dimethyl-pyrimidin-4-yl]amine (1-5)

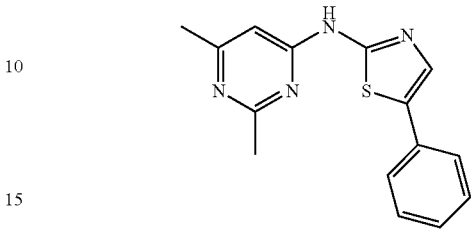

Prepared by the same method as 1-4 to provide the title compound as its TFA salt. $^1$H-NMR (400 MHz NMR, DMSO-d$_6$), 7.80 (1H, s), 7.61 (2H, d), 7.43 (2H, m), 7.34 (1H, m), 6.47 (1H, br-s), 2.78 (3H, s), 2.54 (3H, s). MS(M+1)=283

SCHEME 2
2-[(2-aminopyrimidin-4-yl)amino]-1,3-thiazole-5-carbonitrile (2-3)

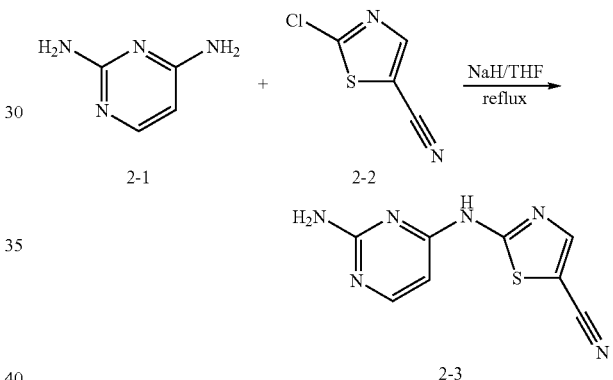

2-[(2-aminopyrimidin-4-yl)amino]-1,3-thiazole-5-carbonitrile (2-3)

2,4-Diaminopyrimidine, 2-1, (0.1 g, 0.908 mmol) was dissolved in DMF and then sodium hydride (0.036 g of a 60% dispersion, 0.908 mmol) was added and stirred for 15 minutes at 25° C. and then 2-chloro-1,3-thiazole-5-carbonitrile, 2-2, (0.131 g, 0.908 mmol) was added. This was heated at 100° C. for 2 hours. After this time the reaction was diluted with 4 mL of methanol and loaded onto a C$_{18}$ prep 1c column. The product, 2-3, was isolated via lyophilization from dioxane.

$^1$H-NMR (DMSO): 8.42 ppm (s, 1H); 8.10 ppm (d, 1H); 6.45 ppm (d, 1H).

SCHEME 3
2-[(6-aminopyrimidin-4-yl)amino]-1,3-thiazole-5-carbonitrile(3-2)

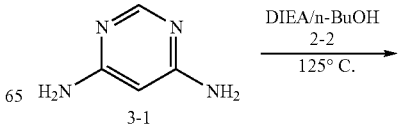

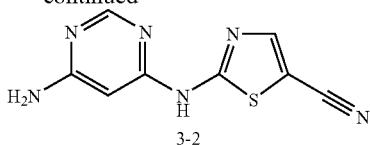

4,6-diaminopyrimidine hemisulfate, hemisulfate of 3-1, (0.10 g, 0.314 mmol) and diisopropylethylamine (0.122 g, 0.942 mmol) were suspended in n-butanol (1 mL) and then solid 2-chloro-1,3-thiazole-5-carbonitrile 2-2 (0.091 g, 0.628 mmol) was added and heated at 125° C. for 18 hours. The product 3-2 was purified on C18 preparative hplc and the product was isolated upon evaporation. Hi-Res MS: calc: 219.0448 found: 219.0448. $^1$H-NMR (DMSO): 8.36 ppm (s, 1H); 8.26 ppm (s, 1H); 7.20 ppm (s, 1H); 6.12 pm (s, 1H).

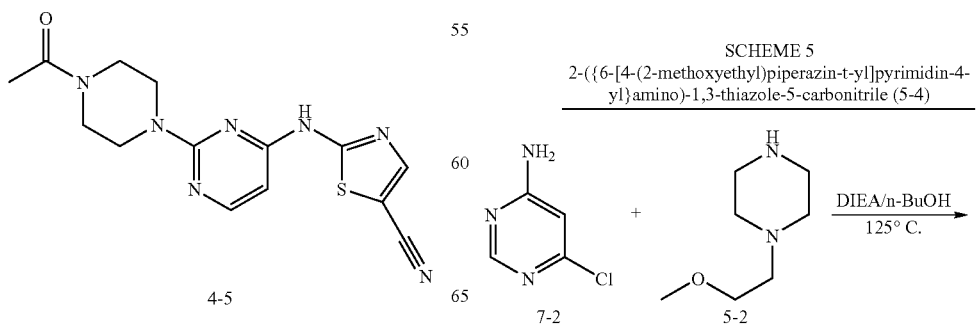

2-(4-acetylpiperazin-1-yl)-6-chloropyrimidin-4-amine (4-3)

2,4-dichloro-6-arinopyrimidine 4-1 (0.5 g, 3.05 mmol) and triethylamine (0.617 g, 6.10 mmol) were dissolved in DMF and then 1-acetylpiperazine 4-2 (0.391 g, 3.10 mmol) was added as a solid and stirred for 2 hours. A precipitate was filtered off and discarded. The DMF was then evaporated off and to the residue was added ethyl acetate and DCM. The product was purified on silica gel (DCM:MeOH:NH$_4$OH 98:2:0.2) which separated the two regioisomers. The desired product was the major product. $^1$H-NMR (CD$_3$OD): 5.83 ppm (s, 1H); 3.79 ppm (m, 2H); 3.72 ppm (m, 2H); 3.60 ppm (m, 2H); 3.57 ppm (m, 2H); 2.14 ppm (s, 3H).

2-(4-acetylpiperazin-1-yl)pyrimidin-4-amine (4-4)

2-(4-acetylpiperazin-1-yl)-6-chloropyrimidin-4-amine 4-3 (0.90 g, 3.52 mmol) was dissolved in 95% ethanol and then evacuated and back flushed with nitrogen before introducing 10% Pd/C (0.50 g). A hydrogen atmosphere was introduced and this suspension was stirred for 2.5 hours. The catalyst was then filtered off and the filtrate was evaporated to a solid. The solid was purified on a silica column (DCM:MeOH:NH$_4$OH 95:5:0.5) and the product 4-4 was isolated upon evaporation. $^1$H-NMR(DMSO): 7.75 ppm (d, 1H); 6.44 ppm (s, 2H); 5.74 ppm (d, 1H); 3.66 ppm (m, 2H); 3.59 ppm (m, 2H); 3.45 ppm (m, 4H); 2.03 ppm (s, 3H).

2-{[2-(4-acetylpiperazin-1-yl)pyrimidin-4-yl]amino}-1,3-thiazole-5-carbonitrile (4-5)

2-(4-acetylpiperazin-1-yl)pyrimidin-4-amine 4-4 (0.1 g, 0.45 mmol) was dissolved in dry TBF and then 1 equivalent of sodium hydride (0.036 g, 0.45 mmol) was added and this was stirred for 20 minutes at 25° C. then 2-chloro-1,3-thiazole-5-carbonitrile 2-2 (0.065 g, 0.45 mmol) was added followed immediately by 1 more equivalent of sodium hydride. The reaction was then stirred at 100° C. for 3 hours. The reaction was cooled to 25° C. and methanol was added. This solution was loaded directly onto a silica column and eluted with DCM:MeOH:NH$_4$OH (95:5:0.5). Fractions were combined and evaporated to yield the product, 4-5. Hi-Res MS: calc: 330.1132 found: 330.1137. $^1$H-NMR (DMSO): 8.33 ppm (s, 1H); 8.19 ppm (d, 1H); 6.34 ppm (d, 1H); 3.88 ppm (m, 2H); 3.80 ppm (m, 2H); 3.57 ppm (m, 4H); 2.07 ppm (s, 3H).

SCHEME 5
2-({6-[4-(2-methoxyethyl)piperazin-t-yl]pyrimidin-4-yl}amino)-1,3-thiazole-5-carbonitrile (5-4)

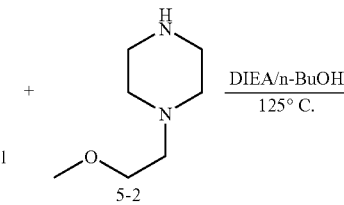

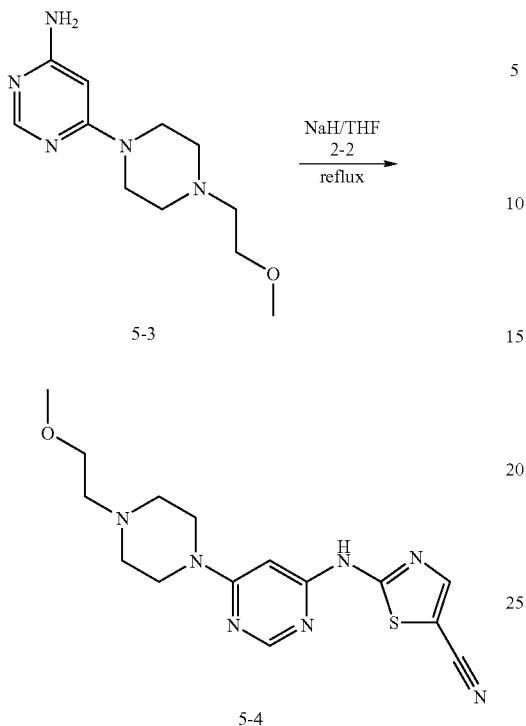

6-[4-(2-methoxyethyl)piperazin-1-yl]pyrimidin-4-amine (5-3)

6-Chloropyrimidin-4-amine 7-2 (0.3 g, 2.32 mmol) and diisopropylethylamine (0.30 g, 2.32 mmol) were suspended in n-butanol and then 1-(2-methoxyethyl)piperazine 5-2 (0.334 g, 2.32 mmol) was added. The reaction was stirred at 125° C. for 18 hours. The butanol was removed under reduced pressure, diluted with DCM and loaded onto a silica column eluted with DCM (100 mL), DCM:MeOH (99:4) and then DCM:MeOH:NH$_4$OH (9:1:0.1). The product 5-3 was isolated after evaporation. $^1$H-NMR (DMSO): 7.95 ppm (s, 1H); 6.23 ppm (s, 2H); 5.59 ppm (s, 1H); 3.43 ppm (m, 4H); 3.33 ppm (m, 2H); 3.25 ppm (s, 3H); 2.59 ppm (m, 2H); 2.54 ppm (m, 4H).

2-({6-[4-(2-methoxyethyl)piperazin-1-yl]pyrimidin-4-yl}amino)-1,3-thiazole-5-carbonitrile (5-4)

6-[4-(2-methoxyethyl)piperazin-1-yl]pyrimidin-4-amine 5-3 (0.25 g, 1.05 mmol), sodium hydride (0.842 g, 2.11 mmol), and 2-chloro-1,3-thiazole-5-carbonitrile 2-2 (0.15 g, 1.05 mmol) were treated as in Scheme 4 above. The product 5-4 was purified on a C$_{18}$ preparative hplc and isolated via lyophilization from dioxane. Hi-Res MS: calc: 346.1445 found: 346.1445. $^1$H-NMR (DMSO): 9.97 ppm (s, 1H); 8.51 ppm (s, 1H); 8.28 ppm (s, 1H); 6.32 ppm (s, 1H); 4.35 ppm (m, 2H); 3.68 ppm (m, 2H); 3.59 ppm (m, 2H); 3.37 ppm (m, 7H); 3.12 ppm (m, 2H).

SCHEME 6
2-({6-[bis(2-methoxyethyl)amino]pyrimidin-4-yl}amino)-1,3-thiazole-5-carbonitrile (6-3)

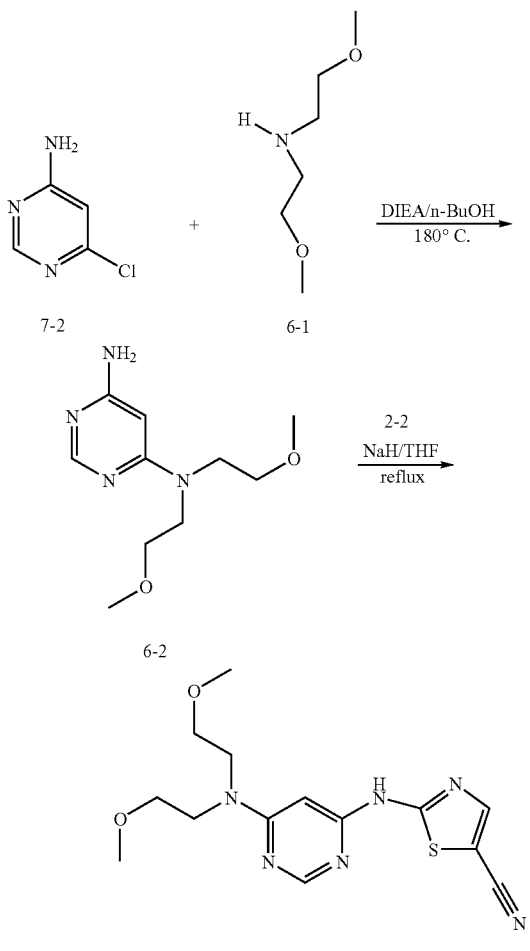

N,N-bis(2-methoxyethyl)pyrimidine-4,6-diamine (6-2)

6-Chloropyrimidin-4-amine 7-2 (0.3 g, 2.32 mmol) and diisopropylethylamine (0.30 g, 2.32 mmol) were suspended in n-butanol and then 2-methoxy-N-(2-methoxyethyl)ethanamine 6-1 (0.31 g, 2.32 mmol) was added. The reaction was stirred at 180° C. for 24 hours. The solvent was removed under reduced pressure and the product 6-2 was purified on a silica column. $^1$H-NMR (DMSO): 7.91 ppm (s, 1H); 6.10 ppm (2H); 5.51 ppm (s, 1H); 3.45 ppm (m, 4H); 3.45 ppm (m, 4H); 3.25 ppm (s, 6H).

2-({6-[bis(2-methoxyethyl)amino]pyrimidin-4-yl}amino)-1,3-thiazole-5-carbonitrile (6-3)

N,N-bis(2-methoxyethyl)pyrimidine-4,6-diamine 6-2 (0.13 g, 0.58 mmol), sodium hydride (0.046 g, 1.16 mmol) and 2-chloro-1,3-thiazole-5-carbonitrile 2-2 (0.083 g, 0.58 mmol) were treated as in Scheme 4 above. The product 6-3 was purified on a C$_{18}$ preparative hplc column and isolated via lyophilization. Hi-Res MS: calc: 335.1285 found:

335.1282. $^1$H-NMR (DMSO): 8.39 ppm (s, 1H); 8.24 ppm (s, 1H); 6.22 ppm (s, 1H); 3.65 ppm (m, 4H); 3.51 ppm (m, 4H); 3.26 ppm (s, 6H).

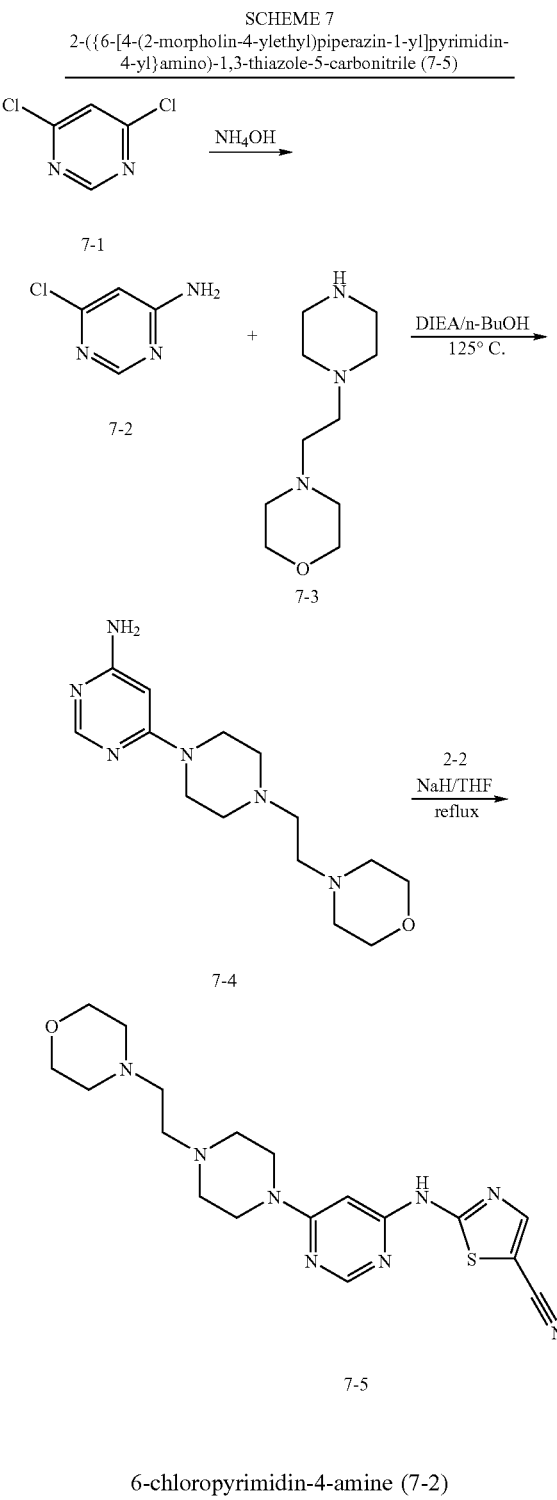

6-chloropyrimidin-4-amine (7-2)

4,6-Dichloropyrimidine 7-1 (6.5 g, 43.6 mmol), ammonium hydroxide (30 mL) and n-butanol (15 mL) were placed in a sealed tube and stirred at 90° C. for 2.5 hours. After this time the reaction was cooled to room temperature, the solid was filtered off, washed with ethyl ether and dried to yield 7-2. $^1$H-NMR (DMSO): 8.20 ppm (s, 1H); 7.24 ppm (s, 2H); 6.44 ppm (s, 1H).

6-[4-(2-morpholin-4-ylethyl)piperazin-1-yl]pyrimidin-4-amine (7-4)

6-chloropyrimidin-4-amine 7-2 (3.09 g, 23.9 mmol) and diisopropylethylamine (3.08 g, 23.9 mmol) were suspended in n-butanol and then 4-(2-piperazin-1-ylethyl)morpholine 7-3 (4.75 g, 23.9 mmol) was added. The reaction was stirred at 125° C. for 18 hours and then the product was filtered off, washed with n-butanol and ethyl ether and then air dried. Hi-Res MS: calc: 293.2084 found: 293.2078. $^1$H-NMR (DMSO): 7.94 ppm (s, 1H); 6.18 ppm (s, 2H); 5.57 ppm (s, 1H); 3.56 ppm (m, 6H); 3.39 ppm (m, 8H); 2.47 ppm (m, 6H).

2-({6-[4-(2-morpholin-4-ylethyl)piperazin-1-yl]pyrimidin-4-yl}amino)-1,3-thiazole-5-carbonitrile (7-5)

6-[4-(2-morpholin-4-ylethyl)piperazin-1-yl]pyrimidin-4-amine 7-4 (1.5 g, 5.13 mmol), sodium hydride (0.41 g, 10.26 mmol) and 2-chloro-1,3-thiazole-5-carbonitrile 2-2 (0.74 g, 5.13 mmol) were treated as in Scheme 4 above. The product was purified on a silica column eluted with DCM:MeOH:NH$_4$OH (95:5:0.5 and 9:1:0.1) and isolated directly from the appropriate fractions after they were concentrated and the residue was suspended in methanol and filtered. $^1$H-NMR (CDCl$_3$): 9.27 ppm (s, 1H); 8.45 ppm (s, 1H); 7.90 ppm (s, 1H); 5.87 ppm (s, 1H); 3.72 ppm (m, 4H); 3.65 ppm (s, 4H); 2.57 ppm (m, 8H); 2.50 ppm (s, 4H).

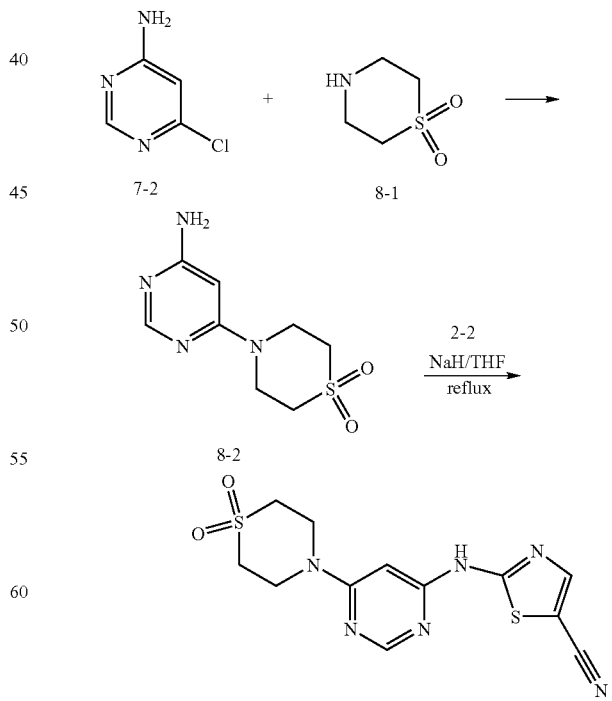

6-(1,1-Dioxidothiomorpholin-4-yl)pyrimidin-4-amine (8-2)

6-Chloropyrimidin-4-amine 7-2 (0.4 g, 3.09 mmol) and diisopropylethylamine (0.4 g, 3.09 mmol) were suspended in n-butanol and thiomorpholine 1,1-dioxide (0.417 g, 3.09 mmol) was added. The reaction was stirred at 200° C. for 18 hours, the butanol was evaporated off and the product was purified on a silica column eluted with DCM:MeOH: NH$_4$OH (95:5:0.5). Yield=2.45 mmol (79%). $^1$H-NMR (CD$_3$OD): 8.03 ppm (s, 1H); 5.87 ppm (s, 1H); 4.10 ppm (t, 4H); 3.09 ppm (t, 4H).

2-{[6-(1,1-Dioxidothiomorpholin-4-yl)pyrimidin-4-yl]amino}-1,3-thiazole-5-carbonitrile (8-3)

6-(1,1-Dioxidothiomorpholin-4-yl)pyrimidin-4-amine 8-2 (0.237 g, 1.04 mmol), sodium hydride (0.083 g, 2.08 mmol) and 2-chloro-1,3-thiazole-5-carbonitrile 2-2 (0.15 g, 1.04 mmol) were treated as in Scheme 4 above. The product was purified on a preparative hplc column and isolated via lyophilization to yield 8-3. Hi-Res MS: calc: 337.0536 found: 337.0530. $^1$NMR(DMSO): 8.51 ppm (s, 1H); 8.27 ppm (s, 1H); 6.36 ppm (s, 1H); 4.05 ppm (s, 4H); 3.21 ppm (s, 4H).

SCHEME 9
2-{[6-(3-Aminopiperidin-1-yl)pyrimidin-4-yl]amino}-1,3-thiazole-5-carbonitrile (9-6)

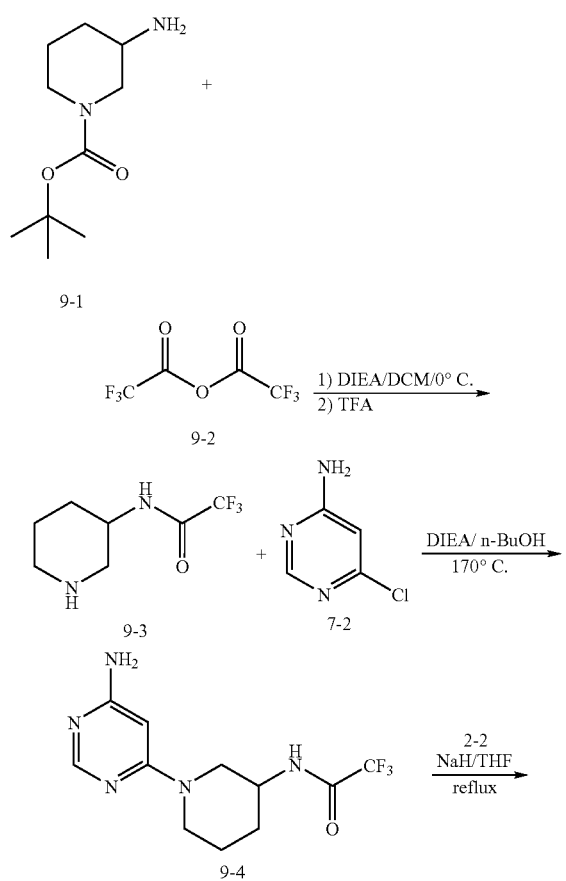

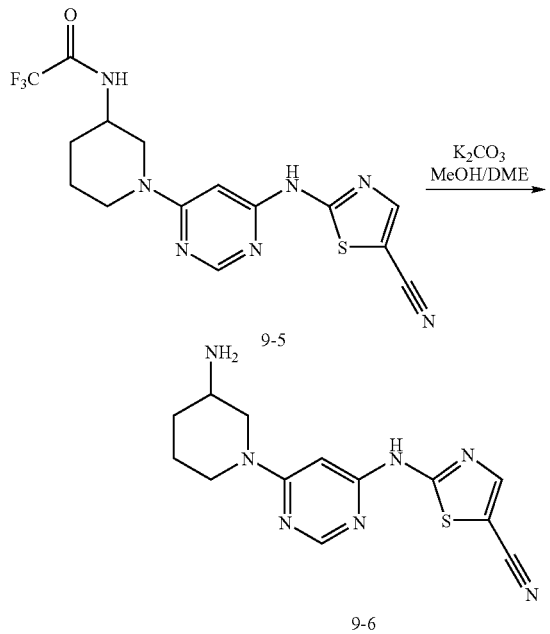

2,2,2-Trifluoro-N-piperidin-3-ylacetamide (9-3)

(+/−)-Tert-butyl 3-aminopiperidine-1-carboxylate 9-1 (0.54 g, 2.7 mmol) and DIEA (0.348 g, 2.70 mmol) were dissolved in 3 mL dichloromethane and cooled to 0° C. A dichloromethane solution (2 mL) of trifluoroacetic anhydride (0.566 g, 2.70 mmol) was slowly added and stirred for 15 minutes and then the ice bath was removed and the reaction was stirred at 25° C. for 1 hour. When the reaction is complete it is partitioned with water. The dichloromethane layer is drawn off, dried and evaporated to afford 9-3. Hi Res MS: calc: 297.1421 found: 297.1421. A portion of this material was then treated with neat trifluoroacetic acid and the desired compound was isolated via evaporation.

N-[1-(6-aminopyrimidin-4-yl)piperidin-3-yl]-2,2,2-trifluoroacetamide (9-4)

6-Chloropyrimidin-4-amine 7-2 (0.149 g, 1.15 mmol) and diisopropylethylamine (0.446 g, 3.45 mmol) were suspended in n-butanol. 2,2,2-Trifluoro-N-piperidin-3-ylacetamide 9-3 (0.226 g, 1.15 mmol) was then added. The reaction was stirred at 170° C. for 24 hours. The butanol was then removed under reduced pressure and the product was purified on a silica column eluted with DCM:MeOH:NH$_4$OH (95:5:0.5). $^1$H-NMR (CD$_3$OD): 8.06 ppm (s, 1H); 5.82 ppm (s, 1H); 4.27 ppm (d, 1H); 4.15 ppm (d, 1H); 3.85 ppm (m, 1H); 3.73 ppm (p, 3H); 3.23 ppm (q, 3H); 3.08 ppm (dd, 2H); 2.13 ppm (m, 1H); 1.85 ppm (m, 1H); 1.71 ppm (m, 1H); 1.62 ppm (m, 1H).

N-(1-{6-[(5-cyano-1,3-thiazol-2-yl)amino]pyrimidin-4-yl}piperidin-3-yl)-2,2,2-trifluoroacetamide (9-5)

N-[1-(6-aminopyrimidin-4-yl)piperidin-3-yl]-2,2,2-trifluoroacetamide 9-4 (0.26 g, 0.9 mmol), sodium hydride (0.144 g, 3.6 mmol) and 2-chloro-1,3-thiazole-5-carbonitrile 2-2 (0.13 g, 0.9 mmol) were treated as in Scheme 4 above. When the reaction was complete it was quenched with 5 equivalents of concentrated HCl (370 µL). The solution was then diluted with ethyl acetate, water and some dilute NaHCO$_3$. The aqueous layer was removed and the organic layer dried, filtered and evaporated to dryness under reduced pressure. Trituration with ethyl ether produced 9-5 as a solid, which was used without further purification in the next step.

2-{[6-(3-Aminopiperidin-1-yl)pyrimidin-4-yl]amino}-1,3-thiazole-5-carbonitrile (9-6)

Crude N-(1-{6-[(5-cyano-1,3-thiazol-2-yl)amino]pyrimidin-4-yl}piperidin-3-yl)-2,2,2-trifluoroacetamide 9-5 (0.9 mmol) was suspended/dissolved in methanol/dimethoxyether (5 mL/2 mL) and potassium carbonate (1.8 mmol). This was warmed to 75° C. and stirred overnight. The product was purified on a preparative hplc and isolated via lyophilization from dioxane/water to produce 9-6. Hi-Res MS: calc: 302.1183 found: 302.1190. $^1$NMR(CD$_3$OD): 8.31 ppm (s, 1H); 7.87 ppm (s, 1H); 6.09 ppm (s, 1H); 4.21 ppm (d, 1H); 4.07 ppm (d, 1H); 3.60 ppm (m, 1H); 2.95 ppm (m, 1H); 2.75 ppm (m, 1H); 2.00 ppm (m, 1H); 1.77 ppm (m, 1H); 1.54 ppm (m, 1H); 1.37 ppm (m, 1H).

SCHEME 10
2-({6-[4-(3-morpholin-4-ylpropyl)piperazin-1-yl]pyrimidin-4-yl}amino)-1,3-thiazole-5-carbonitrile (10-3)

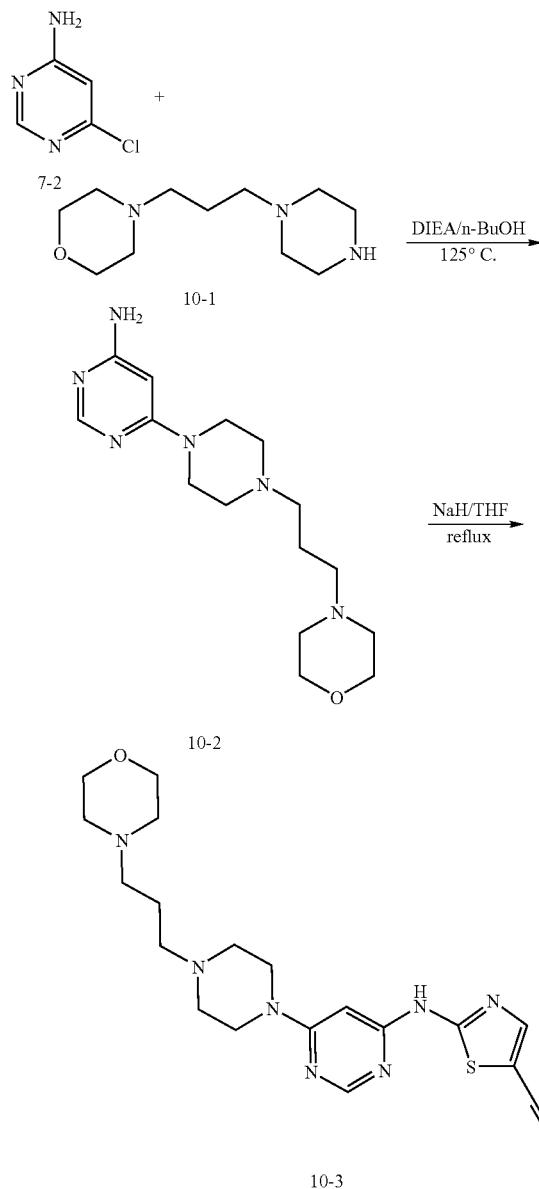

6-[4-(3-Morpholin-4-ylpropyl)piperazin-1-yl]pyrimidin-4-amine (10-2)

6-Chloropyrimidin-4-amine 7-2 (0.368 g, 2.84 mmol) and diisopropylethylamine (0.367 g, 2.84 mmol) were suspended in n-butanol. 4-(3-piperazin-1-ylpropyl)morpholine 10-1 (0.61 g, 2.84 mmol) was then added. The reaction was stirred at 125° C. for 18 hours. Upon cooling the resulting solid was filtered off, washed with ethyl ether and dried to afford 10-2. $^1$NMR (DMSO): 7.94 ppm (s, 1H); 6.18 ppm (s, 2H); 5.58 ppm (s, 1H); 3.56 ppm (t, 4H); 3.39 ppm (t, 4H); 2.38 ppm (t, 4H); 2.31 ppm (m, 8H); 1.60 ppm (p, 2H).

2-({6-[4-(3-morpholin-4-ylpropyl)piperazin-1-yl]pyrimidin-4-yl}amino)-1,3-thiazole-5-carbonitrile (10-3)

6-[4-(3-Morpholin-4-ylpropyl)piperazin-1-yl]pyrimidin-4-amine 10-2 (0.317 g, 1.04 mmol), sodium hydride (0.083 g, 2.08 mmol) and 2-chloro-1,3-thiazole-5-carbonitrile 2-2 (0.15 g, 1.04 mmol) were treated as in Scheme 4 above. The product was purified on a C$_{18}$ preparative column and isolated via lyophilization. Hi-Res MS: calc: 415.2023 found: 415.2030. $^1$NMR (CD$_3$OD): 8.48 ppm (s, 1H); 8.02 ppm (s, 1H); 6.27 ppm (s, 1H); 3.94 ppm (m, 6H); 3.43–3.27 ppm (m, 14H); 2.29 ppm (m, 2H).

SCHEME 11
2-({6-[4-(2-Pyrrolidin-1-ylethyl)piperazin-1-yl]pyrimidin-4-yl}amino)-1,3-thiazole-5-carbonitrile (11-3)

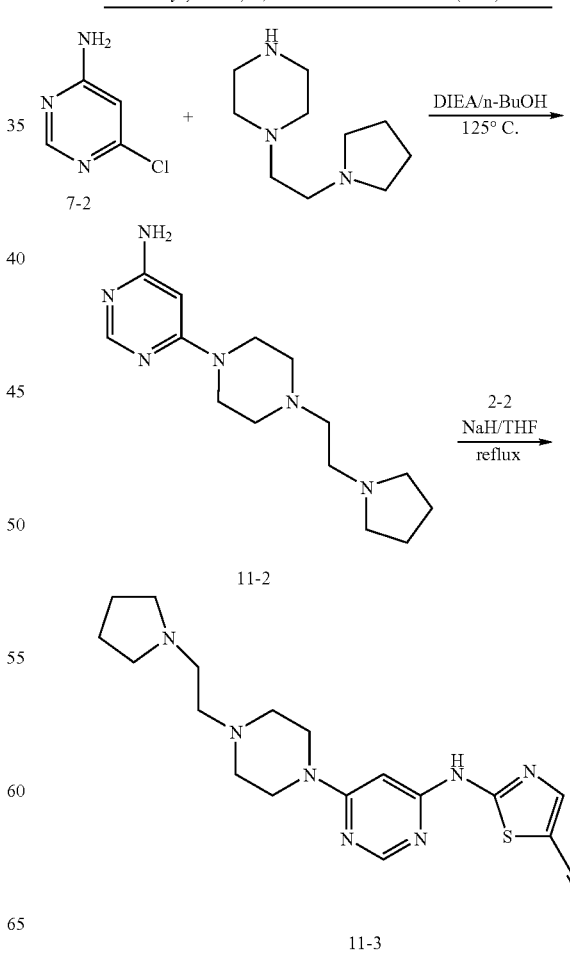

6-[4-(2-Pyrrolidin-1-ylethyl)piperazin-1-yl]pyrimidin-4-amine (11-2)

6-Chloropyrimidin-4-amine 7-2 (0.317 g, 2.44 mmol) and diisopropylethylamine (0.0.316 g, 2.44 mmol) were suspended in n-butanol and 1-(2-pyrrolidin-1-ylethyl)piperazine 11-1 (0.448 g, 2.44 mmol) was added. The reaction was stirred at 125° C. for 18 hours. Upon cooling the reaction was purified on a silica column (DCM:MeOH:NH$_4$OH) to afford 11-2. $^1$NMR (CD$_3$OD): 7.96 ppm (s, 1H); 5.71 ppm (s, 1H); 3.53 ppm (t, 4H); 2.69 ppm (m, 2H); 2.58 ppm (m, 10H); 1.82 ppm (m, 4H).

2-({6-[4-(2-pyrrolidin-1-ylethyl)piperazin-1-yl]pyrimidin-4-yl}amino)-1,3-thiazole-5-carbonitrile (11-3)

6-[4-(2-Pyrrolidin-1-ylethyl)piperazin-1-yl]pyrimidin-4-amine 11-2 (0.35 g, 1.27 mmol), sodium hydride (0.101 g, 2.53 mmol) and 2-chloro-1,3-thiazole-5-carbonitrile 2-2 (0.183 g, 1.27 mmol) were treated as in Scheme 4 above. The product was purified on a C$_{18}$ preparative column and isolated via lyophilization. Hi-Res MS: calc: 385.1921 found: 385.1918. $^1$NMR (DMSO): 12.1 ppm (s, 1H); 8.46 ppm (s, 1H); 8.27 ppm (s, 1H); 6.27 ppm (s, 1H); 3.63 ppm (m, 6H); 3.35 ppm (m, 4H); 2.76 ppm (m, 6H); 1.96 ppm (s, 4H).

SCHEME 12
2-({6-[4-(2-Morpholin-4-yl-2-oxoethyl)piperazin-1-yl]pyrimidin-4-yl}amino)-1,3-thiazole-5-carbonitrile (12-5)

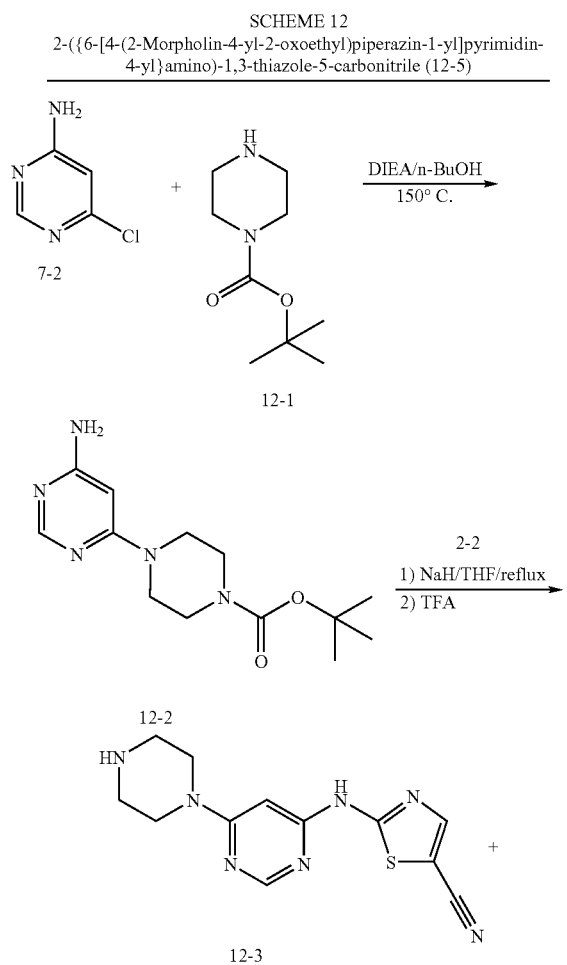

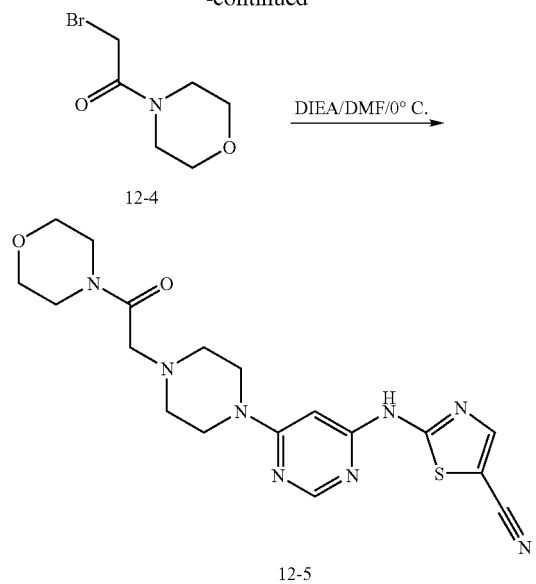

Tert-butyl 4-(6-aminopyrimidin-4-yl)piperazine-1-carboxylate (12-2)

6-Chloropyrimidin-4-amine 7-2 (0.4 g, 3.09 mmol) and diisopropylethylamine (0.40 g, 3.09 mmol) were suspended in n-butanol. tert-Butyl 4-(6-aminopyrimidin-4-yl)piperazine-1-carboxylate 12-1 (0.575 g, 3.09 mmol) was added. The reaction was stirred at 150° C. for 18 hours and then the product was filtered off, washed with n-butanol and ethyl ether, and then air dried. $^1$H-NMR (CD$_3$OD): 7.98 ppm (s, 1H); 5.72 ppm (d, 1H); 3.54 ppm (m, 4H); 3.52 ppm (m, 4H); 1.48 ppm (s, 9H).

2-[(6-Piperazin-1-ylpyrimidin-4-yl)amino]-1,3-thiazole-5-carbonitrile (12-3)

Tert-butyl 4-(6-aminopyrimidin-4-yl)piperazine-1-carboxylate 12-2 (0.25 g, 0.9 mmol), sodium hydride (0.072 g, 1.8 mmol) and 2-chloro-1,3-thiazole-5-carbonitrile 2-2 (0.129 g, 0.9 mmol) were treated as in Scheme 4 above. The product was purified on a C$_{18}$ preparative column and evaporated to dryness. The residue was then treated with trifluoroacetic acid and the product was isolated from a sodium carbonate/methyene chloride partition. $^1$H-NMR (CD$_3$OD): 8.47 ppm (s, 1H); 8.02 ppm (s, 1H); 6.24 ppm (s, 1H); 3.88 ppm (t, 4H); 3.27 ppm (t, 4H).

2-({6-[4-(2-Morpholin-4-yl-2-oxoethyl)piperazin-1-yl]pyrimidin-4-yl}amino)-1,3-thiazole-5-carbonitrile (12-5)

2-[(6-Piperazin-1-ylpyrimidin-4-yl)amino]-1,3-thiazole-5-carbonitrile 12-3 (0.10 g, 0.35 mmol) and diisopropylethylamine (0.049 g, 0.38 mmol) were dissolved in DMF. After cooling to 0° C., a DMF solution of 4-(bromoacetyl)morpholine 12-4 (0.08 g, 0.38 mmol) was added slowly via addition funnel. The product was purified on a C$_{18}$ preparative LC column and isolated via lyophilization. Hi-Res MS: calc: 415.1655 found: 415.1663. $^1$H-NMR (CD$_3$OD): 8.49 ppm (s, 1H); 8.03 ppm (s, 1H); 6.27 ppm (s, 1H); 4.34 ppm (s, 2H); 3.70 ppm (m, 4H); 3.65 ppm (m, 4H); 3.42 ppm (t, 2H); 3.33 ppm (m, 6H).

SCHEME 13
2-(4-{6-[(5-Cyano-1,3-thiazol-2-yl)amino]pyrimidin-4-yl}piperazin-1-yl)-N-isopropylacetamide (13-3)

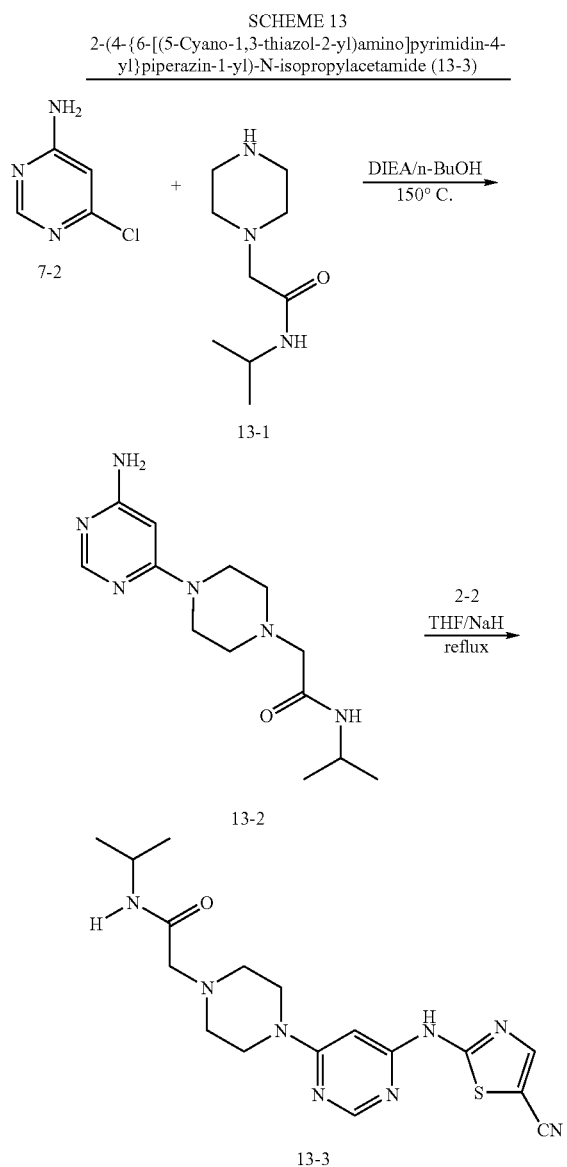

2-[4-(6-aminopyriridin-4-yl)piperazin-1-yl]-N-isopropylacetamide (13-2)

6-Chloropyrimidin-4-amine 7-2 (0.3 g, 2.32 mmol) and diisopropylethylamine (0.30 g, 2.32 mmol) were suspended in n-butanol. N-isopropyl-2-piperazin-1-ylacetamide 13-1 (0.429 g, 2.32 mmol) was then added. The reaction was stirred at 150° C. for 18 hours and then the product was filtered off, washed with n-butanol and ethyl ether and then air dried. $^1$H-NMR (CD$_3$OD): 7.96 ppm (s, 1H); 5.71 ppm (s, 1H); 4.03 ppm (m, 1H); 3.57 ppm (t, 4H); 3.02 ppm (s, 2H); 2.56 ppm (t, 4H); 1.16 ppm (d, 6H).

2-(4-{6-[(5-cyano-1,3-thiazol-2-yl)amino]pyrimidin-4-yl}piperazin-1-yl)-N-isopropylacetamide (13-3)

2-[4-(6-aminopyrimidin-4-yl)piperazin-1-yl]-N-isopropylacetamide 13-2 (0.45 g, 1.62 mmol), sodium hydride (0.13 g, 3.25 mmol) and 2-chloro-1,3-thiazole-5-carbonitrile 2-2 (0.235 g, 1.62 mmol) were treated as in Scheme 4 above. The product was purified on a C$_{18}$ preparative column and isolated via lyophilization. Hi-Res MS: calc: 387.1710 found: 387.1691. $^1$NMR (DMSO): 8.51 ppm (s, 1H); 8.47 ppm (s, 1H); 8.28 ppm (s, 1H); 6.30 ppm (s, 1H); 4.35 ppm (m, 2H); 3.91 ppm (m, 4H); 3.39 ppm (m, 2H); 3.18 ppm (m, 2H); 1.11 ppm (d, 6H).

SCHEME 14
2-{[6-(3-Aminopyrrolidin-1-yl)pyrimidin-4-yl]amino}-1,3-thiazole-5-carbonitrile (14-3)

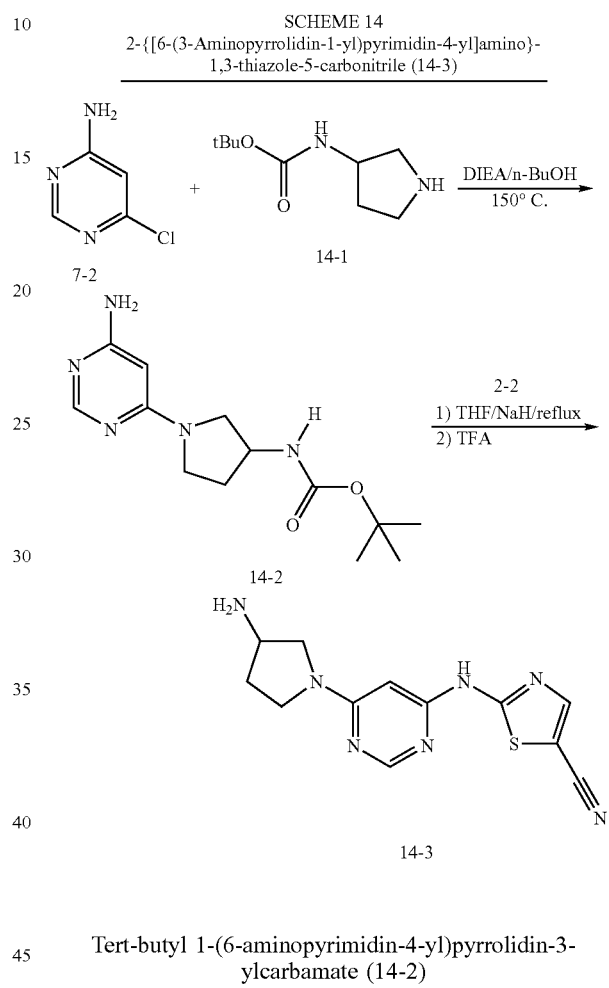

Tert-butyl 1-(6-aminopyrimidin-4-yl)pyrrolidin-3-ylcarbamate (14-2)

6-Chloropyrimidin-4-amine 7-2 (0.4 g, 3.09 mmol) and diisopropylethylamine (0.399 g, 3.09 mmol) were suspended in n-butanol. tert-Butyl 1-(6-aminopyrimidin-4-yl)pyrrolidin-3-ylcarbamate 14-1 (0.575 g, 3.09 mmol) was added. The reaction was stirred at 150° C. for 18 hours and then the product was filtered off, washed with n-butanol and ethyl ether and then air dried. $^1$H-NMR (CD$_3$OD): 7.92 ppm (s, 1H); 5.45 ppm (s, 1H); 4.19 ppm (t, 1H); 3.64 ppm (m, 1H); 3.51 ppm (m, 1H); 3.44 ppm (m, 1H); 3.24 ppm (m, 1H); 2.20 ppm (m, 1H); 1.93 ppm (m, 1H); 1.44 ppm (s, 9H).

2-{[6-(3-aminopyrrolidin-1-yl)pyrimidin-4-yl]amino}-1,3-thiazole-5-carbonitrile (14-3)

Tert-butyl 1-(6-aminopyrimidin-4-yl)pyrrolidin-3-ylcarbamate 14-2 (0.483 g, 1.73 mmol), sodium hydride (0.277 g, 6.92 mmol) and 2-chloro-1,3-thiazole-5-carbonitrile 2-2 (0.25 g, 1.73 mmol) were treated as in Scheme 4 above. The product was purified on a C$_{18}$ preparative column after treating the crude product with trifluoroacetic acid and then isolated via lyophilization. Hi-Res MS: calc: 288.1026 found: 288.1046. ¹NMR (CD₃OD): 8.43 ppm (s, 1H); 8.0 ppm (s, 1H); 6.02 ppm (s, 1H); 4.05 ppm (m, 1H); 3.87 ppm (m, 1H); 3.69 ppm (m, 3H); 2.51 ppm (m, 1H); 2.22 ppm (m, 1H).

ppm (s, 1H); 6.16 ppm (s, 1H); 4.08 ppm (m, 2H); 3.73 ppm (m, 2H); 3.40 ppm (m, 2H); 3.32 ppm (m, 2H); 2.21 ppm (m, 2H).

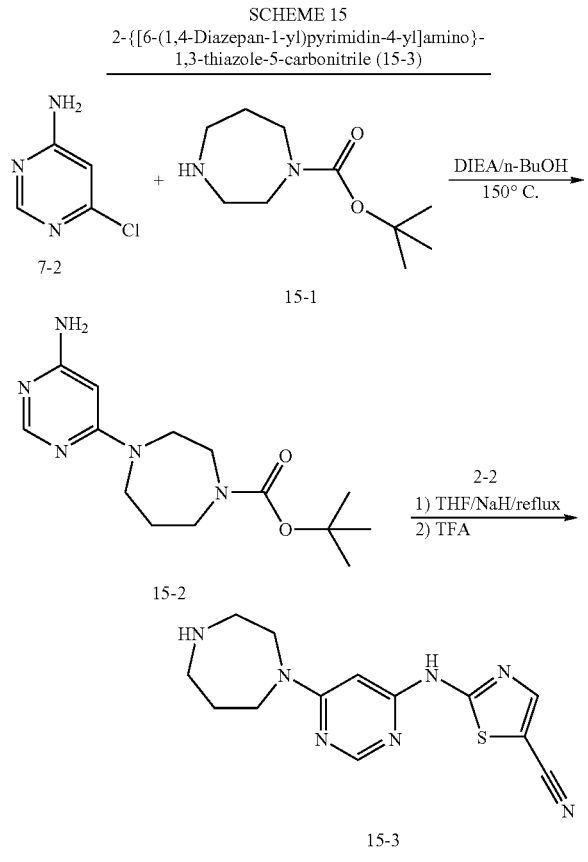

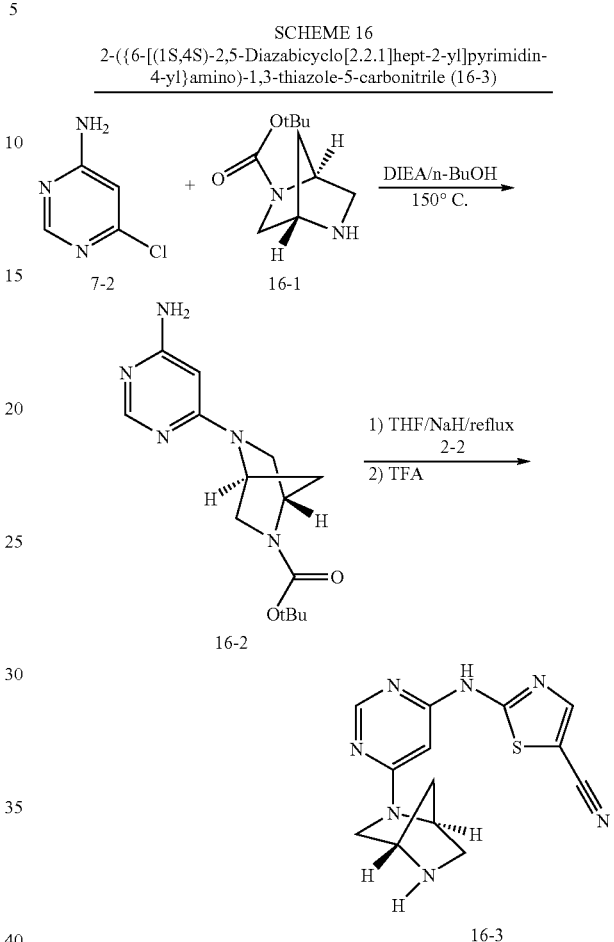

Tert-butyl 4-(6-aminopyrimidin-4-yl)-1,4-diazepane-1-carboxylate (15-2)

6-Chloropyrimidin-4-amine 7-2 (0.4 g, 3.09 mmol) and diisopropylethylamine (0.399 g, 3.09 mmol) were suspended in n-butanol. tert-Butyl 1,4-diazepane-1-carboxylate 15-1 (0.618 g, 3.09 mmol) was then added. The reaction was stirred at 150° C. for 18 hours and then the product was filtered off, washed with n-butanol and ethyl ether and then air dried. ¹H-NMR (CD₃OD): 7.95 ppm (s, 1H); 5.65 ppm (s, 1H); 3.73 ppm (m, 2H); 3.61 ppm (m, 3H); 3.55 ppm (t, 1H); 3.38 ppm (m, 1H); 3.34 ppm (m, 1H); 1.89 ppm (m, 1H); 1.84 ppm (m, 1H); 1.41 ppm (s, 4H); 1.36 ppm (s, 5H).

2-{[6-(1,4-diazepan-1-yl)pyrimidin-4-yl]amino}-1,3-thiazole-5-carbonitrile (15-3)

Tert-butyl 4-(6-aminopyrimidin-4-yl)-1,4-diazepane-1-carboxylate 15-2 (0.50 g, 1.70 mmol), sodium hydride (0.136 g, 3.4 mmol) and 2-chloro-1,3-thiazole-5-carbonitrile 2-2 (0.246 g, 1.70 mmol) were treated as in Scheme 4 above. The product was purified on a C₁₈ preparative column after treating the crude product with trifluoroacetic acid and then isolated via lyophilization. Hi-Res MS: calc: 302.1182 found: 302.1184. ¹NMR (CD₃OD): 8.45 ppm (s, 1H); 8.01

Tert-butyl (1S,4S)-5-(6-aminopyrimidin-4-yl)-2,5-diazabicyclo[2.2.1]heptane-2-carboxylate (16-2)

6-Chloropyrimidin-4-amine 7-2 (0.222 g, 1.71 mmol) and diisopropylethylamine (0.222 g, 1.71 mmol) were suspended in n-butanol. tert-Butyl (1S,4S)-2,5-diazabicyclo [2.2.1]heptane-2-carboxylate 16-1 (0.34 g, 1.71 mmol) was then added. The reaction was stirred at 150° C. for 18 hours and then the product was purified on a silica column. ¹H-NMR (DMSO): 7.91 ppm (s, 1H); 6.18 ppm (s, 2H); 5.33 ppm (s, 1H); 4.72 ppm (s, 1H); 4.41 ppm (d, 1H); 3.40 ppm (t, 1H); 3.27 ppm (m, 1H); 3.12 ppm (m, 2H); 1.86 ppm (m, 2H); 1.40 ppm (s, 4H); 1.36 ppm (s, 5H).

2-({6-[(1S,4S)-2,5-Diazabicyclo[2.2.1]hept-2-yl] pyrimidin-4-yl}amino)-1,3-thiazole-5-carbonitrile (16-3)

Tert-butyl (1S,4S)-5-(6-aminopyrimidin-4-yl)-2,5-diazabicyclo[2.2.1]heptane-2-carboxylate 16-2 (0.324 g, 1.11 mmol), sodium hydride (0.089 g, 2.22 mmol) and 2-chloro-1,3-thiazole-5-carbonitrile 2-2 (0.161 g, 1.11 mmol) were treated as in Scheme 4 above. The product was purified on a C₁₈ preparative column after treating the crude product with trifluoroacetic acid and then converted to a free base form after isolation via lyophilization. Hi-Res MS: calc: 300.1026 found: 300.1039. $^1$NMR (DMSO): 8.36 ppm (s, 1H); 8.23 ppm (s, 1H); 5.88 ppm (s, 1H); 4.90 ppm (s, 1H); 3.77 ppm (s, 1H); 3.41 ppm (s, 1H); 3.32 ppm (m, 2H); 2.93 ppm (d, 1H); 2.79 ppm (d, 1H); 1.78 ppm (m, 1H); 1.69 ppm (m, 1H).

SCHEME 17
2-({6-[4-(2-Oxo-2-pyrrolidin-1-ylethyl)piperazin-1-yl]pyrimidin-4-yl}amino)-1,3-thiazole-5-carbonitrile (17-3)

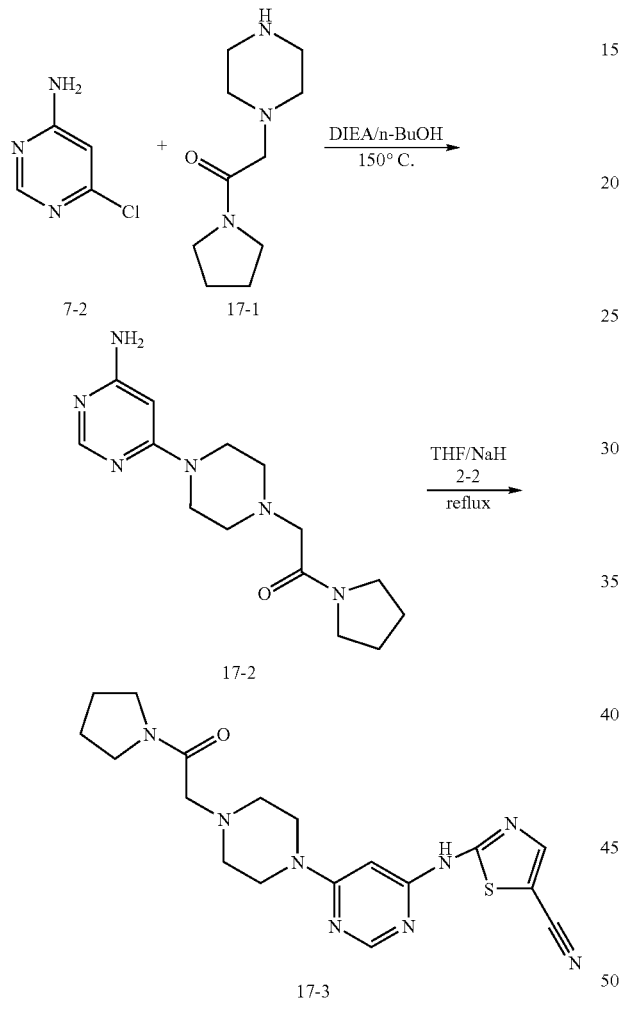

6-[4-(2-Oxo-2-pyrrolidin-1-ylethyl)piperazin-1-yl]pyrimidin-4-amine (17-2)

6-Chloropyrimidin-4-amine 7-2 (0.50 g, 3.86 mmol) and diisopropylethylamine (0.499 g, 3.86 mmol) were suspended in n-butanol and then 1-(2-oxo-2-pyrrolidin-1-yl-ethyl)piperazine 17-1 (0.762 g, 3.86 mmol) was added. The reaction was stirred at 150° C. for 18 hours and then the product was filtered off, washed with n-butanol and ethyl ether and air dried. $^1$H-NMR (CD$_3$OD): 7.96 ppm (s, 1H); 5.72 ppm (s, 1H); 3.55 ppm (m, 6H); 3.44 ppm (t, 2H); 3.24 ppm (s, 2H); 2.60 ppm (t, 2H); 1.98 ppm (m, 2H); 1.88 ppm (m, 2H).

2-({6-[4-(2-oxo-2-pyrrolidin-1-ylethyl)piperazin-1-yl]pyrimidin-4-yl}amino)-1,3-thiazole-5-carbonitrile (17-3)

6-[4-(2-Oxo-2-pyrrolidin-1-ylethyl)piperazin-1-yl]pyrimidin-4-amine 17-2 (0.60 g, 2.07 mmol) and sodium hydride (0.165 g, 4.13 mmol) and 2-chloro-1,3-thiazole-5-carbonitrile 2-2 (0.299 g, 2.07 mmol) were treated as in Scheme 4 above. The product was purified on a silica column. Hi-Res MS: calc: 399.1710 found: 399.1706. $^1$NMR (CDCl$_3$): 9.40 ppm (s, 1H); 8.45 ppm (s, 1H); 7.88 ppm (s, 1H); 5.98 ppm (s, 1H); 3.68 ppm (s, 4H); 3.50 ppm (m, 4H); 3.21 ppm (s, 2H); 2.68 ppm (t, 4H); 1.98 ppm (m, 2H); 1.87 ppm (m, 2H).

SCHEME 18
2-{[6-(4-aminopiperidin-1-yl)pyrimidin-4-yl]amino}-1,3-thiazole-5-carbonitrile (18-4)

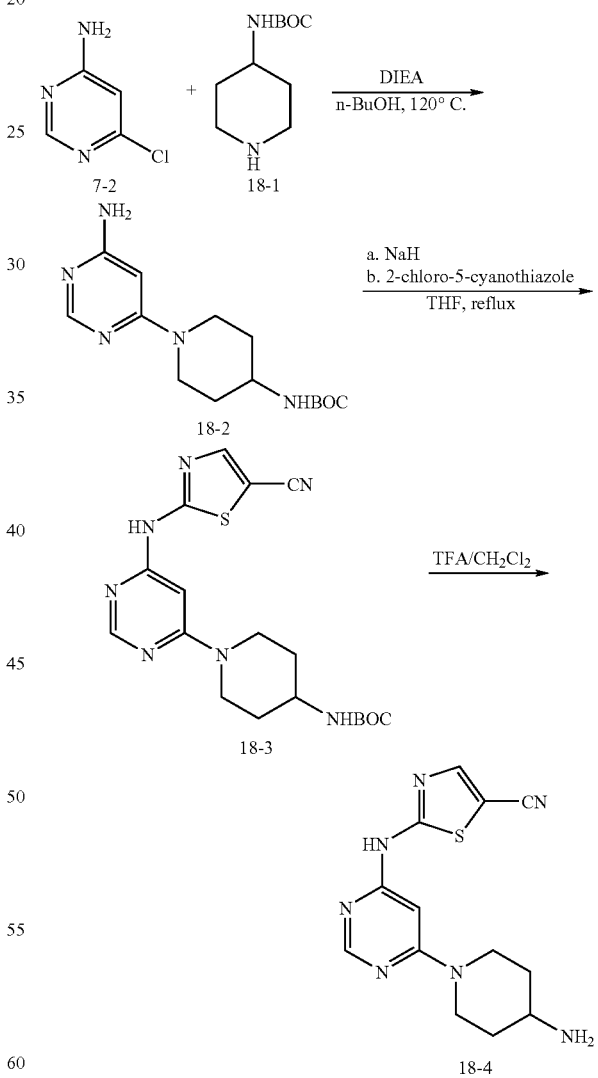

6-(4-aminopiperidin-1-yl)pyrimidin-4-amine (18-2)

In a manner identical to that described above in Scheme 7, 1.50 g (11.58 mmol) of 4-chloro-6-aminopyrimidine 7-2 and 2.32 g (11.58 mmol) 4-Boc-aminopiperidine 18-1 were used to produce 18-2 as an oil/solid. MS M+1=294.

2-{[6-(4-aminopiperidin-1-yl)pyrimidin-4-yl]amino}-1,3-thiazole-5-carbonitrile (18-4)

As described in Scheme 4 above, 2.03 g (6.91 mmol) of 6-(4-aminopiperidin-1-yl)pyrimidin-4-amine 18-2 and 1.00 g (6.91 mmol) of 2-chloro-5-cyanothiazole 2-2 were used to produce 18-4 as the bis TFA salt, which is a fluffy white amorphous powder after lyophilization. HR FAB MS: Measured=302.1175, theo.=302.1182. H1 NMR (DMSO-$d_6$): 1.44(m, 2H), 1.96(m, 2H), 3.01(m, 2H), 3.37(m, 1H), 4.29 (m, 2H), 6.24(s, 1H), 7.91 (br s, $NH_2$), 8.25(s, 1H), 8.43(s, 1H), 12.12(brs, 1H).

2-({6-[methyl(piperidin-4-ylmethyl)amino]pyrimidin-4-yl}amino)-1,3-thiazole-5-carbonitrile (19-4)

275 mg (0.86 mmol) of tert-butyl 4-{[(6-aminopyrimidin-4-yl)(methyl)amino]methyl}piperidine-1-carboxylate 19-2 and 125 mg (0.86 mmol) of 2-chloro-5-cyanothiazole 2-2 were used to afford the bis TFA salt of 19-4 as a fluffy white amorphous powder after lyophilization. FAB MS: M+1=330. H1 NMR (DMSO-$d_6$): 1.36(q, 2H), 1.73(d, 2H), 2.04(m, 1H), 2.84(q, 2H), 3.31(d, 2H), 3.56 (br m, 2H), 6.12(s, 1H), 8.25(s, 1H), 8.40(s, 1H), 8.56(bh s, 1H), 12.06 (br s, 1H).

SCHEME 19
2-({6-[methyl(piperidin-4-ylmethyl)amino]pyrimidin-4-yl}amino)-1,3-thiazole-5-carbonitrile (19-4)

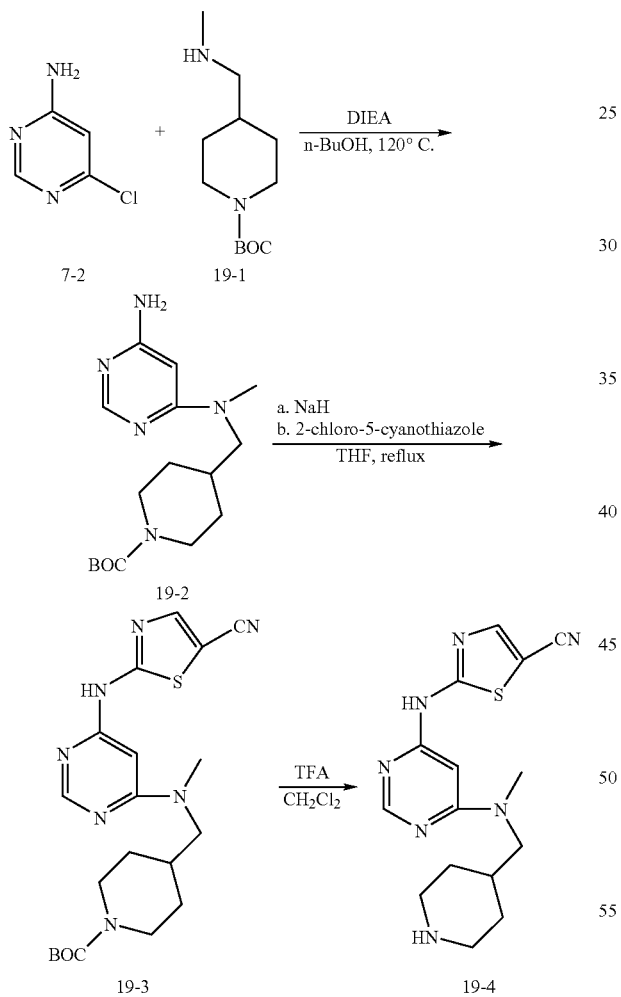

SCHEME 20
2-({2-methyl-6-[4-(2-morpholin-4-ylethyl)piperazin-1-yl]pyrimidin-4-yl}amino)-1,3-thiazole-5-carbonitrile (20-3)

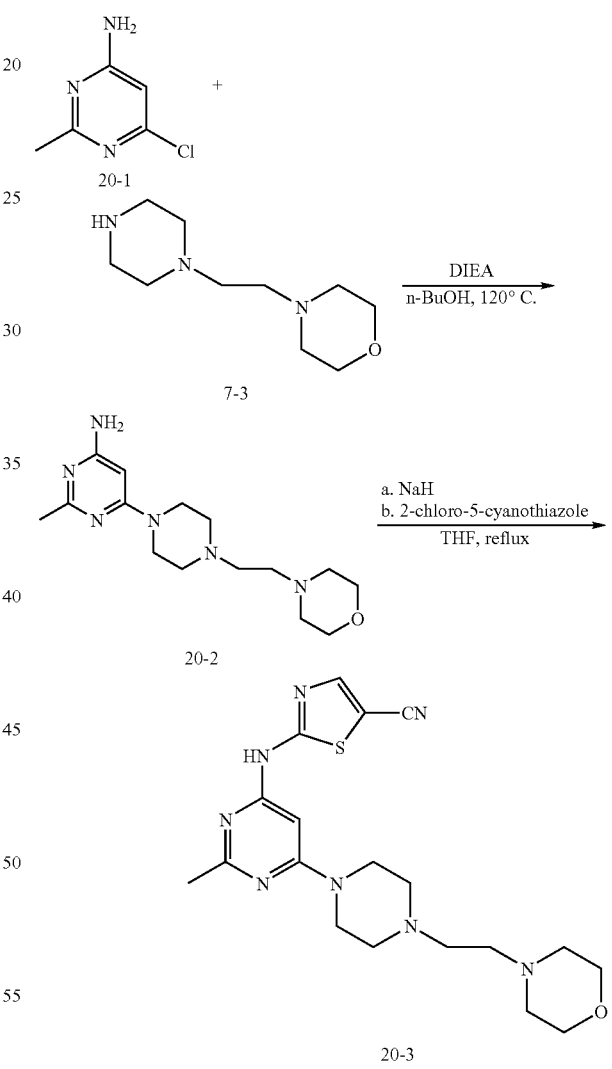

tert-butyl 4-{[(6-aminopyrimidin-4-yl)(methyl)amino]methyl}piperidine-1-carboxylate (19-2)

710 mg (3.10 mmol) of 4-chloro-6-aminopyrimidine 7-2 and 402 mg (3.10 mmol) of tert-butyl 4-[(methylamino)methyl]piperidine-1-carboxylate 19-1 were used to obtain desired product 19-2 as a brown oil/solid. MS M+1=323.

2-methyl-6-[4-(2-morpholin-4-ylethyl)piperazin-1-yl]pyrimidin-4-amine (20-2)

210 mg (1.47 mmol) of 2-methyl-4-chloro-6-aminopyrimidine 20-1 and 294 mg (1.47 mmol) of 4-(2-piperazin-1-ylethyl)morpholine 7-3 were used to obtain the desired product 20-2 as a yellow oil/solid. MS M+1=307. H1 NMR (CDCl₃): 2.37(s, 3H), 2.53(br m, 4H), 2.57(br m, 4H), 3.57(m, 4H), 3.73(m, 4H), 4.52(br s, 2H), 5.41(s, 1H).

2-({2-methyl-6-[4-(2-morpholin-4-ylethyl)piperazin-1-yl]pyrimidin-4-yl}amino)-1,3-thiazole-5-carbonitrile (20-3)

From 244 mg (0.80 mmol) of 2-methyl-6-[4-(2-morpholin-4-ylethyl)piperazin-1-yl]pyrimidin-4-amine 20-2 and 116 mg (0.80 mmol) of 2-chloro-5-cyanothiazole 2-2 was obtained the trisTFA salt of 20-3 as fluffy pale yellow amorphous powder after lyophilization. HR FAB MS: Measured=415.2043, theo.=415.2023. H1 NMR (DMSO-d₆): 2.46(s, 3H), 3.03(br s, 2H), 3.14(br s, 8H), 3.24 (br s, 2H), 3.80(br s, 8H), 6.14(s, 1H), 8.26(s, 1H).

SCHEME 21
2-({5-methyl-6-[4-(2-morpholin-4-ylethyl)piperazin-1-yl]pyrimidin-4-yl}amino)-1,3-thiazole-5-carbonitrile (21-3)

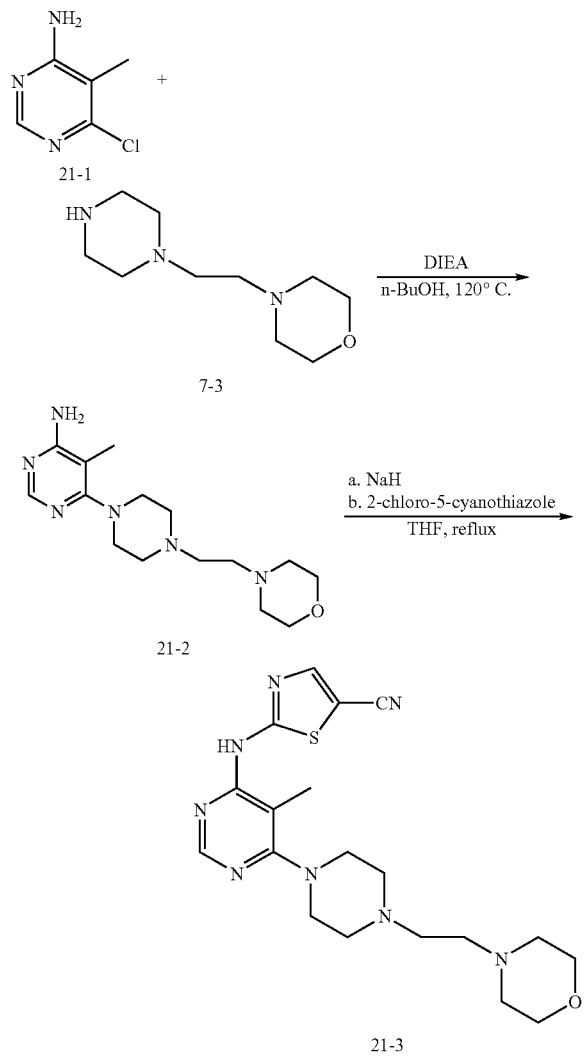

5-methyl-6-[4-(2-morpholin-4-ylethyl)piperazin-1-yl]pyrimidin-4-amine (21-2)

From 400 mg (2.79 mmol) of 4-chloro-5-methyl-6-aminopyrimidine 21-1 and 556 mg (2.79 mmol) of 4-(2-piperazin-1-ylethyl)morpholine 7-3 was obtained the desired product 21-2 as a tan oil/solid. FAB MS M+1=307. H1 NMR (CDCl₃): 2.00(s, 3H), 2.57(m, 4H), 2.64(m, 8H), 3.37(m, 4H), 3.76(m, 4H), 5.18(br s, 2H), 8.16(s, 1H).

2-({5-methyl-6-[4-(2-morpholin-4-ylethyl)piperazin-1-yl]pyrimidin-4-yl}amino)-1,3-thiazole-5-carbonitrile (21-3)

375 mg (1.22 mmol) of 5-methyl-6-[4-(2-morpholin-4-ylethyl)piperazin-1-yl]pyrimidin-4-amine 21-2 and 177 mg (1.22 mmol) of 2-chloro-5-cyanothiazole 2-2 were used to obtain the tris TFA salt of 21-3 as a fluffy pale yellow amorphous powder after lyophilization. FAB MS M+1=416. H1 NMR (DMSO-d6): 2.19(s, 3H), 3.01(br s, 4H), 3.22 (br s, 8H), 3.54(br s, 4H), 3.78(br s, 4H), 8.36(s, 1H), 8.57(s, 1H), 11.77(br s, 1H).

SCHEME 22

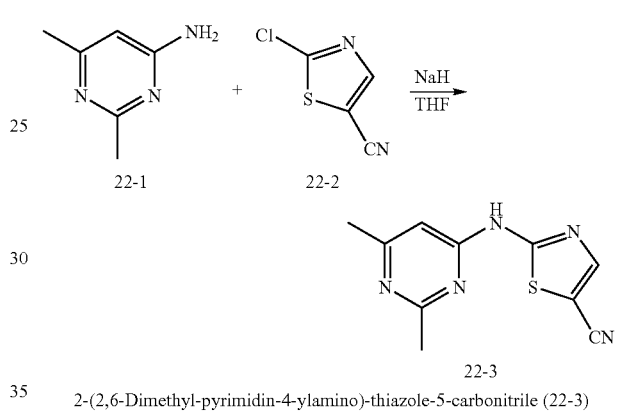

2-(2,6-Dimethyl-pyrimidin-4-ylamino)-thiazole-5-carbonitrile (22-3)

4-amino-2,6-dimethylpyrimidine (93 mg, 0.76 mmol) was dissolved in 1.4 mL anhydrous DMF and sodium hydride (66 mg, 60% dispersion, 2.77 mmol) was added at room temperature. When the bubbling stopped, 2-chlorothiazole-5-carbonitrile (0.100 g, 0.692 mmol) was added and the reaction was stirred at room temperature. After 4 hours, 1M HCl was added until the solution was neutral. The resulting precipitate was filtered, washed with water, and dried under high vacuum. The material was washed with hexane and filtered again and air dried to afford the title compound. ¹H-NMR (300 MHz, DMSO-d₆) 12.47 (1H, s), 8.32 (1H, s), 6.75 (1H, s), 2.58 (3H, s), 2.38 (3H, s). M+1=232.1. MP>250

2-(Pyrimidin-4-ylamino)-thiazole-5-carbonitrile (22-4)

Compound 22-4 was prepared in an identical fashion to 22-3. ¹H-NMR (400 MHz, DMSO) 12.63 (1H, s), 8.96 (1H, s), 8.59 (1H, d J=5.39), 8.36 (1H, s) 7.14 (1H, d, J=5.8). M+1=204. MP>250

2-[6-(4-Acetyl-piperazin-1-yl)-pyrimidin-4-ylamino]-thiazole-5-carbonitrile (22-5)

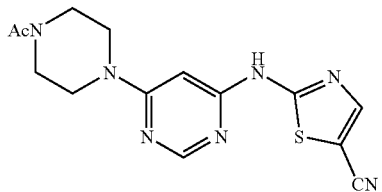

1-[4-(6-Amino-pyrimidin-4-yl)-piperazin-1-yl]-ethanone TFA salt (72 mg, 0.22 mmol) was stirred in anhydrous THF under $N_2$. Sodium hydride (26 mg, 60% dispersion, 0.65 mmol) was added followed by the addition of 2-chlorothiazole-5-carbonitrile (62 mg, 0.43 mmol). The reaction was heated to reflux and after 30 minutes additional 2-chlorothiazole-5-carbonitrile (85 mg, 0.59 mmol) was added. After a total of 1.5 hours, the reaction was cooled to room temperature, diluted with water and the bulk of the tHF was removed in vacuo. The resulting mixture was adjusted to pH 7 with 1 M HCl (aq). The resulting precipitate was filtered, washed with water and after air drying was washed with hexane. $^1$H-NMR (400 MHz, DMSO) 12.11 (1H, s), 8.45 (1H, s), 8.26 (1H, s), 6.23 (1H, s), 3.62–3.55 (m, 8H), 2.05 (s, 3H). M+1=330.2.

2-[6-(4-Methyl-piperazin-1-yl)-pyrimidin-4-ylamino]-thiazole-5-carbonitrile (22-6)

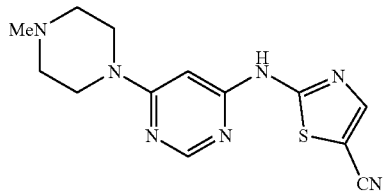

6-(4-Methyl-piperazin-1-yl)-pyrimidin-4-ylamine (97 mg, 0.50 mmol) was stirred in 2 mL anhydrous THF under $N_2$. Sodium hydride (43 mg, 60% dispersion, 1.10 mmol) was added and after stirring for 30 minutes, 2-chlorothiazole-5-carbonitrile (87 mg, 0.60 mmol). After LCMS indicated complete conversion, the reaction was quenched with MeOH, neutralized with 10% citric acid (aq). The resulting precipitate was filtered, washed with water and after air drying was washed with hexane. $^1$H-NMR (400 MHz, DMSO) 12.00 (1H, s), 8.42 (1H, s), 8.25 (1H, s), 6.21 (1H, s), 3.54 (m, 4H), 2.39 (m, 4H), 2.21 (s, 3H). M+1=302.3.

2-(6-Dimethylamino-pyrimidin-4-ylamino)-thiazole-5-carbonitrile (22-7)

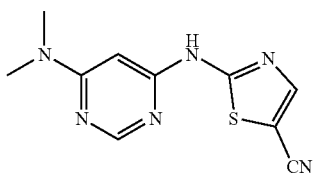

Prepared by the same method as 22-6. $^1$H-NMR (400 MHz, DMSO) 12.02 (1H, s), 8.40 (1H, s), 8.24 (1H, s), 6.09 (1H, s), 3.05 (s, 6H). M+1=247.1.

2-(6-Pyrrolidin-1-yl-pyrimidin-4-ylamino)-thiazole-5-carbonitrile (22-8)

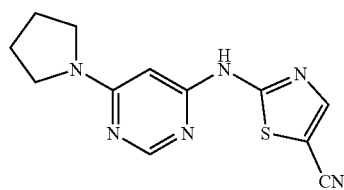

Prepared by the same method as 22-6. $^1$H-NMR (400 MHz, DMSO) 12.01 (1H, s), 8.38 (1H, s), 8.24 (1H, s), 5.95 (1H, s), 3.40 (bs, 4H), 1.95 (bs, 4H). M+1=273.1.

2-(6-Morpholin-4-yl-pyrimidin-4-ylamino)-thiazole-5-carbonitrile (22-9)

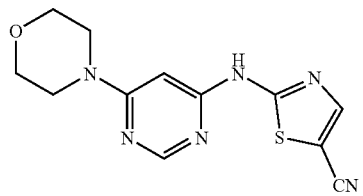

6-Morpholin-4-yl-pyrimidin-4-ylamine (185 mg, 1.03 mmol) was stirred in 5 mL anhydrous THF under $N_2$. Sodium hydride (82 mg, 60% dispersion, 2.05 mmol) was added and the reaction was warmed to 45° C. for 5 minutes. 2-chloro-thiazole-5-carbonitrile (208 mg, 1.44 mmol) was added and the reaction was heated to reflux. After 30 minutes added additional 2-chloro-thiazole-5-carbonitrile (85 mg, 0.59 mmol). After an additional 1 hour the reaction was cooled to room temperature, quenched with water and the THF was removed in vacuo. The mixture was neutralized with 1 M HCL and the resulting precipitate was filtered and washed with water. The solid was suspended in DMSO, filtered and washed with EtOAc to provide the title compound. $^1$H-NMR (400 MHz, CD$_3$OD) 8.44 (1H, s), 7.95 (1H, s), 6.13 (1H, s), 3.81 (t, 4H, J=5.0 Hz), 3.63 (t, 4H, J=4.9 Hz). M+1=289.1.

2-(6-Piperidin-1-yl-pyrimidin-4-ylamino)-thiazole-5-carbonitrile (22-10)

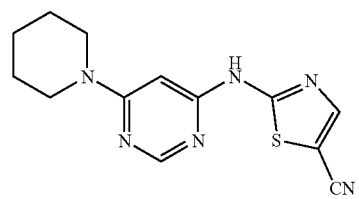

A flame dried flask under Ar was charged with sodium hydride (35 mg, 60% dispersion, 0.86 mmol) and 2 mL anhydrous THF. 6-Piperidin-1-yl-pyrimidin-4-ylamine (70 mg, 0.39 mmol) was added slowly followed after 10 minutes by the addition of 2-chloro-thiazole-5-carbonitrile (68 mg, 0.47 mmol). After 1 hour at room temperature the reaction was heated to reflux. After 4 hours, the reaction was cooled, diluted with water and adjusted to pH 7 with 1M HCl (aq). The resulting precipitate was filtered washed with water and air dried. The resulting solid triturated with ether, sonucated, filtered and washed with ether. $^1$H-NMR (400 MHz, DMSO-$d_6$) 11.99 (s, 1H), 8.39 (1H, s), 8.24 (1H, s), 6.20 (1H, s), 3.57–3.54 (m, 4H), 1.64–1.53 (m, 6H). M+1=287.3. mp>250.

2-(6-Methoxy-pyrimidin-4-ylamino)-thiazole-5-carbonitrile (22-11)

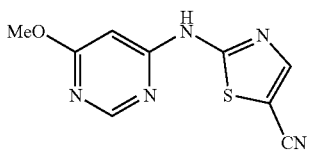

A flame dried flask under argon gas was charged with sodium hydride (39 mg, 60% dispersion, 0.97 mmol) and 2 mL anhydrous THF. 6-Methoxy-pyrimidin-4-ylamine (55 mg, 0.44 mmol) was added slowly followed, after 10 minutes, by the addition of 2-chloro-thiazole-5-carbonitrile (76 mg, 0.53 mmol). After 1 hour, the reaction was diluted with water and adjusted to pH 7 with 1M HCl (aq). The resulting precipitate was filtered, washed with water and air dried. The resulting solid triturated with ether, sonucated, filtered and washed with ether. $^1$H-NMR (400 MHz, DMSO-$d_6$) 12.40 (s, 1H), 8.68 (1H, s), 8.31 (1H, s), 6.42 (1H, s), 3.92 (s, 3H). M+1=234.2. mp 246–248.

2-(2,6-Dimethoxy-pyrimidin-4-ylamino)-thiazole-5-carbonitrile (22-12)

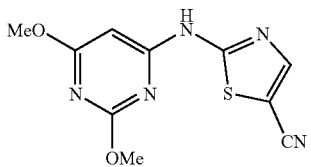

A flame dried flask under Ar was charged with sodium hydride (110 mg, 60% dispersion, 2.77 mmol) and 3 mL anhydrous THF. 2,6-Dimethoxy-pyrimidin-4-ylamine (118 mg, 0.76 mmol) was added slowly. After the resulting bubbling ceased, 2-chloro-thiazole-5-carbonitrile (100 mg, 0.69 mmol) was added and the reaction was heated to 40° C. After several hours the reaction was cooled to room temperature, the ThF was removed in vacuo, and the mixture was diluted with water and adjusted to pH 7 with 1M HCl (aq). The resulting precipitate was filtered, washed with water and air dried. The resulting solid was purified by flash column chromatography (eluted with 3:1 hexane/EtOAc) followed by purification by reverse phase HPLC. The product was free based with sat NaHCO$_3$ (aq) and filtered to give a pure sample of the title compound. $^1$H-NMR (300 MHz, DMSO-$d_6$) 12.36 (s, 1H), 8.29 (1H, s), 6.02 (1H, s), 4.02 (s, 3H), 3.87 (s, 3H). mp>250.

2-(2-Methoxy-pyrimidin-4-ylamino)-thiazole-5-carbonitrile (22-13)

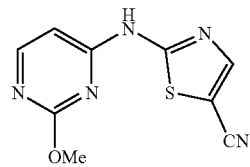

A flame dried flask under argon (g) was charged with sodium hydride (33 mg, 60% dispersion, 0.83 mmol) and 1.5 mL anhydrous THF. 2-Methoxy-pyrimidin-4-ylamine (26 mg, 0.21 mmol) was added slowly. After the resulting bubbling ceased, 2-chloro-thiazole-5-carbonitrile (30 mg, 0.21 mmol) was added and the reaction was heated to reflux. After 2 hours, the reaction was cooled to room temperature, the THF was removed in vacuo, and the mixture was diluted with water and adjusted to pH 7 with 1M HCl (aq). The resulting precipitate was filtered, washed with water and air dried. The resulting solid was purified by flash column chromatography (eluted with a gradient 85:15 hexane/EtOAc to EtOAc) to give a pure sample of the title compound. $^1$H-NMR (300 MHz, DMSO-$d_6$) 12.61 (s, 1H), 8.36 (d, 1H, J=6.4 Hz), 6.73 (d, 1H, J=5.6 Hz), 4.02 (s, 3H). mp>250.

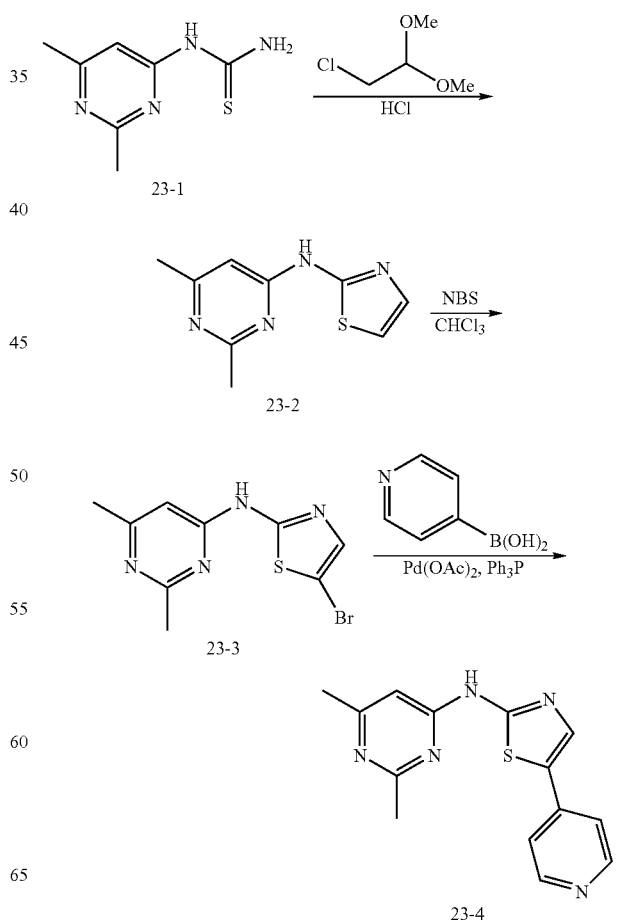

SCHEME 23

(2,6-Dimethyl-pyrimidin-4-yl)-thiazol-2-yl-amine (23-2)

2,6-Dimethyl-(4-thiourea)pyrimidine (275.0 mg, 1.51 mmol) was added to a round bottomed flask along with excess 2-chloro-1,1-dimethoxyethane, 2 mL ethanol and 2.0 mL concentrated hydrochloric acid and 10 mL of water at room temperature. The reaction was allowed to reflux over night. The reaction was cooled and neutralized with sodium hydroxide. The solid which precipitated was collected, air dried and used as is. $^1$H-NMR (400 MHz, DMSO-$d_6$) 11.53 (1H, s), 7.43 (1H, d), 7.14 (1H, d), 6.69 (1H, s), 2.50 (3H, s), 2.31 (3H, s). MS(M+1)=207.

(5-Bromo-thiazol-2-yl)-(2,6-dimethyl-pyrimidin-4-yl)-amine (23-3)

To a round bottomed flask were added 50 mg of (2,6-dimethyl-pyrimidin-4-yl)-thiazol-2-yl-amine (23-2), chloroform (3.0 mL) and 47 mg of N-bromosuccinimide. The reaction was allowed to stir at room temperature for 2 hours. The chloroform was diluted with ethyl acetate and washed with saturated sodium bisulfite solution. The ethyl acetate was dried (MgSO$_4$) and the solvent removed under high vac to give the desired product. The title compound was used as is. $^1$H-NMR (400 MHz, DMSO-$d_6$) 11.05 (1H, s), 7.53 (1H, s), 6.69 (1H, d), 6.69 (1H, s), 2.54 (3H, s), 2.35 (3H, s). MS(M+1)=285.

(2,6-Dimethyl-pyrimidin-4-yl)-(5-pyridin-4-yl-thiazol-2-yl)-amine (23-4)

To a round bottomed flask were added (5-bromo-thiazol-2-yl)-(2,6-dimethyl-pyrimidin-4-yl)-amine (23-3) (100 mg, 0.35 mmol), 4-pyridineboronicacid (47 mg, 0.39 mmol), and isopropanol. After 0.5 hour palladium acetate (0.1 mg 0.0035 mmol), triphenylphosphine (2.75 mg, 0.0105 mmol), sodiumcarbonate (45 mg, 0.42 mmol) and water were added. The reaction was heated under reflux for 1.0 hour. The reaction was cooled, solvents removed and the residue dissolved into methanol (4.0 mL). Trifluoroacetic acid (0.5 mL) was added and the mixture purified by reverse phase preparative HPLC (C18) giving the above compound as a TFA salt. $^1$H-NMR (400 MHz, CD$_3$OD) 8.71 (2H, br-s), 8.48 (1H, s), 8.18 (2H, br-s), 6.99 (1H, s), 2.82 (3H, s), 2.57 (3H, s). MS(M+1)=284.

SCHEME 24

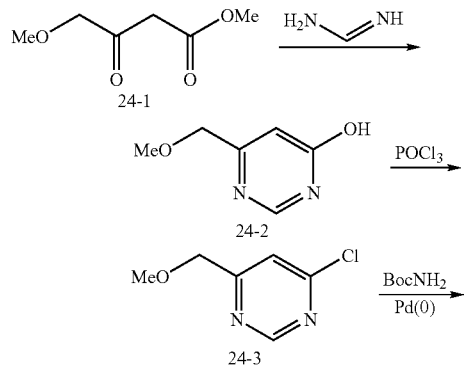

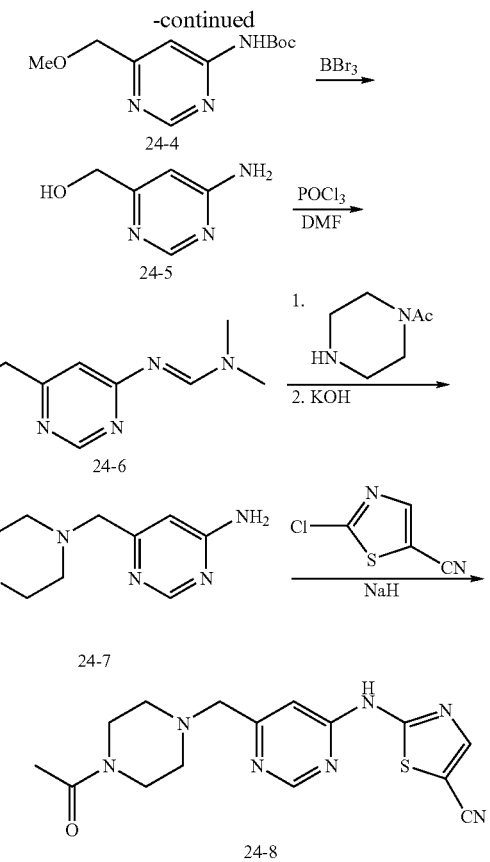

6-(Methoxymethyl)pyrimidin-4-ol (24-2)

To a solution of methyl 4-methoxyacetoacetate (2.0 g, 13.69 mmole) in MeOH (15 mL) was added formamidine acetate (1.57 g, 15.05 mmole) and NaOMe (6.5 mL of a 25% by weight solution in MeOH, 30.11 mmole) then the mixture was heated to reflux. After 18 hours, the mixture was cooled to room temperature and concentrated to dryness. The residue was taken up in H$_2$O and the pH adjusted to 7. The aqueous mixture was extracted with CHCl$_3$ (3×). The combined organic layers were dried (MgSO$_4$), filtered, and concentrated to give the title compound which was sufficiently pure for use in the next step without purification. $^1$H-NMR (500 MHz, CDCl$_3$) δ 8.17 (s, 1H), 6.60 (s, 1H), 4.38 (s, 2H), 3.50 (s, 3H).

4-Chloro-6-(methoxymethyl)pyrimidine (24-3)

6-(Methoxymethyl)pyrimidin-4-ol (948 mg, 6.8 mmole) was taken up in CH$_2$Cl$_2$ (10 mL) and POCl$_3$ (6 mL) at room temperature. After 18 hours, the mixture was concentrated to dryness. The residue was taken up in ice water and the pH adjusted to 7. The mixture was extracted with CHCl$_3$ (4×). The combined organic layers were dried (MgSO$_4$), filtered, and concentrated to give the title compound which was sufficiently pure for use in the next step without purification. $^1$H-NMR (500 MHz, CDCl$_3$) δ 8.95 (s, 1H), 7.58 (s, 1H), 4.48 (s, 2H), 3.50 (s, 3H).

tert-Butyl 6-(methoxymethyl)pyrimidin-4-ylcarbamate (24-4)

To a solution of 4-chloro-6-(methoxymethyl)pyrimidine (768 mg, 4.84 mmole) in dry dioxane (10 mL) was added $Cs_2CO_3$ (2.37 g, 7.26 mmole), Xanthphos (84 mg, 0.15 mmole), $Pd_2(dba)_3$ (44 mg, 0.05 mmole), and tert-butylcarbamate (681 mg, 5.81 mmole) then the mixture was heated to reflux. After 3 hours, the mixture was cooled to room temperature, diluted with $H_2O$, and extracted with $CH_2Cl_2$ (3×). The combined organic layers were dried ($MgSO_4$), filtered, and concentrated. Flash column chromatography (35% EtOAc/hexanes) gave the title compound as a pale yellow solid. $^1$H-NMR (500 MHz, $CDCl_3$) δ 8.74 (s, 1H), 8.04 (s, 1H), 8.00 (bs, 1H), 4.51 (s, 2H), 3.51 (s, 3H), 1.55 (s, 9H).

(6-Aminopyrimidin-4-yl)methanol (24-5)

To a solution of tert-butyl 6-(methoxymethyl)pyrimidin-4-ylcarbamate (100 mg, 0.42 mmole) in $CH_2Cl_2$ (2 mL) was added $BBr_3$ (2.1 mL, 1M solution in $CH_2Cl_2$, 2.1 mmole) dropwise at −20° C. After 1.5 hours, the mixture was quenched with MeOH and concentrated. The solid was taken up in MeOH and concentrated (2×) and dried in vacuo to give the title compound as a tan solid. $^1$H-NMR (300 MHz, $d_6$-DMSO) δ 8.63 (s, 1H), 6.64 (s, 1H), 4.50 (s, 2H).

N'-(6-Chloromethyl-pyrimidin-4-yl)-N,N-dimethyl-formamidine (24-6)

To a suspension of (6-aminopyrimidin-4-yl)methanol (52 mg, 0.42 mmole) in $CH_2Cl_2$ (2 mL) was added DMF (0.03 mL, 0.42 mmole) then $POCl_3$ (0.04 mL, 0.42 mmole) at room temperature. After 2 hours, $Et_3N$ (0.3 mL) was added and stirring continued. After 18 hours, the mixture was concentrated. The residue was taken up in saturated $NaHCO_3$ and extracted with $CH_2Cl_2$ (4×). The combined organic layers were dried ($MgSO_4$), filtered, and concentrated to give the title compound as its DMF amidine. $^1$H-NMR (300 MHz, $d_6$-DMSO) δ 8.78 (s, 1H), 8.65 (s, 1H), 6.90 (s, 1H), 4.60 (s, 2H), 3.18 (s, 3H), 3.05 (s, 3H).

6-[(4-Acetylpiperazin-1-yl)methyl]pyrimidin-4-amine (24-7)

To a solution of 6-(chloromethyl)pyrimidin-4-amine DMF amidine (56 mg, 0.39 mmole) in DMSO (2 mL) was added Hunig's base (0.2 mL, 1.17 mmole) and acetylpiperazine (100 mg, 0.78 mmole) at room temperature. After 18 hours LCMS indicated the desired amidine. KOH (100 mg) and MeOH:$H_2O$ (10 mL, 1:1) was added and stirring continued. After 72 hours, the mixture was made acidic with 1N HCl and washed with $CH_2Cl_2$ (2×). The aqueous layer was neutralized with saturated $NaHCO_3$, and concentrated. The residue was taken up in MeOH, filtered, and concentrated (repeat 1×). The residue was taken up in $CH_2Cl_2$, filtered, and concentrated. The crude material was used in the next step without purification.

2-({6-[(4-Acetylpiperazin-1-yl)methyl]pyrimidin-4-yl}amino)-1,3-thiazole-5-carbonitrile (24-8)

To a solution of crude 6-[(4-acetylpiperazin-1-yl)methyl] pyrimidin-4-amine (60 mg, 0.26 mmole) in dry THF (2 mL) was added NaH (50 mg, 1.27 mmole). After gas evolution had ceased 2-chloro-5-cyano-1,3-thiazole (148 mg, 1.02 mmole) was added and the mixture was heated to reflux. After 4 hours, the mixture was cooled to room temperature and quenched with saturated $NH_4Cl$. The mixture was filtered to remove a precipitate which was washed with $H_2O$ and $CH_2Cl_2$. The layers were separated and the aqueous layer extracted with $CH_2Cl_2$ (3×). The combined organic layers were dried ($MgSO_4$), filtered, and concentrated. Purification by reverse phase HPLC (5–100% $CH_3CN/H_2O$+ 0.1% TFA) gave the TFA salt of title compound as a white solid. $^1$H-NMR (300 MHz, $d_6$-DMSO) δ 12.87 (bs, 1H), 9.03 (s, 1H), 8.40 (s, 1H), 7.21 (s, 1H), 4.40–2.80 (m, 10H), 2.03 (s, 3H); MS (ES) (M+H)$^+$ 344.

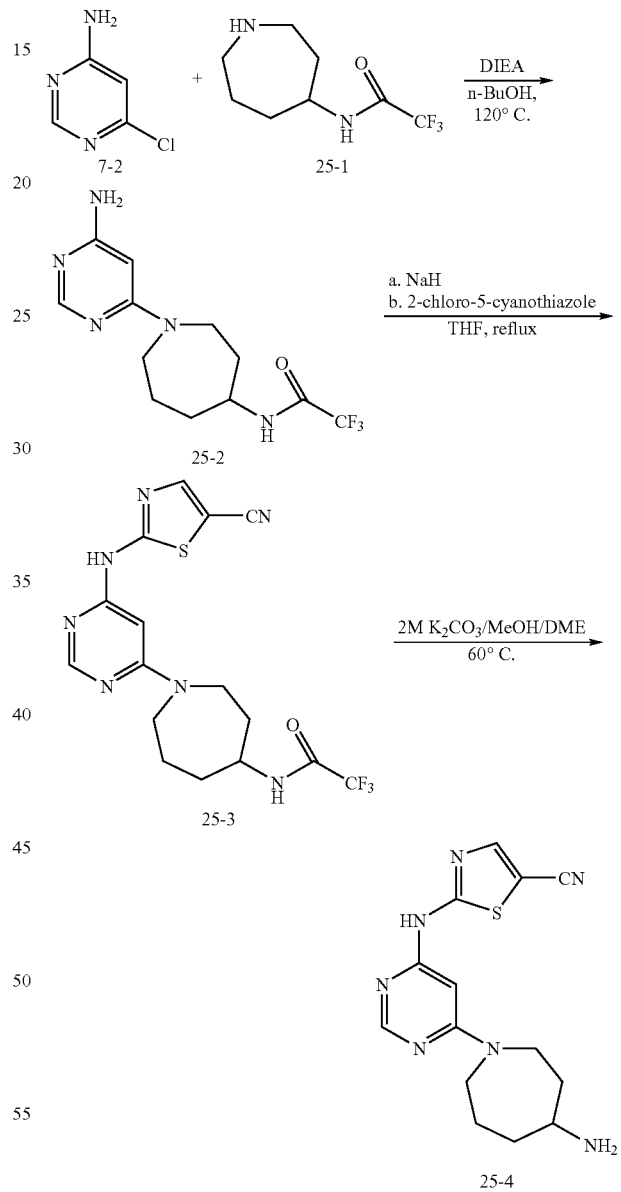

1-(6-aminopyrimidin-4-yl)azepan-4-amine (25-2)

In a manner identical to that described above in Scheme 7, 152 mg (1.17 mmol) of 4-chloro-6-aminopyrimidine 7-2 and 380 mg (1.17 mmol) of 4-trifluoroactemido-azepane 25-1 were used to produce of 25-2 as an oil. MS M+1=304.

2-{[6-(4-aminoazepan-1-yl)pyrimidin-4-yl]amino}-1,3-thiazole-5-carbonitrile (25-4)

As described in Scheme 4 above, 272 mg (0.90 mmol) of 1-(6-aminopyrimidin-4-yl)azepan-4-amine 25-2 and 130 mg (0.90 mmol) of 2-chloro-5-cyanothiazole were used to produce crude 25-3 as a brown oil. The oil was dissolved in 2 mL 2M potassium carbonate/2 mL MeOH/2 mL DME, and the resulting solution was heated at 60° C. for 18 hours. The solution was cooled and concentrated in vacuo, and the crude product purified by reversed phase prep LC to give the desired product 25-4 as a fluffy pale yellow amorphous powder after lyophilization. HR FAB MS: Measured=316.1343, theo.=316.1339. H1 NMR(DMSO-$d_6$): 1.49(m, 1H), 1.73 (br m, 2H), 1.94(m, 2H), 2.14(m, 1H), 3.18(m, 2H), 3.45(br m, 2H), 3.68(m, 1H), 6.16 (s, 1H), 7.79(br 2, 2H), 8.23(s, 1H), 8.43(s, 1H), 12.02(br s, 1H).

SCHEME 26

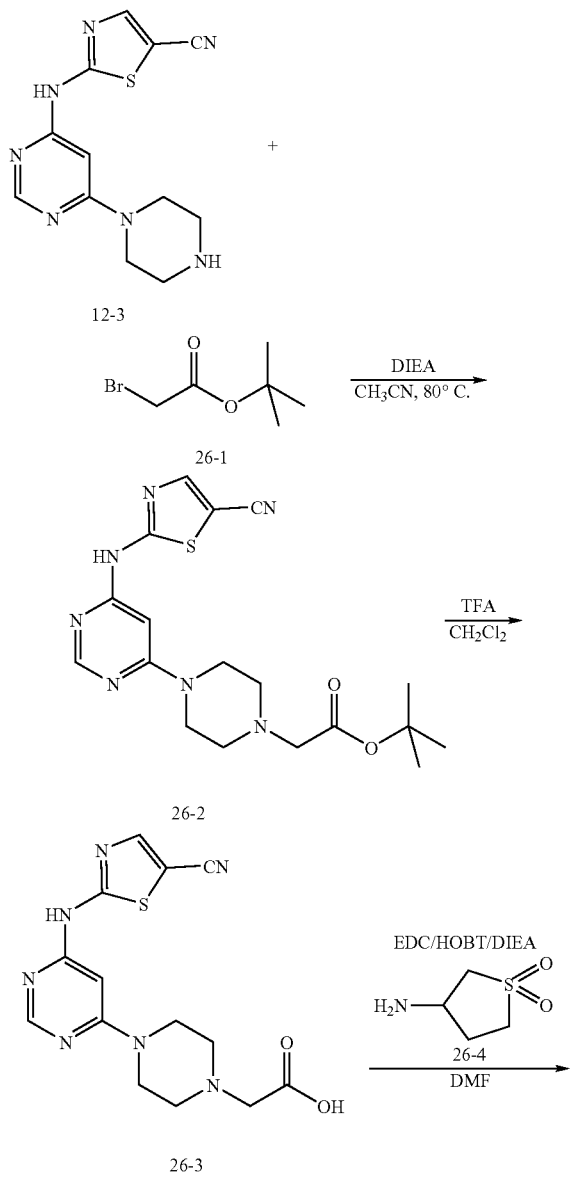

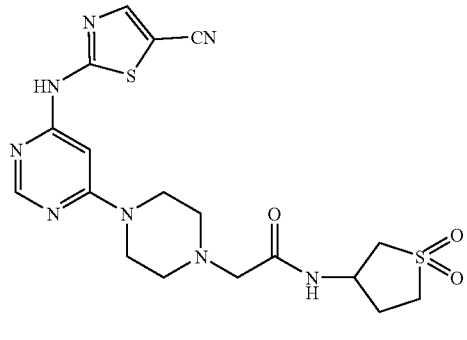

(4-{6-[(5-cyano-1,3-thiazol-2-yl)amino]pyrimidin-4-yl}piperazin-1-yl)acetic acid (26-3)

A mixture of 1.00 g (1.94 mmol) of the bis TFA salt of 12-3, 288 µL (1.94 mmol) of t-butyl bromoacetate 26-1 and 1.05 mL (6.02 mmol) of DIEA in 4 mL acetonitrile was heated at 80° C. for 18 hours. The reaction was cooled, and the resulting precipitate was removed by filtration. The solid was dissolved in 5 mL TFA/5 mL methylene chloride, and the solution stirred at room temperature for 18 hours. The reaction was concentrated in vacuo, and the crude product taken up in chloroform/methanol. A precipitate formed in the solution and was removed by filtration to give the bis TFA salt of desired product 26-3 as a pale yellow solid, MP=285–287° C. (decomp). HR Mass Spec.: Measured=346.1065, theo.=346.1081. H1 NMR: 2.59(m, 4H), 3.36(s, 2H), 3.64(br s, 4H), 6.22(s, 1H), 8.26(s, 1H), 8.44(s, 1H).

(+,−)2-(4-{6-[(5-cyano-1,3-thiazol-2-yl)amino]pyrimidin-4-yl}piperazin-1-yl)-N-(1,1-dioxidotetrahydrothien-3-)acetamide (26-5)

A solution of 150 mg (0.26 mmol) of the bis TFA salt of 26-3, 45 mg (0.26 mmol) of 1,1-dioxidotetrahydrothien-3-ylamine hydrochloride 26-4, 39 mg (0.33 mmol) of HOBT, and 210 µL (1.20 mmol) of DEEA in 2 mL anhydrous DMF was treated with 57 mg (0.33 mmol) of EDC, and the resulting solution stirred at room temperature for 18 hours. The reaction was concentrated in vacuo to a tan oil. The crude material was purified by reversed phase prep LC to afford the bis TFA salt of the desired product 26-5 as a fluffy white amorphous powder after lyophilization. HR FAB MS: Measured=463.1323, theo.=463.1329. H1 NMR(DMSO-$d_6$): 2.09(m, 1H), 2.43(m, 1H), 2.96(dd, 1H), 3.21(m, 1H), 3.29(m, 1H), 3.48(dd, 1H), 3.90(br, 8H), 4.33(br, 2H), 4.53(m, 1H), 6.31(s, 1H), 8.29(s, 1H), 8.54(s, 1H), 12.24(s, 1H).

SCHEME 27

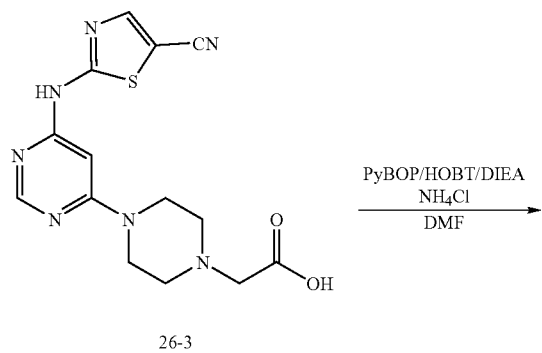

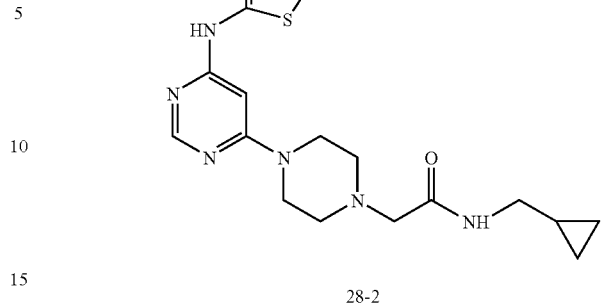

2-(4-{6-[(5-cyano-1,3-thiazol-2-yl)amino]pyrimidin-4-yl}piperazin-1-yl)-N-(cyclopropylmethyl)acetamide (28-2)

As described in Scheme 26 above, 150 mg (0.26 mmol) of the bis TFA salt of 26-3 and 19 mg (0.54 mmol) of cyclopropylmethyamine 28-1 were used to produce the bis TFA salt of 28-2 as an amorphous fluffy white powder after lyophilization. HR FAB MS: Measured=399.1700, theo.=399.1710. H1 NMR(DMSO-$d_6$): 0.20(dq, 2H), 0.45 (dq, 2H), 0.93(m, 1H), 3.05(t, 2H), 3.19(br, 2H), 3.38(br, 2H), 3.55(br, 2H), 3.79(br s, 2H), 4.36(br, 2H), 6.29(s, 1H), 8.28(s, 1H), 8.52(s, 1H), 8.66(br s, 1H), 12.24(s, 1H).

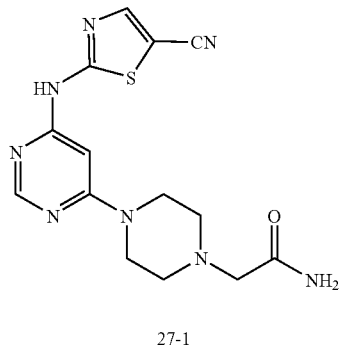

2-(4-{6-[(5-cyano-1,3-thiazol-2-yl)amino]pyrimidin-4-yl}piperazin-1-yl)acetamide (27-1)

As described in Scheme 26 above using PyBOP instead of EDC as the coupling agent, 150 mg (0.26 mmol) of the bis TFA salt of 26-3 and 30 mg (0.54 mmol) of ammonium chloride were used to produce the bis TFA salt of 27-1 as an amorphous fluffy white powder after lyophilization. HR FAB MS: Measured=345.1229, theo.=345.1241. H1 NMR (DMSO-$d_6$): 3.19(br, 2H), 3.41(br, 2H), 3.55 (br, 2H), 4.03(br, 2H), 4.37(br, 2H), 6.33(s, 1H), 7.76(br s, 2H), 8.29(s, 1H), 8.53(s, 1H), 12.14(s, 1H).

SCHEME 29

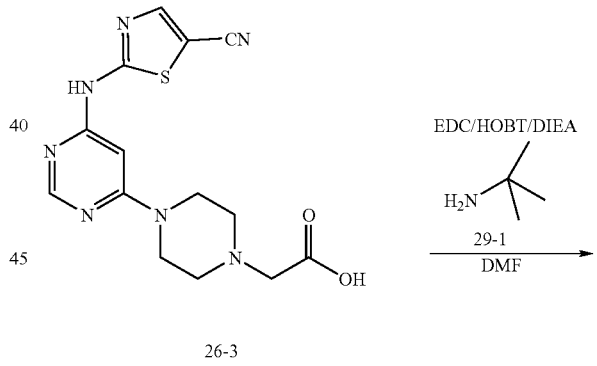

SCHEME 28

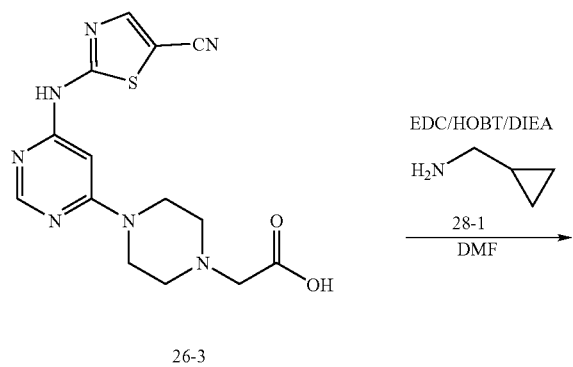

N-(tert-butyl)-2-(4-{6-[(5-cyano-1,3-thiazol-2-yl)amino]pyrimidin-4-yl}piperazin-1-yl)acetamide (29-2)

As described in Scheme 26 above, 200 mg (0.35 mmol) of the bis TFA salt of 2-3 and 37 µL (0.54 mmol) of t-butyl amine 29-1 were used to produce the bis TFA salt of 29-2 as an amorphous fluffy white powder after lyophilization. HR FAB MS: measured=401.1842, theo.=401.1867. H1 NMR (DMSO-$d_6$): 1.34(s, 9H), 3.18(br, 2H), 3.38(br, 2H), 3.56(br, 2H), 3.91(br s, 2H), 4.38(br, 2H), 6.31(s, 1H), 8.24(br s, 1H), 8.29(s, 1H), 8.53(s, 1H), 12.25(s, 1H).

SCHEME 30

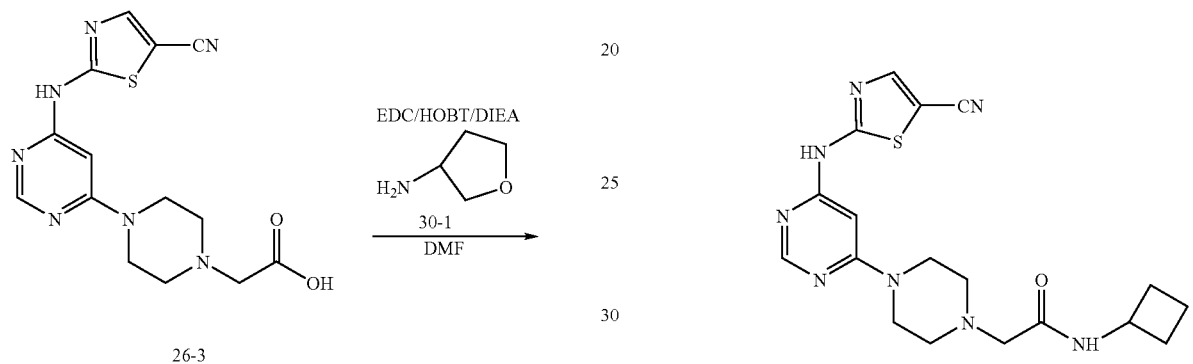

26-3

30-2

2-(4-{6-[(5-cyano-1,3-thiazol-2-yl)amino]pyrimidin-4-yl}piperazin-1-yl)-N-tetrahydrofuran-3-ylacetamide (30-2)

As described in Scheme 26 above, 200 mg (0.35 mmol) of the bis TFA salt of 26-3 and 30 mg (0.35 mmol) of 3-aminothetrahydrofuran 30-1 were used to produce the bis TFA salt of 30-2 as an amorphous fluffy white powder after lyophilization. HR FAB MS: measured=415.1632, theo.=415.1659. H1 NMR (DMSO-$d_6$): 1.77(m, 1H), 2.15 (m, 1H), 3.30(br complex, 8H), 3.54(dd, 1H), 3.70(m, 1H), 3.79(complex, 2H), 3.96(s, 2H), 4.31(m, 1H), 6.33(s, 1H), 8.27(s, 1H), 8.51(s, 1H), 8.85(d, 1H), 1.25(br s, 1H).

SCHEME 31

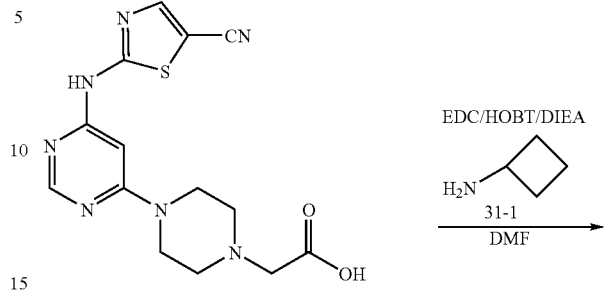

26-2

31-2

2-(4-{6-[(5-cyano-1,3-thiazol-2-yl)amino]pyrimidin-4-yl}piperazin-1-yl)-N-cyclobutylacetamide (31-2)

As described in Scheme 26 above, 200 mg (0.35 mmol) of the bis TFA salt of 26-3 and 25 mg (0.35 mmol) of cyclobutylamine 31-1 were used to produce the bis TFA salt of 31-2 as an amorphous fluffy white powder after lyophilization. HR FAB MS: Measured=399.1682, theo.=399.1710. H1 NMR(DMSO-$d_6$): 1.68(m, 2H), 1.93 (m, 2H), 2.20(m, 2H), 3.19(br, 2H), 3.39 (br, 2H), 3.52(br, 2H), 3.91(br s, 2H), 4.26(m, 1H), 4.32(br, 2H), 6.29(s, 1H), 8.29 (s, 1H), 8.52(s, 1H), 8.81(br s, 1H), 12.24(br s, 1H).

SCHEME 32

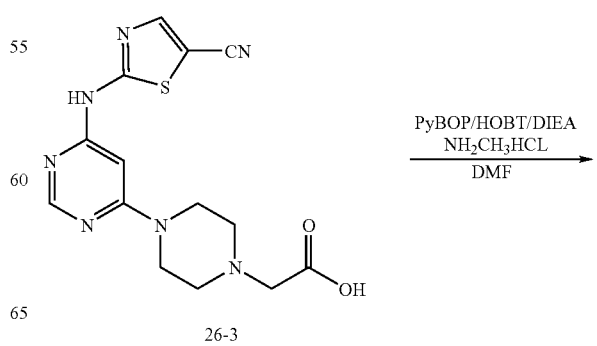

26-3

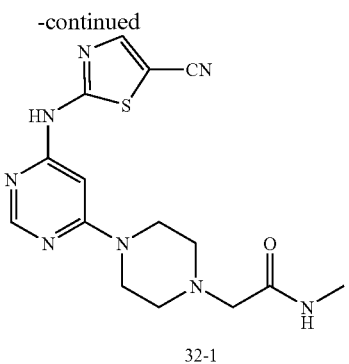

32-1

2-(4-{6-[(5-cyano-1,3-thiazol-2-yl)amino]pyrimidin-4-yl}piperazin-1-yl)-N-methylacetamide (32-1)

As described in Scheme 26 above using PyBOP instead of EDC as the coupling agent, 200 mg (0.35 mmol) of the bis TFA salt of 26-3 and 47 mg (0.35 mmol) of methylamine hydrochloride were used to produce the bis TFA salt of 32-1 as an amorphous fluffy white powder after lyophilization. HR FAB MS: Measured=359.1360, theo.=359.1397. H1 NMR (DMSO): 2.71(d, 3H), 3.22(br, 2H), 3.40 (br, 2H), 3.52(br, 2H), 3.96(br s, 2H), 4.37(br, 2H), 6.32(s, 1H), 8.28(s, 1H), 8.51(br d, 1H), 8.55(s, 1H), 12.24(br s, 1H).

SCHEME 33

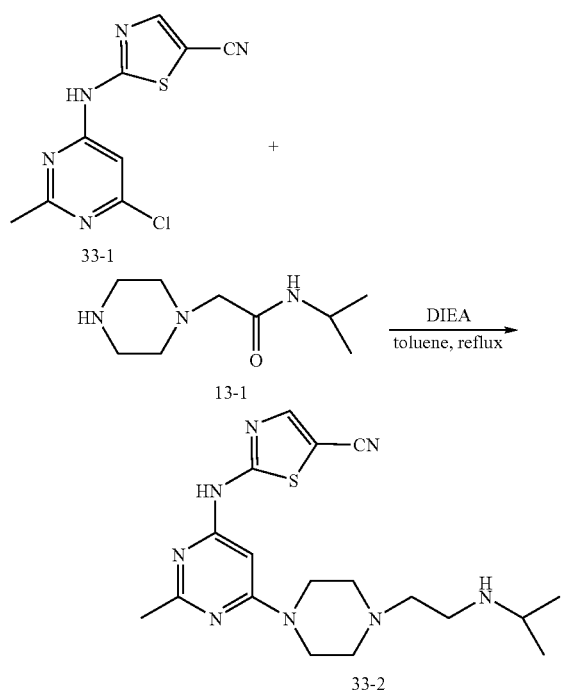

2-(4-{6-[(5-cyano-1,3-thiazol-2-yl)amino]-2-methylpyrimidin-4-yl}piperazin-1-yl)-N-isopropylacetamide (33-2)

A mixture of 150 mg (0.60 mmol) of 33-1, 222 mg (1.20 mmol) of the piperazine derivative 13-1, and 314 µL (1.80 mmol) DIEA in 5 mL toluene was stirred at reflux in a nitrogen atmosphere for 3 hours, then at 95° C. for 72 hours. The reaction was cooled and concentrated in vacuo to a brown oil. The oil was purified by reversed phase prep LC to give the bis TFA salt of the desired product 33-2 as an amorphous pale orange powder after lyophilization. HR FAB MS: Measured=401.1857, theo.=401.1867. H1 NMR (DMSO-$d_6$): 1.11(d, 6H), 2.47(s, 3H), 3.17(br, 2H), 3.46(br complex, 6H), 3.92(m, 1H), 4.35(br, 2H), 6.12(s, 1H), 8.36(s, 1H), 8.44(br s, 1H), 12.20(2, 1H).

SCHEME 34

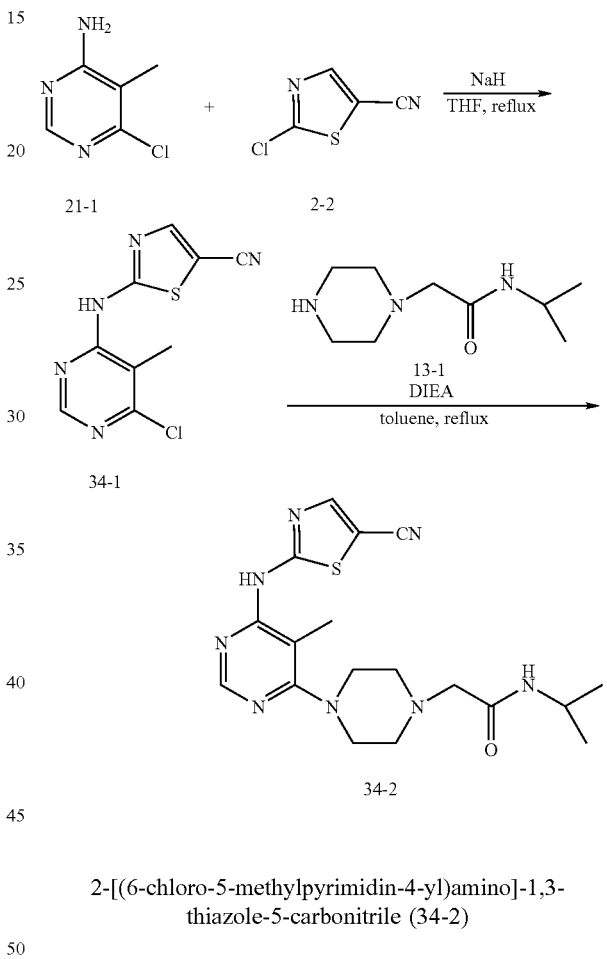

2-[(6-chloro-5-methylpyrimidin-4-yl)amino]-1,3-thiazole-5-carbonitrile (34-2)

A vigorously stirred suspension of 1.25 g (8.71 mmol) of 21-1 in 25 mL of dry THF in a nitrogen atmosphere was treated with 352 mg (8.80 mmol) of 60% NaH dispersion in oil. The suspension was stirred at room temperature for 20 minutes and a second equal portion of NaH dispersion was added. The suspension was treated dropwise with a solution of 1.26 g (871 mmol) of 2-2 in 5 mL dry THF, and the resulting suspension was stirred under reflux for 3 hours. The reaction was then cooled and concentrated to dryness, and the solid residue partitioned between ethyl acetate and water. The aqueous layer was re-extracted twice with ethyl acetate, and the combined organic extracts were washed with brine, dried, and concentrated in vacuo to afford the desired product 34-1 as an orange solid. The crude product was of suitable quality to use directly in the next step. MS M+1=252.

2-(4-{6-[(5-cyano-1,3-thiazol-2-yl)amino]-5-methylpyrimidin-4-yl}piperazin-1-yl)-N-isopropylacetamide (34-2)

As described in Scheme 33 above, 150 mg (0.60 mmol) of 34-1 and 222 mg (1.20 mmol) of 13-1 (number from patent 20721) were used to produce the bis TFA salt of the desired product 34-2 as a fluffy white amorphous powder after lyophilization. MS M+1=401. H1 NMR(DMSO-$d_6$): 1.09(d, 6H), 2.19(s, 3H), 3.37 (br complex, 8H), 3.84(br, 2H), 3.92(m, 1H), 8.35(s, 1H), 8.47(br, 1H), 8.54(s, 1H), 11.78(s, 1H).

2-({6-[4-(5-oxo-1,4-diazepan-1-yl)piperidin-1-yl]pyrimidin-4-yl}amino)-1,3-thiazole-5-carbonitrile (35-3)

A solution of 150 mg (0.63 mmol) of 35-1, 249 mg (1.26 mmol) of 35-2, and 181 µL (1.30 mmol) of TEA in 4 mL n-BuOH was heated at 120° C. in a sealed tube for 18 hours. The reaction was cooled, and the resulting precipitate was removed by filtration. The solid was dissolved in a minimal amount of MeOH/TFA, and was purified by reversed phase prep LC to give the bis TFA salt of the desired product 35-3 as an amorphous pale yellow solid after lyophilization. MS M+1=399. H1 NMR (DMSO-$d_6$): 1.62(q, 2H), 2.19(d, 2H) 2.48(dd, 1H), 2.94(m, 4H), 3.13 (m, 1H), 3.29(m, 2H), 3.69(t, 1H), 4.41(br, 2H), 6.29(s, 1H), 7.92(br t, 1H), 8.27(s, 1H), 8.46(s, 1H), 12.15(br s, 1H).

SCHEME 35

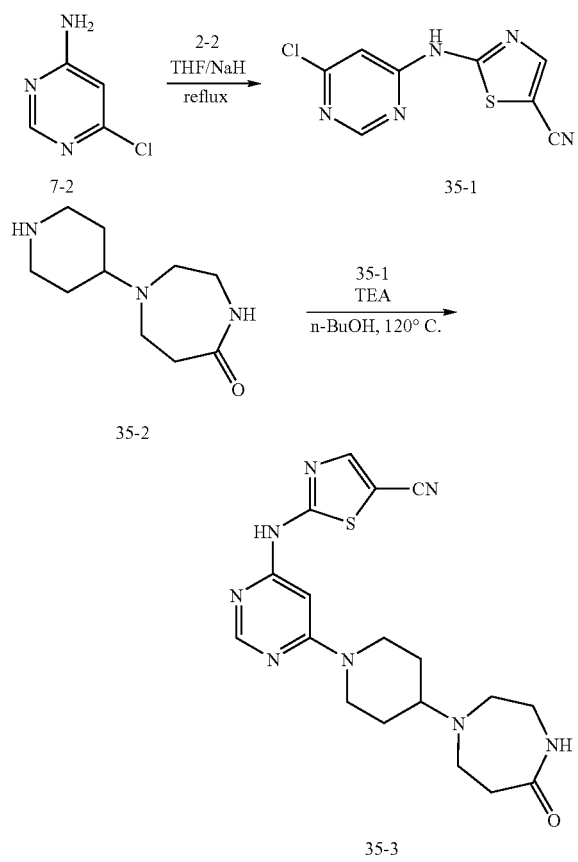

SCHEME 36

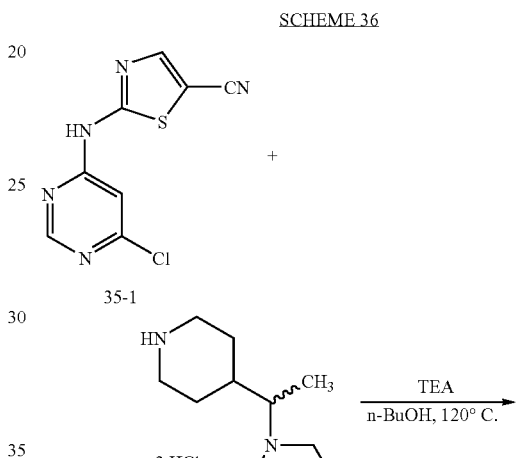

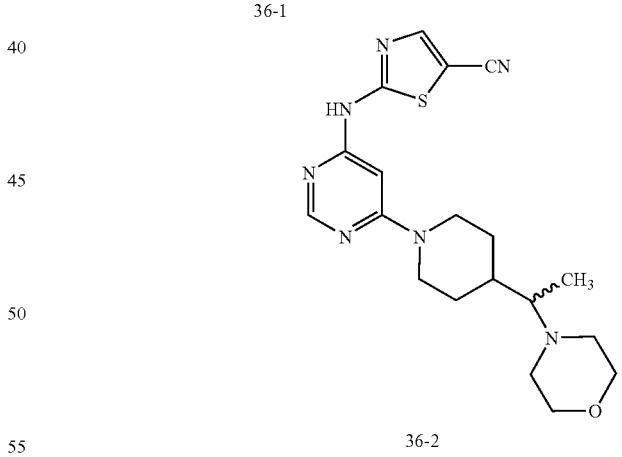

2-[(6-chloropyrimidin-4-yl)amino]-1,3-thiazole-5-carbonitrile (35-1)

7-2 (2.0 g, 15.4 mmol) and 1 equivalent of sodium hydride (0.62 g, 15.4 mmol) were suspended in THF and stirred for 20 minutes before adding 2-chloro-1,3-thiazole-5-carbonitrile 2-2 (2.23 g, 15.4 mmol) and the other equivalent sodium hydride simultaneously. The reaction was refluxed for 1.5 hours, cooled, quenched with methanol and water, evaporated to dryness and partitioned between methylene chloride, methanol and water. The aqueous layer was evaporated to dryness and purified on a silica column (DCM to 9:1:0.1 DCM:MeOH:NH$_4$OH) to afford 35-1. $^1$H-NMR (CD$_3$OD): 8.75(s, 1H); 8.10(s, 1H); 7.09(s, 1H).

(+,−)-2-({6-[4-(1-morpholin-4-ylethyl)piperidin-1-yl]pyrimidin-4-yl}amino)-1,3-thiazole-5-carbonitrile (36-2)

As described in Scheme 35 above, 150 mg (0.63 mmol) of 35-1 and 342 mg (1.26 mmol) of 36-1 were used to produce (after purification as above) the bis TFA salt of the desired product 36-2 as pale yellow amorphous powder after lyophilization. MS M+1=400. H1 NMR(DMSO-$d_6$): 1.19(d, 3H), 1.25(dq, 1H), 1.34(dq, 1H), 1.67(d, 1H), 1.77(d, 1H), 2.22(br t, 1H), 2.94(t, 2H), 3.12(m, 1H), 3.21(m, 1H), 3.29(br m, 1H), 3.47(d, 2H), 3.75(dt, 2), 4.00(d, 2H), 4.34(br, 2H), 6.26(s, 1H), 8.27(s, 1H), 8.42(s, 1H), 12.09(br s, 1H).

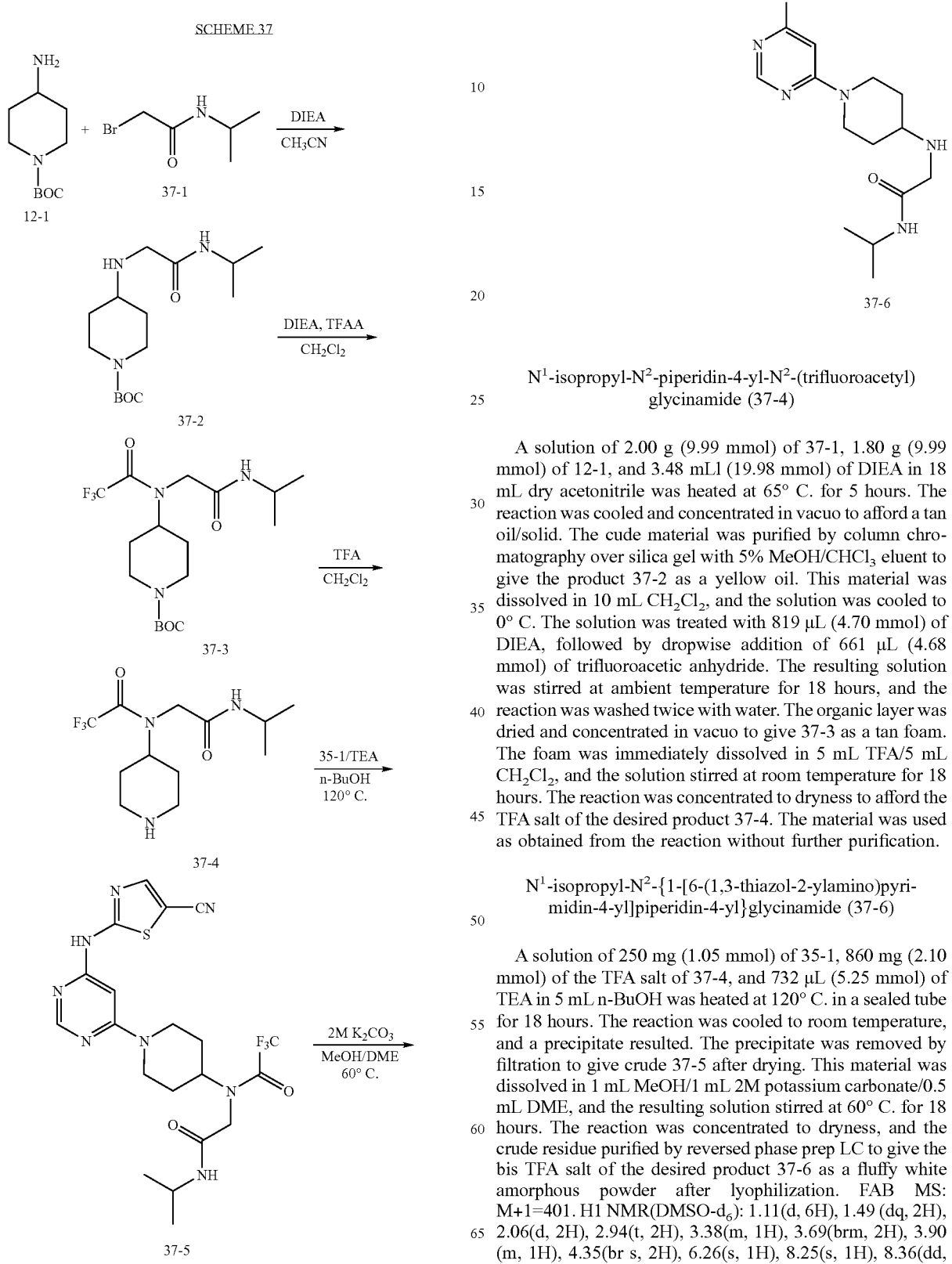

$N^1$-isopropyl-$N^2$-piperidin-4-yl-$N^2$-(trifluoroacetyl)glycinamide (37-4)

A solution of 2.00 g (9.99 mmol) of 37-1, 1.80 g (9.99 mmol) of 12-1, and 3.48 mLl (19.98 mmol) of DIEA in 18 mL dry acetonitrile was heated at 65° C. for 5 hours. The reaction was cooled and concentrated in vacuo to afford a tan oil/solid. The cude material was purified by column chromatography over silica gel with 5% MeOH/CHCl$_3$ eluent to give the product 37-2 as a yellow oil. This material was dissolved in 10 mL CH$_2$Cl$_2$, and the solution was cooled to 0° C. The solution was treated with 819 μL (4.70 mmol) of DIEA, followed by dropwise addition of 661 μL (4.68 mmol) of trifluoroacetic anhydride. The resulting solution was stirred at ambient temperature for 18 hours, and the reaction was washed twice with water. The organic layer was dried and concentrated in vacuo to give 37-3 as a tan foam. The foam was immediately dissolved in 5 mL TFA/5 mL CH$_2$Cl$_2$, and the solution stirred at room temperature for 18 hours. The reaction was concentrated to dryness to afford the TFA salt of the desired product 37-4. The material was used as obtained from the reaction without further purification.

$N^1$-isopropyl-$N^2$-{1-[6-(1,3-thiazol-2-ylamino)pyrimidin-4-yl]piperidin-4-yl}glycinamide (37-6)

A solution of 250 mg (1.05 mmol) of 35-1, 860 mg (2.10 mmol) of the TFA salt of 37-4, and 732 μL (5.25 mmol) of TEA in 5 mL n-BuOH was heated at 120° C. in a sealed tube for 18 hours. The reaction was cooled to room temperature, and a precipitate resulted. The precipitate was removed by filtration to give crude 37-5 after drying. This material was dissolved in 1 mL MeOH/1 mL 2M potassium carbonate/0.5 mL DME, and the resulting solution stirred at 60° C. for 18 hours. The reaction was concentrated to dryness, and the crude residue purified by reversed phase prep LC to give the bis TFA salt of the desired product 37-6 as a fluffy white amorphous powder after lyophilization. FAB MS: M+1=401. H1 NMR(DMSO-d$_6$): 1.11(d, 6H), 1.49 (dq, 2H), 2.06(d, 2H), 2.94(t, 2H), 3.38(m, 1H), 3.69(brm, 2H), 3.90 (m, 1H), 4.35(br s, 2H), 6.26(s, 1H), 8.25(s, 1H), 8.36(dd, 1H), 8.44(s, 1H), 8.93(d, 1H), 12.14(s, 1H).

SCHEME 38

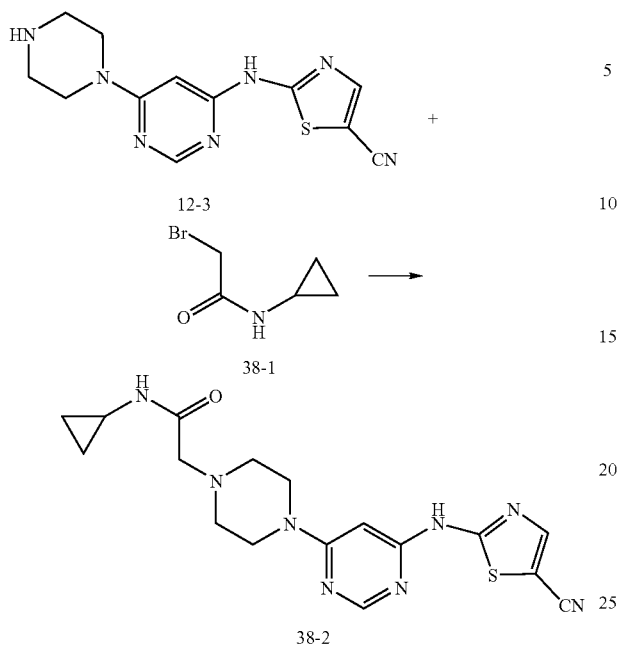

2-(4-{6-[(5-Cyano-1,3-thiazol-2-yl)amino]pyrimidin-4-yl}piperazin-1-yl)-N-cyclopropyl-acetamide (38-2)

12-3 (0.2 g, 0.39 mmol) and 2-bromo-N-cyclopropylacetamide 38-1 (0.069 g, 0.39 mmol) were suspended in chloroform/2M $Na_2CO_3$ in a sealed tube and heated in a Smith Personal Chemistry microwave reactor at 100° C. for 20 minutes. The solid was then filtered off and purified on a silica column to afford 38-2. Hi-Res MS: calc: 385.1554 found: 385.1548. $^1$H-NMR (CD$_3$OD): 8.39(s, 1H); 7.99(s, 1H); 6.14(s, 1H); 3.68(m, 4H); 3.05(s, 2H); 2.70(m, 1H); 2.58(m, 4H); 0.75(m, 2H); 0.55(m, 2H).

SCHEME 39

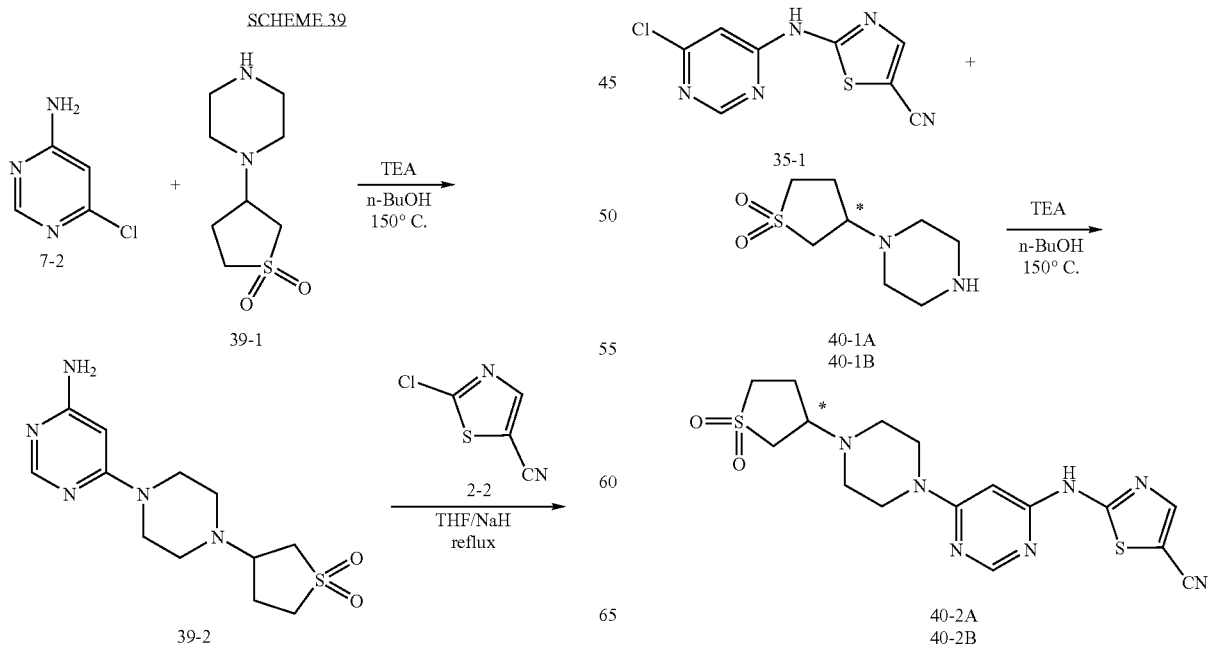

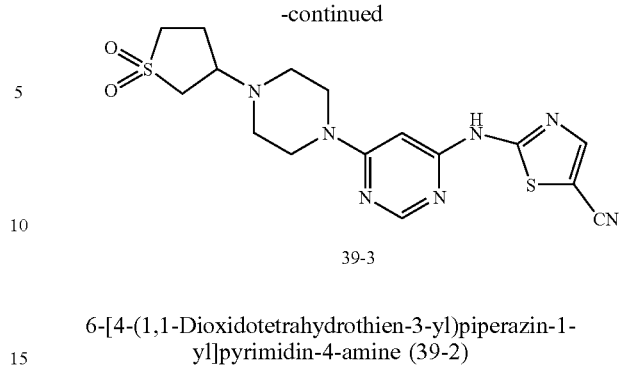

6-[4-(1,1-Dioxidotetrahydrothien-3-yl)piperazin-1-yl]pyrimidin-4-amine (39-2)

7-2 (0.23 g, 1.79 mmol), DIEA (0.69 g, 5.37 mmol) and 1-(1,1-dioxidotetrahydrothien-3-yl)piperazinediium dichloride (the bis HCl salt of 39-1) (0.49 g, 1.79 mmol) were stirred at 150° C. in n-butanol for 18 hours overnight. Upon cooling, the solid was filtered off and washed with n-butanol and ethyl ether to afford 39-2. Hi-Res MS: calc: 298.1132 found: 298.1357. $^1$H-NMR (CD$_3$OD): 7.97(s, 1H); 5.72(s, 1H); 3.55(t, 4H); 3.27(complex, 2H); 3.07(complex, 2H); 2.77(complex, 1H); 2.67(m, 2H); 2.59(m, 2H); 2.47(m, 1H); 2.12(m, 1H).

(+/−)-2-({6-[4-(1,1-Dioxidotetrahydrothien-3-yl)piperazin-1-yl]pyrimidin-4-yl}amino)-1,3-thiazole-5-carbonitrile (39-3)

6-[4-(1,1-Dioxidotetrahydrothien-3-yl)piperazin-1-yl]pyrimidin-4-amine 39-2 (0.30 g, 1.01 mmol), sodium hydride (0.081 g, 2.02 mmol) and 2-chloro-1,3-thiazole-5-carbonitrile 2-2 (0.14 g, 1.01 mmol) were treated as in Scheme 4 above. The product was purified on a $C_{18}$ column. Hi-Res MS: calc: 406.1114 found: 406.1105. $^1$H-NMR: 8.46(s, 1H); 8.01(s, 1H); 6.24(s, 1H); 3.86(br s, 6H); 3.59(m, 1H); 3.39(m, 1H); 3.27(m, 1H); 3.17(complex, 4H); 2.70(m, 1H); 2.29(m, 1H).

SCHEME 40

(+) and (−)-1-(1,1-Dioxidotetrahydrothien-3-yl)piperazine (40-1A and 40-1B)

The racemic 1-(1,1-dioxidotetrahydrothien-3-yl) was resolved on a Chiralpak AS 5×50 column. The first compound off the column is the (+)-enantiomer, 40-1B. The second compound eluted off the column is the (−)-enantiomer, 40-1A. The absolute configuration of each enantiomer was not determined. $^1$H-NMR (CDCl$_3$, (+)-isomer): 3.26(m, 3H); 3.00–3.09(complex, 2H); 2.95(t, 4H); 2.59(m, 2H); 2.52(m, 2H); 2.42(m, 1H); 2.13(m, 1H). $^1$H-NMR (CDCl$_3$, (−)-isomer): 3.27(m, 3H); 2.98–3.09(complex, 2H); 2.91(t, 4H); 2.54(m, 2H); 2.39–2.48(complex, 3H); 2.13(m, 1H).

2-({6-[4-(1,1-Dioxidotetrahydrothien-3-yl)piperazin-1-yl]pyrimidin-4-yl}amino)-1,3-thiazole-5-carbonitrile (Enantiomer A, 40-2A)

The (−)-isomer of 40-1A (0.15 g, 0.73 mmol) and 35-1 (0.17 g, 0.73 mmol) were dissolved in n-butanol and triethylamine (0.22 g, 2.2 mmol) and heated at 150° C. for 2 hours. The reaction was cooled and the solid was filtered off, washed with n-butanol, ethyl ether and then dried to afford enantiomerically pure 40-2A with an enantiomeric excess greater than 98%. Hi-Res MS: calc: 406.1114 found: 406.1142. $^1$H-NMR (CD$_3$OD): 8.57(s, 1H); 8.10(s, 1H); 6.45(s, 1H); 4.25(m, 2H); 4.08(br s, 3H); 3.72(m, 1H); 3.59(br s, 2H); 3.48(m, 4H); 3.25(m, 1H); 2.83(m, 1H); 2.44(m, 1H). The absolute configuration of this compound was not determined.

2-({6-[4-(1,1-Dioxidotetrahydrothien-3-yl)piperazin-1-yl]pyrimidin-4-yl}amino)-1,3-thiazole-5-carbonitrile (Enantiomer B, 40-2B)

The (+)-isomer of 40-1B (0.16 g, 0.77 mmol) and 35-1 (0.18 g, 0.77 mmol) were dissolved in n-butanol and triethylamine (0.23 g, 2.32 mmol) and heated at 150° C. for 2 hours. The reaction was cooled and the solid was filtered off, washed with n-butanol, ethyl ether and then dried to afford enantiomerically pure 40-2B with an enatiomeric excess greater than 98%. Hi-Res MS: calc: 406.1114 found: 406.1140. $^1$H-NMR (CD$_3$OD): 8.53(s, 1H); 8.07(s, 1H); 6.38(s, 1H); 4.23(m, 2H); 4.04(br s, 3H); 3.72(m, 1H); 3.56(br s, 2H); 3.46(m, 4H); 3.23(m, 1H); 2.83(m, 1H); 2.44(m, 1H). The absolute configuration of this compound was not determined.

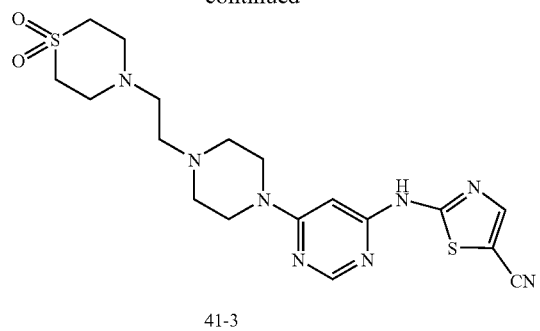

41-3

4-(2-chloroethyl)thiomorpholin-4-ium 1,1-dioxide chloride (41-2)

4-(2-Hydroxyethyl)thiomorpholin-4-ium 1,1-dioxide chloride, the HCl salt of 41-1, (6.0 g, 27.82 mmol) was treated with pyridine (2.43 g, 30.60 mmol) and then warmed with a solution of thionyl chloride (4.96 g, 41.72 mmol) in chloroform (20 mL) to 60° C. After 1.5 hours the reaction was cooled to 25° C. and water was added. The chloroform was drawn off and the aqueous layer was condensed under reduced pressure to a clear syrup which crystallized upon standing. The crystals were filtered off, washed with 95% ethanol, methanol and then dried to afford 41-2. $^1$H-NMR (CD$_3$OD): 4.01(t, 2H); 3.90(m, 4H); 3.71(t, 2H); 3.59(t, 4H).

2-[(6-{4-[2-(1,1-dioxidothiomorpholin-4-yl)ethyl]piperazin-1-yl}pyrimidin-4-yl)amino]-1,3-thiazole-5-carbonitrile (41-3)

12-3 (0.20 g, 0.39 mmol), 41-2 (0.11 g, 0.47 mmol) and DIEA (0.30 g, 2.33 mmol) were suspended in DMF (1 mL) in a sealed tube and heated at 200° C. for 15 minutes in the Smith personal chemistry microwave reactor. The crude material was purified on a C$_{18}$ preparative hplc column to afford 41-3. Hi-Res MS: calc: 449.1576 found: 449.1532. $^1$H-NMR(CD$_3$OD): 8.49(s, 1H); 8.02(s, 1H); 6.28(s, 1H); 4.02(m, 4H); 3.48(br s, 4H); 3.39(t, 2H); 3.16(m, 4H); 3.12(m, 4H); 2.97(m, 2H).

SCHEME 41

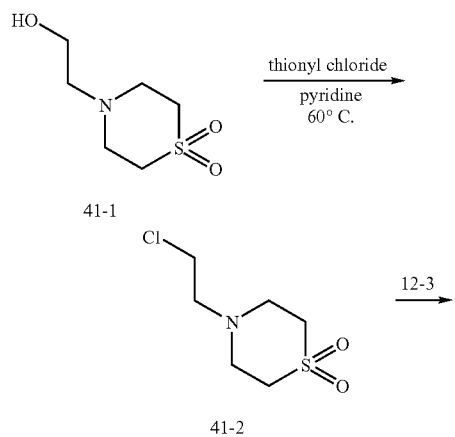

SCHEME 42

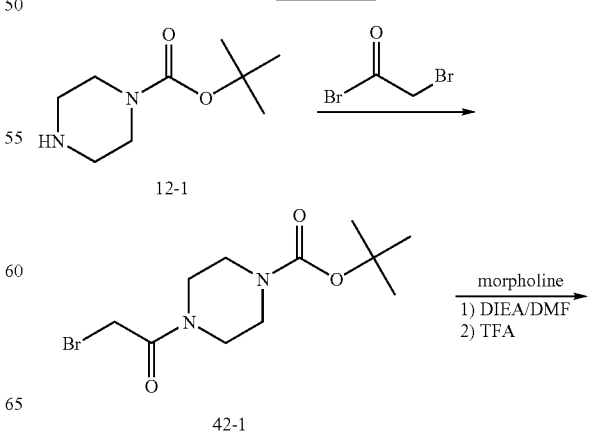

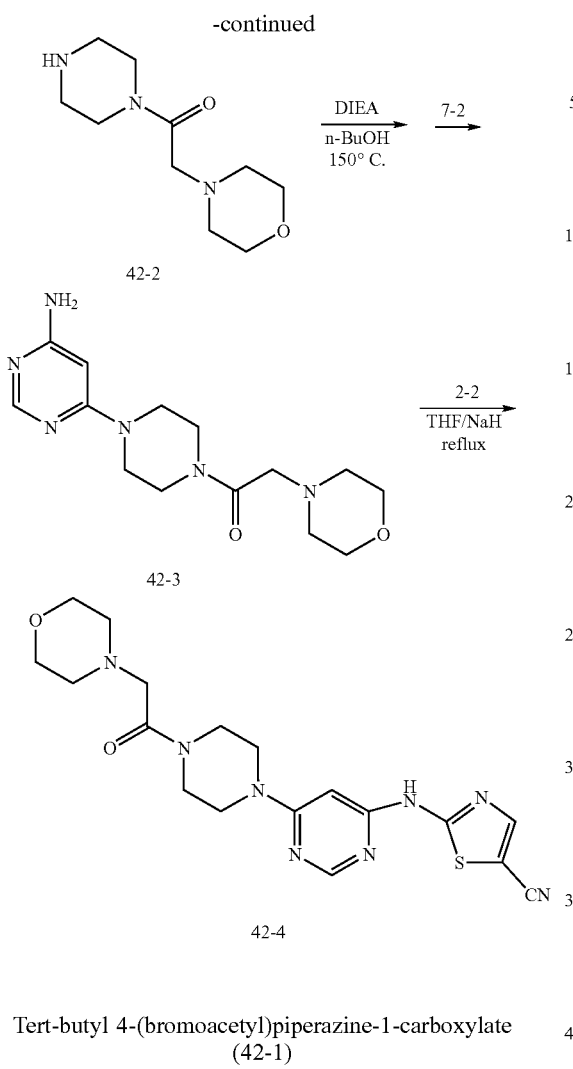

evaporated to dryness, washed the methanol, and the solids filetred off to afford 42-2. $^1$H-NMR(CD$_3$OD): 3.69(t, 4H); 3.59 (t, 2H); 3.54(t, 2H); 3.22(s, 2H); 2.83(t, 2H); 2.77(t, 2H); 2.49(t, 4H).

6-[4-(morpholin-4-ylacetyl)piperazin-1-yl]pyrimidin-4-amine (42-3)

7-2 (0.22 g, 1.76 mmol), 42-2 (0.37 g, 1.76 mmol) and DIEA (0.23 g, 1.76 mmol) were reacted to afford 42-3, which was purified on a silica column. $^1$H-NMR(CD$_3$OD): 8.00(s, 1H); 5.75(s, 1H); 3.70(m, 6H); 3.65(m, 4H); 3.56(m, 2H); 3.30(s, 2H); 2.54(br s, 4H).

2-({6-[4-(morpholin-4-ylacetyl)piperazin-1-yl]pyrimidin-4-yl}amino)-1,3-thiazole-5-carbonitrile (42-4)

42-3 (0.36 g, 1.18 mmol), sodium hydride (0.094 g, 2.35 mmol) and 2-chloro-1,3-thiazole-5-carbonitrile 2-2 (0.17 g, 1.18 mmol) were treated as in Scheme 4 above. The reaction was cooled, quenched with methanol and water, evaporated to dryness and partitioned between methylene chloride, methanol and water. The organic layers were evaporated to dryness and purified on a C$_{18}$ preparative hplc column and isolated via lyophilization to afford 42-4. Hi-Res MS: calc: 415.1659 found: 415.1638. $^1$H-NMR (CD$_3$OD): 8.44(s, 1H); 8.01(s, 1H); 6.20(s, 1H); 4.36(s, 2H); 4.05(br s, 2H); 3.88(br s, 2H); 3.82(m, 2H); 3.76(m, 2H); 3.71(m, 2H); 3.56(m, 4H); 3.25(br s, 2H).

SCHEME 43

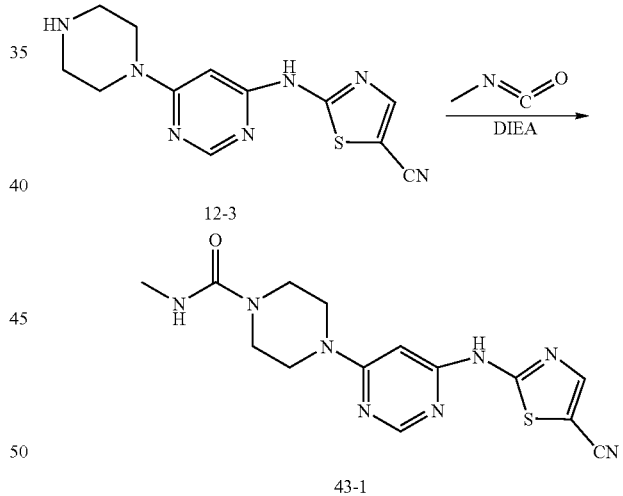

Tert-butyl 4-(bromoacetyl)piperazine-1-carboxylate (42-1)

A solution of bromoacetyl bromide (0.59 g, 2.95 mmol) in methylene chloride (3 mL) was added drop wise via addition funnel to a stirred solution of tert-butyl piperazine-1-carboxylate 12-1 (0.50 g, 2.68 mmol) and aqueous sodium carbonate (0.34 g, 3.22 mmol) in methylene chloride (15 mL) at 0° C. After a 10 minute reaction time the methylene chloride layer was drawn off, dried and evaporated to an oil. This was purified this on a silica column to afford 42-1. Hi-Res MS (M+Na): calc: 329.0471 found: 329.0462. $^1$H-NMR(CDCl$_3$): 3.87(s, 2H); 3.61(m, 2H); 3.52(m, 2H); 3.50(m, 2H); 3.44(m, 2H); 1.47(s, 9H).

4-(2-Oxo-2-piperazin-1-ylethyl)morpholine (42-2)

Morpholine (0.22 g, 2.59 mmol), 42-1 (0.61 g, 1.99 mmol) and DIEA (0.33 g, 2.59 mmol) were dissolved in DMF (2 mL) and stirred for 18 hours at room temperature. The DMF was then removed under reduced pressure and the residue partitioned between water and methylene chloride. The methylene chloride was drawn off, dried and evaporated to a solid to afford 42-2. This recovered product was treated with neat trifluoroacetic acid and the excess trifluoroacetic acid evaporated off. The resulting residue was partitioned between methylene chloride and aqueous Na$_2$CO$_3$. The free base did not extract from the aqueous so the aqueous was 4-{6-[(5-Cyano-1,3-thiazol-2-yl)amino]pyrimidin-4-yl}-N-methylpiperazine-1-carboxamide (43-1)

12-3 (0.25 g, 0.88 mmol) was dissolved in a minimal amount of DMF (2 mL) and DIEA (0.57 g, 4.38 mmol) before it was diluted with methylene chloride (5 mL). Then a methylene chloride solution (1 mL) of methylisocyanate (0.050 g, 0.88 mmol) was added. A precipitate quickly formed and was filtered off, washed with methylene chloride and air dried to afford 43-1. Hi-Res MS: calc: 345.1241 found: 345.1269. $^1$H-NMR (DMSO-d$_6$): 12.09(s, 1H); 8.44 (s, 1H); 8.26(s, 1H); 6.52(d, 1H); 6.21(s, 1H); 3.54(m, 4H); 3.40(m, 4H); 2.58(d, 3H).

SCHEME 44

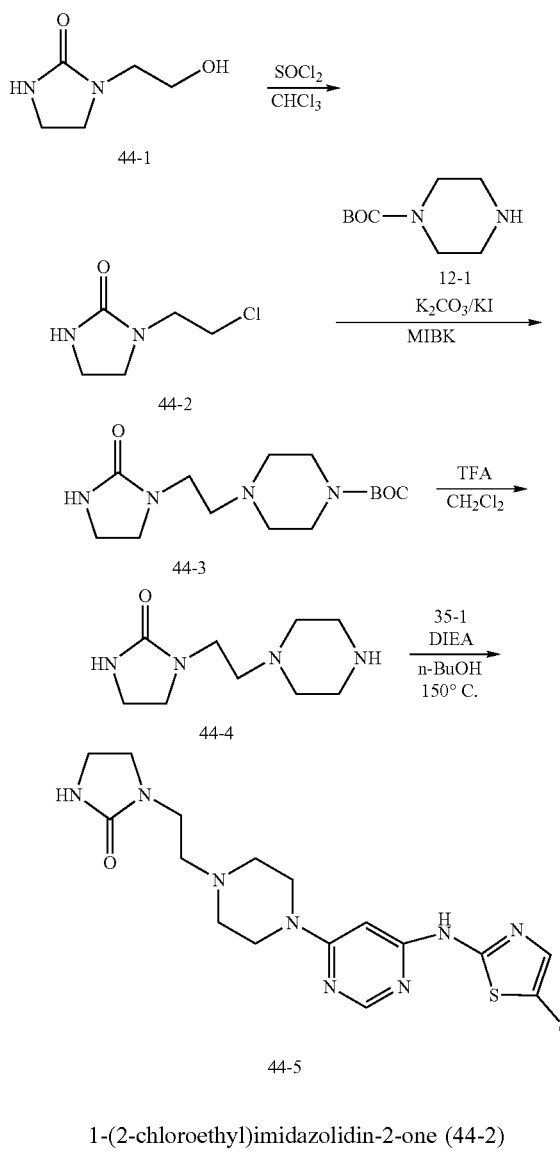

1-(2-chloroethyl)imidazolidin-2-one (44-2)

A solution of 5.00 g (38.42 mmol) of 1-(2-hydroxyethyl)imidazolidin-2-one 44-1 and 3.82 mL (52.39 mmol) of thionyl chloride in 75 mL of chloroform was stirred at reflux for 4 hours. The reaction was concentrated in vacuo to an orange oil, which was redissolved in chloroform and washed twice with water. The organic layer was dried and reconcentrated to give the crude desired product as an orange solid. The solid was used as obtained from the reaction without further purification.

1-(2-piperazin-1-ylethyl)imidazolidin-2-one (44-4)

A mixture of 2.00 g (13.46 mmol) of 44-2, 1.25 g (6.73 mmol) of 1-boc-piperazine, 1.60 g (11.58 mmol) of potassium carbonate, and 0.10 g (catalytic amount) of KI in 30 mL of methyl isobutylketone was stirred at reflux for 48 hours. The reaction was filtered while hot, and the filtrate concentrated in vacuo to a solid. The solid was purified by flash chromatography over silica gel with 10% MeOH/CHCl$_3$ eluent to afford 44-3 as an off-white solid. A 0.75 g sample of this solid was dissolved in 2 mL methylene chloride/2 mL TFA, and the solution stirred at 25° C. for 1 hour. The reaction was concentrated in vacuo to give the bis TFA salt of the desired product 44-4 as a brown oil. FAB MS: M+1=198.

2-[(6-{4-[2-(2-oxoimidazolidin-1-yl)ethyl]piperazin-1-yl}pyrimidin-4-yl)amino]-1,3-thiazole-5-carbonitrile (44-5)

35-1 (0.25 g, 1.06 mmol), 44-4 (0.21 g, 1.06 mmol) and DIEA (0.69 g, 5.32 mmol) were heated at 150° C. for 3 hours in n-butanol. Upon cooling the precipitate was filtered off, washed with n-butanol and ethyl ether and then dried to afford 44-5. Hi-Res MS: calc: 400.1663 found: 400.1633. $^1$H-NMR (CD$_3$OD): 8.38(s, 1H); 7.99(s, 1H); 6.14(s, 1H); 3.65(m, 4H); 3.55(m, 2H); 3.39(m, 2H); 3.35(t, 2H); 2.59 (complex, 6H).

SCHEME 45

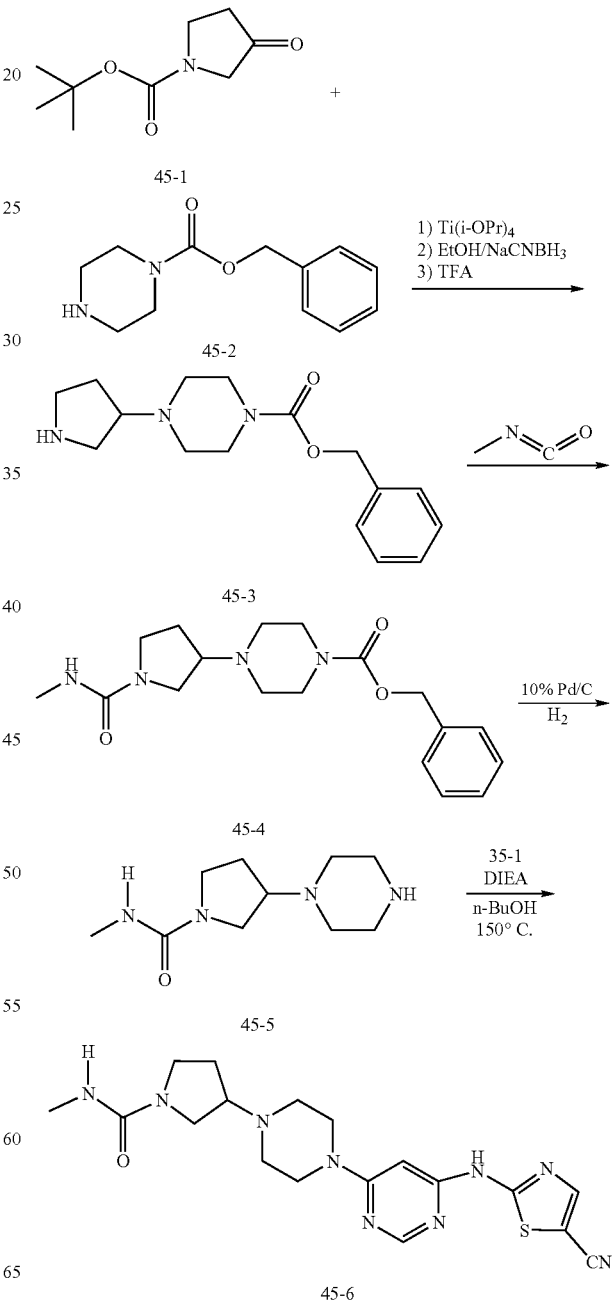

Benzyl 4-pyrrolidin-3-ylpiperazine-1-carboxylate (45-3)

A mixture of tert-butyl 3-oxopyrrolidine-1-carboxylate 45-1 (0.32 g, 1.73 mmol)), benzyl piperazine-1-carboxylate 45-2 (0.38 g, 1.73 mmol) and titanium tetraisopropoxide (0.61 g, 2.16 mmol) were stirred at 25° C. for 1 hour. Then the viscous solution was diluted with 2 mL of absolute ethanol and sodium cyanoborohydride (0.073 g, 1.16 mmol) was added. After stirring for 18 hours at 25° C., 1 mL of water was added and the solids filtered off. The filtrate was then dried under reduced pressure, redissolved in ethyl acetate, refiltered and evaporated. This material was purified on a silica column and then treated with trifluoroacetic acid to afford 45-3. $^1$H-NMR (CDCl$_3$): 7.36(m, 5H); 5.13(s, 2H); 3.55(m, 4H); 3.26(m, 1H); 3.08(m, 1H); 2.80(m, 1H); 2.62 (m, 1H); 2.49(m, 2H); 2.41(m, 2H); 2.08(m, 2H); 1.75(m, 1H).

Benzyl 4-{1-[(methylamino)carbonyl]pyrrolidin-3-yl}piperazine-1-carboxylate (45-4)

45-3 (0.27 g, 0.93 mmol) was dissolved in methylene chloride (4 mL) and DIEA (0.60 g, 4.67 mmol) and then a methylene chloride solution (1 mL) of methylisocyanate (0.050 g, 0.93 mmol) was added. The solution was then stirred for 30 minutes, after which it was concentrated and purified on a C$_{18}$ preparative hplc column to afford 45-4. $^1$H-NMR (CD$_3$OD): 7.37(m, 5H); 5.17(s, 2H); 3.89(m, 4H); 3.59(m, 4H); 3.36(m, 5H); 2.74(s, 3H); 2.47(m, 1H); 2.24 (m, 1H).

N-methyl-3-piperazin-1-ylpyrrolidine-1-carboxamide (45-5)

45-4 (0.10 g, 0.30 mmol) was dissolved in 10 mL of absolute ethanol. To this solution was added 10% Pd/C catalyst. This was then hydrogenolyzed for 7 hours at 60 psi. The catalyst was then filtered off and the filtrate was evaporated to an oil and flushed with methanol to afford 45-5. $^1$H-NMR (CD$_3$OD): 3.62(m, 2H); 3.49(m, 2H); 3.24(t, 4H); 3.14(m, 1H); 3.03(m, 1H); 2.82(m, 2H); 2.72(complex, 4H); 2.20(m, 1H); 1.86(m, 1H).

3-(4-{6-[(5-Cyano-1,3-thiazol-2-yl)amino]pyrimidin-4-yl}piperazin-1-yl)-N-methylpyrrolidine-1-carboxamide (45-6)

35-1 (0.106 g, 0.45 mmol), 45-5 (0.095 g, 0.45 mmol) and DIEA (0.18 g, 1.79 mmol) were heated at 150° C. for 3 hours in n-butanol. Upon cooling the precipitate was filtered off, washed with n-butanol and ethyl ether and then dried to afford 45-6. Hi-Res MS: calc: 414.1819 found: 414.1827. $^1$H-NMR (DMSO-d$_6$): 12.08(s, 1H); 8.42(s, 1H); 8.26(s, 1H); 6.22(s, 1H); 6.02(d, 1H); 3.55(m, 4H); 3.38 (m, 1H); 3.13(m, 1H); 2.97(m, 1H); 2.78(m, 1H); 2.50(complex, 6H); 2.45(m, 2H); 2.06(m, 1H); 1.69(m, 1H).

SCHEME 46

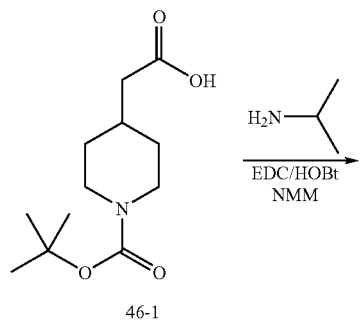

46-1

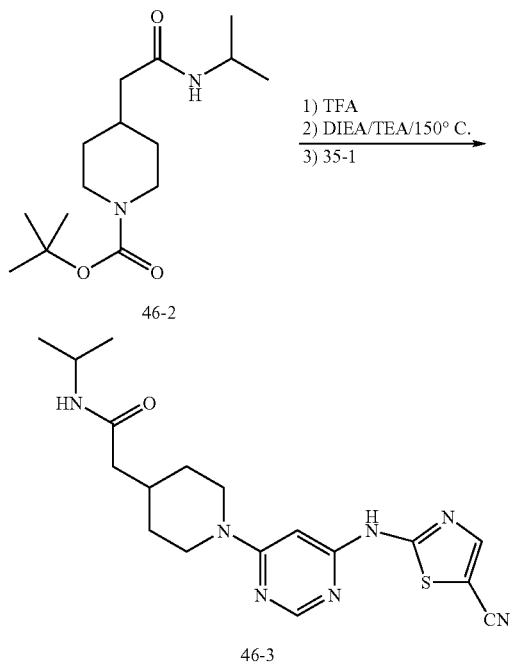

Tert-butyl 4-[2-(isopropylamino)-2-oxoethyl]piperidine-1-carboxylate (46-2)

[1-(Tert-butoxycarbonyl)piperidin-4-yl]acetic acid 46-1 (0.20 g, 0.82 mmol), 1-hydroxybenzotriazole (0.15 g, 0.99 mmol), N-[3-(dimethylamino)propyl]-N'-ethylcarbodiimide hydrochloride (0.21 g, 1.07 mmol), 4-methylmorpholine (0.33 g, 3.29 mmol) and isopropyl amine (0.053 g, 0.90 mmol) were dissolved in DMF and stirred at 25° C. for 18 hours. Evaporated off the DMF and partitioned between ethyl acetate and dilute KHSO$_4$. The aqueous was drawn off and the organic was washed with dilute NaHCO$_3$, brine, dried, filtered and evaporated to afford 46-2. $^1$H-NMR (CD$_3$OD): 4.03(d, 2H); 3.95(m, 1H); 2.75(br s, 2H); 2.06(d, 2H); 1.91(m, 1H); 1.64 (d, 2H); 1.44(s, 9H); 1.12(complex, 8H).

2-(1-{6-[(5-Cyano-1,3-thiazol-2-yl)amino]pyrimidin-4-yl}piperidin-4-yl)-N-isopropylacetamide (46-3)

46-2 (0.21 g, 0.73 mmol) was treated with neat trifluoroacetic acid for 20 minutes and then the trifluoroacetic acid was evaporated off. This residue and 35-1 (0.17 g, 0.73 mmol) and triethylamine (0.37 g, 3.67 mmol) were heated at 150° C. for 3 hours in n-butanol. Upon cooling the precipitate was filtered off, washed with n-butanol and ethyl ether and then dried to afford 46-3. Hi-Res MS: calc: 386.1758 found: 386.1754. $^1$H-NMR (CD$_3$OD): 8.36(s, 1H); 7.99(s, 1H); 6.14(s, 1H); 4.40(d, 2H); 3.98(m, 1H); 2.94(t, 2H); 2.10(complex, 3H); 1.77(d, 2H); 1.22(m, 2H); 1.13(d, 6H).

SCHEME 47

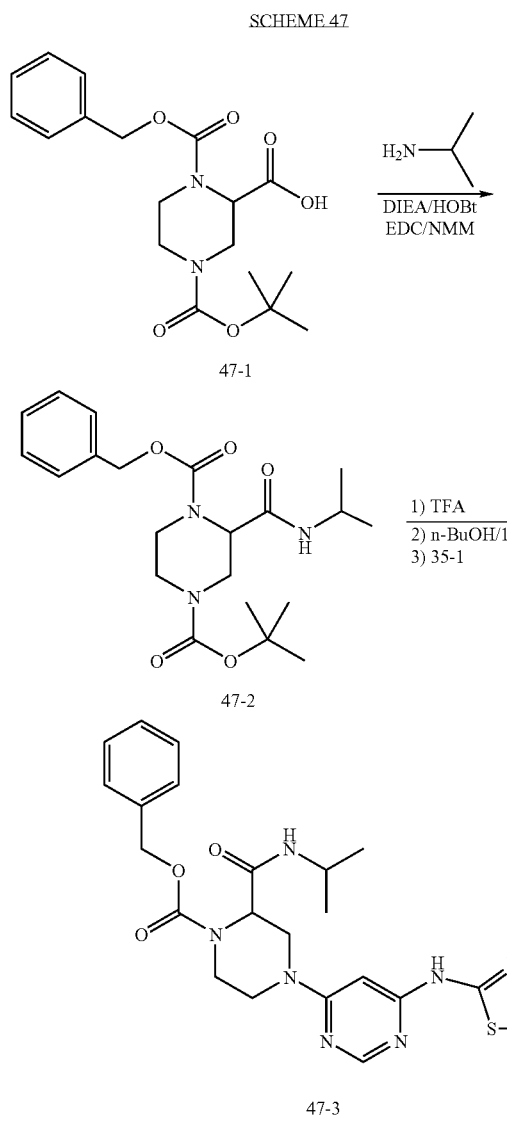

1-benzyl 4-tert-butyl 2-[(isopropylamino)carbonyl]piperazine-1,4-dicarboxylate (47-2)

1-[(benzyloxy)carbonyl]-4-(tert-butoxycarbonyl)piperazine-2-carboxylic acid 47-1 (0.40 g, 1.10 mmol), 1-hydroxybenzotriazole (0.20 g, 1.32 mmol), N-[3-(dimethylamino)propyl]-N'-ethylcarbodiimide hydrochloride (0.27 g, 1.43 mmol), 4-methylmorpholine (0.0.44 g, 4.39 mmol) and isopropyl amine (0.071 g, 1.21 mmol) were dissolved in DMF and stirred at 25° C. for 18 hours. The DMF was then removed under reduced pressure and the residue partitioned between ethyl acetate and dilute aqueous KHSO₄. The aqueous phase was drawn off and the organic layer was washed with dilute aqueous NaHCO₃, brine, dried, filtered and evaporated to afford 47-2.

Benzyl 4-{6-[(5-cyano-1,3-thiazol-2-yl)amino]pyrimidin-4-yl}-2-[(isopropylamino)carbonyl]piperazine-1-carboxylate (47-3)

47-2 (0.24 g, 0.78 mmol) was first treated with 3 mL of trifluoroacetic acid for 30 minutes at 25° C. and then the reaction was evaporated to dryness. The residue was dissolved in n-butanol and 35-1 (0.18 g, 0.78 mmol) and triethylamine (0.39 g, 3.88 mmol) were added. After heating at 150° C. for 18 hours, the reaction was cooled and the product was filtered off, washed with n-butanol, ethyl ether and then dried to afford the product 47-3. Hi-Res MS: calc: 507.1921 found: 507.1914. $^1$H-NMR (DMSO-$d_6$): 12.15(s, 1H); 8.39(s, 1H); 8.25(s, 1H); 7.33(m, 5H); 6.11(s, 1H); 5.14(m, 2H); 4.47(m, 2H); 3.85(m, 2H); 3.69(m, 2H); 3.25 (m, 1H); 3.17(m, 1H); 0.93(m, 6H).

SCHEME 48

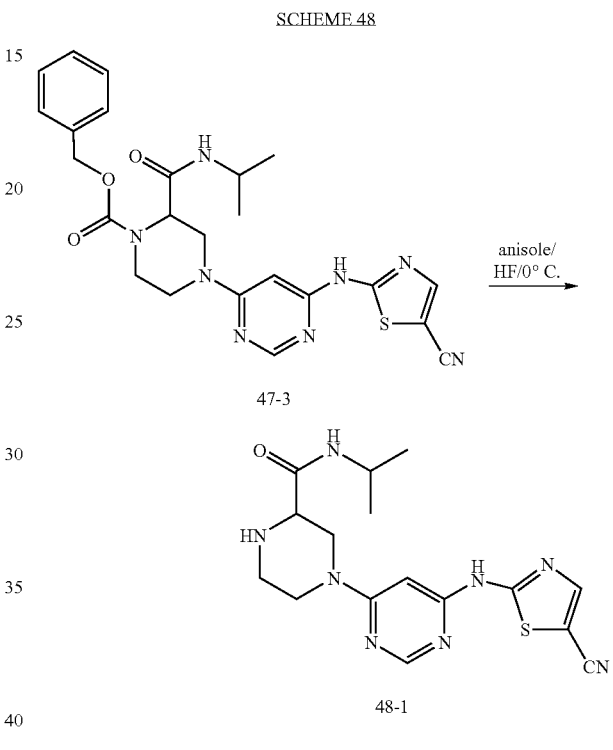

4-{6-[(5-Cyano-1,3-thiazol-2-yl)amino]pyrimidin-4-yl}-N-isopropylpiperazine-2-carboxamide (48-1)

47-3 (0.23 g, 0.46 mmol) was wetted with 1 mL of anisole before treatment with 10 mL of hydrofluoric acid for 1 hour at 0° C. The hydrofluoric acid was then evaporated off and the residue was suspended in ethyl ether, filtered and then purified on a silica column to give 48-1. Hi-Res MS: calc: 373.1554 found: 373.1550. $^1$H-NMR (CD$_3$OD): 8.40(s, 1H); 7.99(s, 1H); 6.17(s, 1H); 4.30(d, 1H); 3.98(m, 2H); 3.37(m, 1H); 3.18(m, 2H); 3.06(m, 1H); 2.82(m, 1H); 1.16(m, 6H).

SCHEME 49

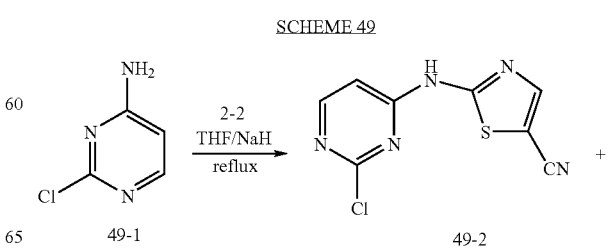

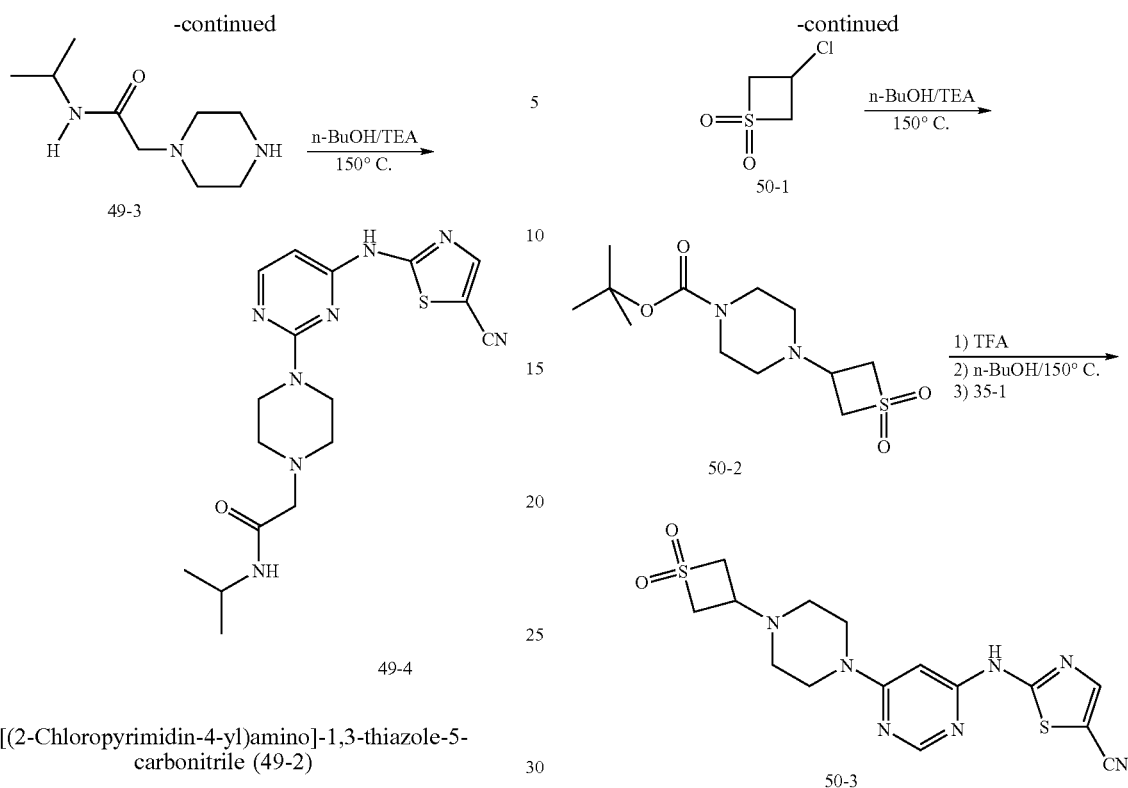

2-[(2-Chloropyrimidin-4-yl)amino]-1,3-thiazole-5-carbonitrile (49-2)

2-Chloropyrimidin-4-amine 49-1 (0.30 g, 2.32 mmol) and sodium hydride (0.093 g, 2.32 mmol) were suspended in dry THF and stirred for 20 minutes before adding 2-chloro-1,3-thiazole-5-carbonitrile 2-2 (0.33 g, 2.32 mmol) and more sodium hydride (0.093 g, 2.32 mmol) simultaneously. This was refluxed for 1.5 hour and then quenched with methanol and water, and concentrated to dryness. The residue was partitioned between DCM, MeOH, and water. The aqueous layer was evaporated to dryness and then purified on a silica column. $^1$H-NMR (CD$_3$OD): 8.50(d, 1H); 8.42(s, 1H); 7.11 (d, 1H). By $^1$H-NMR this material is a mixture of the desired product and 2-chloropyrimidin-4-amine in a ratio of 5:8, which was used as is in the next step.

2-(4-{4-[(5-Cyano-1,3-thiazol-2-yl)amino]pyrimidin-2-yl}piperazin-1-yl)-N-isopropylacetamide (49-4)

N-isopropyl-2-piperazin-1-ylacetamide 49-3 (0.15 g, 0.80 mmol), 49-4 (0.19 g, 0.80 mmol) and triethylamine (0.40 g, 3.99 mmol) were heated at 150° C. for 2 hours in 4 mL of n-butanol. Upon cooling, the solid was filtered off, washed with n-butanol, ethyl ether and then dried to afford 49-4. Hi-Res MS: calc: 387.1710 found: 387.1699. $^1$H-NMR (DMSO-d$_6$): 12.14(s, 1H); 8.31(s, 1H); 8.16(d, 1H); 7.54(d, 1H); 6.31(d, 1H); 3.86(complex, 5H); 2.95(br s, 2H); 2.54 (br s, 4H); 1.09(m, 6H).

SCHEME 50

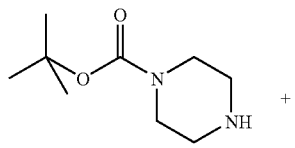

Tert-butyl 4-(1,1-dioxidothietan-3-yl)piperazine-1-carboxylate (50-2)

3-Chlorothietane 1,1-dioxide 50-1 (0.50 g, 3.56 mmol) was dissolved in n-butanol (4 mL) then triethylamine (1.08 g, 10.67 mmol) was added followed by tert-butyl piperazine-1-carboxylate 12-1 (0.66 g, 3.56 mmol). This was then stirred at 150° C. for 5 hours. Upon cooling the solid was filtered off, washed with n-butanol, ethyl ether and then purified on a silica column to afford 50-2. $^1$H-NMR (CDCl$_3$): 4.10(complex, 4H); 3.46(t, 4H); 3.19(m, 1H); 2.36(t, 4H); 1.46(s, 9H).

2-({6-[4-(1,1-Dioxidothietan-3-yl)piperazin-1-yl]pyrimidin-4-yl}amino)-1,3-thiazole-5-carbonitrile (50-3)

50-2 (0.20 g, 0.68 mmol) was first treated with trifluoroacetic acid (4 mL) for 30 minutes and then concentrated under reduced pressure. The residue was then dissolved in n-butanol (4 mL) to which 35-1 (0.16 g, 0.68 mmol) and triethylamine (0.34 g, 3.41 mmol) were added and then heated at 150° C. for 18 hours. Upon cooling the solid was filtered off, washed with n-butanol, ethyl ether and then purified on a silica column to yield 50-3. Hi-Res MS: calc: 392.0958 found: 392.0949. $^1$H-NMR (DMSO-d$_6$): 12.10(s, 1H); 8.43(s, 1H); 8.26(s, 1H); 6.24(s, 1H); 4.28(m, 2H); 4.15(m, 2H); 3.57(br s, 4H); 3.22(m, 1H); 2.46(t, 4H).

1H); 7.44 (s, 1H); 6.20 (s, 1H); 3.51 (br s, 4H); 3.13 (m, 1H); 3.05 (m, 2H); 2.93 (m, 2H); 2.63 (m, 2H); 1.62–1.83 (complex, 4H).

SCHEME 51

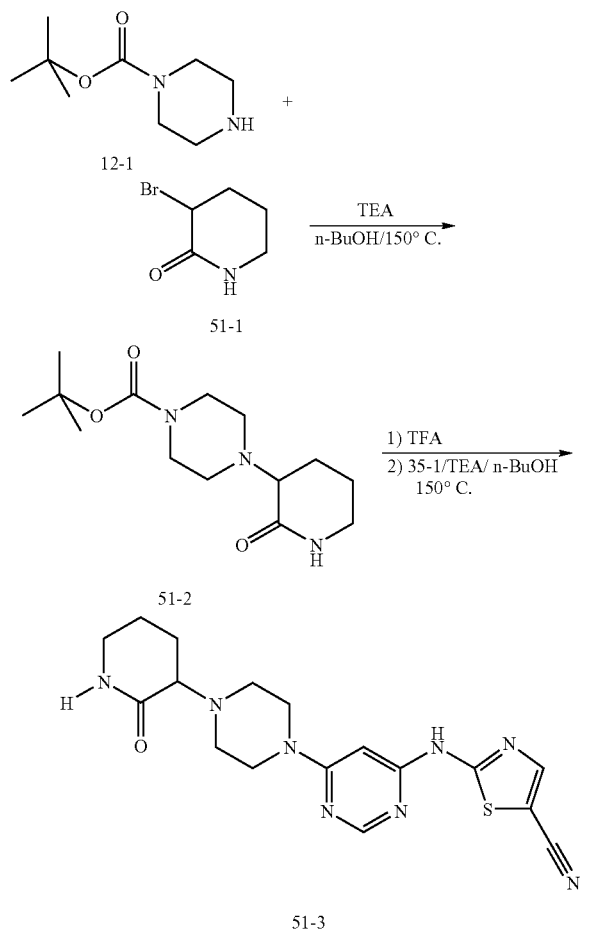

Tert-butyl 4-(2-oxopiperidin-3-yl)piperazine-1-carboxylate (51-2)

3-Bromopiperidin-2-one 51-1 (0.15 g, 0.87 mmol) was dissolved in n-butanol (4 mL) then triethyl amine (0.26 g, 2.60 mmol) was added followed by tert-butyl piperazine-1-carboxylate 12-1 (0.16 g, 0.87 mmol). This was then stirred at 150° C. for 1.5 hours and then the solid was filtered off, washed with n-butanol and then ethyl ether. Hi-Res MS: calc: 284.1969 found: 284.1966. $^1$H-NMR (CDCl$_3$): 3.45 (br s, 2H); 3.26 (br s, 2H); 3.13 (complex, 3H); 2.74(m, 1H); 2.62(m, 1H); 1.98(m, 1H); 1.77(m, 1H); 1.55(complex, 3H); 1.45(t, 9H).

2-({6-[4-(2-Oxopiperidin-3-yl)piperazin-1-yl]pyrimidin-4-yl}amino)-1,3-thiazole-5-carbonitrile (51-3)

51-2 (0.15 g, 0.53 mmol) was first treated with neat trifluoroacetic acid for 30 minutes at room temperature. The trifluoroacetic acid was then evaporated off and the residue was dissolved in n-butanol (3 mL). To this was added 35-1 (0.13 g, 0.53 mmol) and triethylamine (0.27 g, 2.65 mmol). This was heated at 150° C. for 18 hours and then the solid was filtered off, washed with n-butanol and then ethyl ether to afford 51-3. Hi-Res MS: calc: 385.1554 found: 385.1551. $^1$H-NMR (DMSO-d$_6$): 12.02 (s, 1H); 8.41 (s, 1H); 8.25 (s,

SCHEME 52

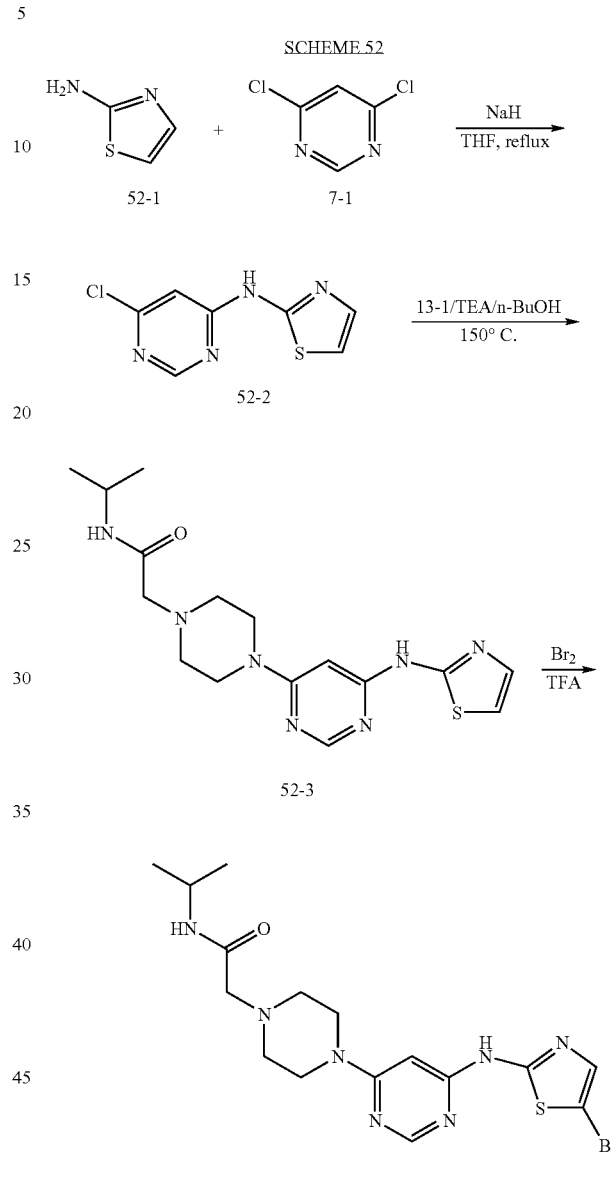

6-Chloro-N-(1,3-thiazol-2-yl)pyrimidin-4-amine (52-2)

1,3-Thiazol-2-amine 52-1 (2.0 g, 20.0 mmol) was dissolved in THF and 1 equivalent of sodium hydride (0.8 g, 60% dispersion in oil) was added. This was stirred for 30 min at room temperature. Then 4,6-dichloropyrimidine 7-1 (2.97 g, 20.0 mmol) and the other equivalent of sodium hydride were added simultaneously. This was refluxed for 30 minutes. The reaction was quenched with methanol and water and then evaporated. The residue was partitioned with DCM:MeOH:water (50:5:50). The organic layer was drawn off, dried and evaporated to afford crude material which was purified on a silica column eluted with 99:1:0.1 (DCM:

MeOH:NH₄OH). $R_f$=0.4 (DCM:MeOH:NH4OH 98:2:0.2). ¹H-NMR(DMSO-d₆): 11.96 (s, 1H); 8.71(s, 1H); 7.49(d, 1H); 7.25(d, 1H); 7.13(br s, 1H).

N-isopropyl-2-{4-[6-(1,3-thiazol-2-ylamino)pyrimidin-4-yl]piperazin-1-yl}acetamide (52-3)

N-isopropyl-2-piperazin-1-ylacetamide 13-1 (0.74 g, 4.0 mmol)) was suspended in n-butanol to which compound 52-2 (0.85 g, 4.0 mmol) and triethylamine (1.22 g, 12.0 mmol) were added and then heated at 150° C. for 6 hours. The reaction was cooled to room temperature and the precipitate was filtered off, washed with n-butanol and ethyl ether and dried to produce 52-3. $R_f$=0.45 (DCM:MeOH: NH₄OH, 95:5:0.5). ¹H-NMR (DMSO-d₆): 11.16(s, 1H); 8.33(s, 1H); 7.54(d, 1H); 7.36(s, 1H); 7.05(s, 1H); 6.24(s, 1H); 3.90(m, 1H); 3.55(br s, 4H); 2.94(s, 2H); 2.49(br s, 4H); 1.08(d, 6H).

2-(4-{6-[(5-Bromo-1,3-thiazol-2-yl)amino]pyrimidin-4-yl}piperazin-1-yl)-N-isopropylacetamide (52-4)

Compound 52-3 (0.96 g, 2.66 mmol) was stirred in 30 mL trifluoroacetic acid. The bromine solution (0.582M in trifluoroacetic acid) was added to the thiazole solution until no further product would form as followed by lc/ms. The TFA was evaporated off and the residue was flushed with methanol and passed through a C18 preparative lc column. The product was isolated and desalted by passing it through a silica column to yield 52-4 as the free base. Hi-Res MS: calc: 440.0863 found: 440.0867. ¹H-NMR (DMSO-d₆): 11.42(s, 1H); 8.34(s, 1H); 7.54(d, 1H); 7.44(s, 1H); 6.14(s, 1H); 3.90(m, 1H); 3.54(br s, 4H); 2.94(s, 2H); 2.50(br s, 4H); 1.08(d, 6H).

The following compounds, 53-1 through 53-13, were made via simple modifications of the procedures described above.

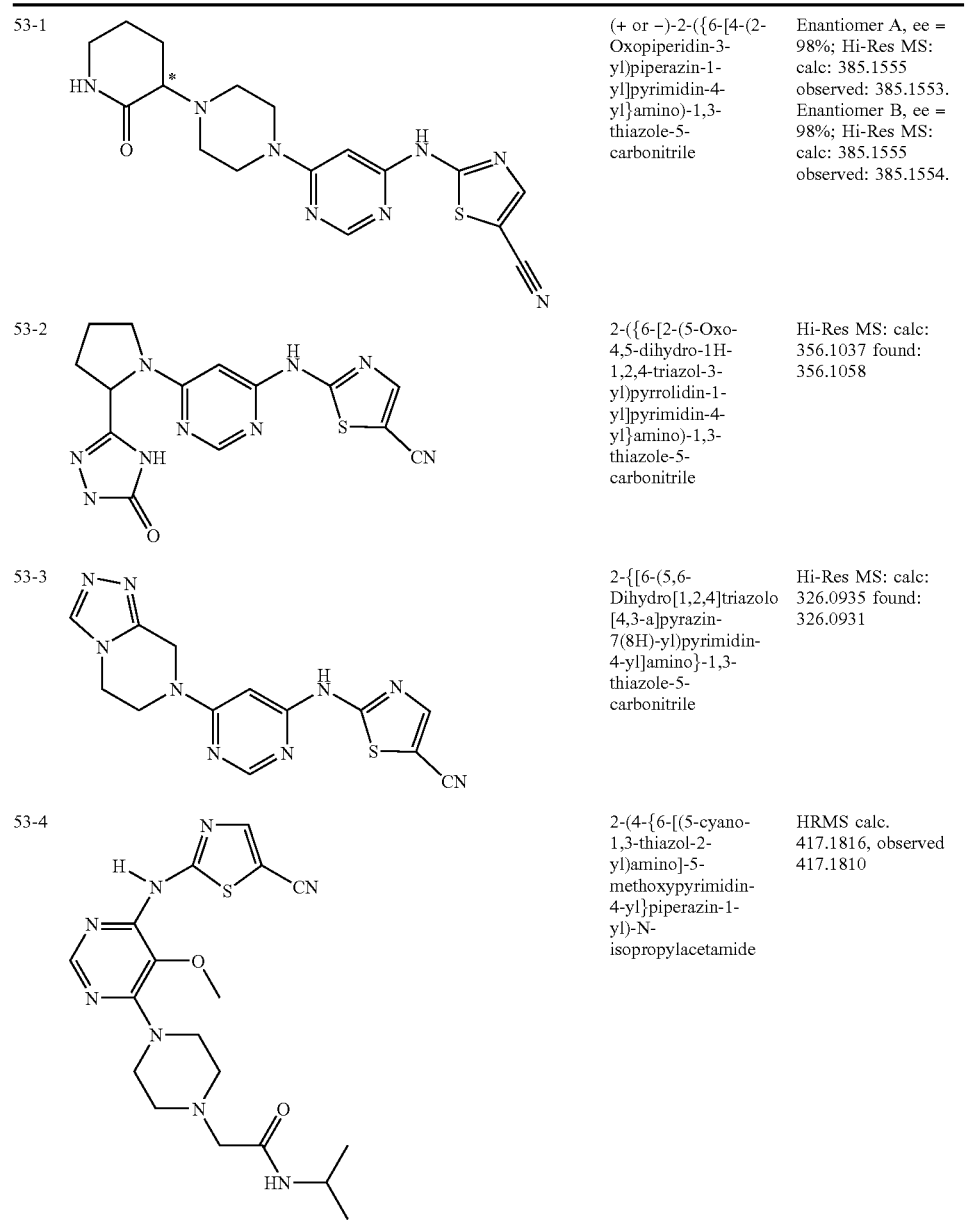

| | | | |
|---|---|---|---|
| 53-1 | | (+ or −)-2-({6-[4-(2-Oxopiperidin-3-yl)piperazin-1-yl]pyrimidin-4-yl}amino)-1,3-thiazole-5-carbonitrile | Enantiomer A, ee = 98%; Hi-Res MS: calc: 385.1555 observed: 385.1553. Enantiomer B, ee = 98%; Hi-Res MS: calc: 385.1555 observed: 385.1554. |
| 53-2 | | 2-({6-[2-(5-Oxo-4,5-dihydro-1H-1,2,4-triazol-3-yl)pyrrolidin-1-yl]pyrimidin-4-yl}amino)-1,3-thiazole-5-carbonitrile | Hi-Res MS: calc: 356.1037 found: 356.1058 |
| 53-3 | | 2-{[6-(5,6-Dihydro[1,2,4]triazolo[4,3-a]pyrazin-7(8H)-yl)pyrimidin-4-yl]amino}-1,3-thiazole-5-carbonitrile | Hi-Res MS: calc: 326.0935 found: 326.0931 |
| 53-4 | | 2-(4-{6-[(5-cyano-1,3-thiazol-2-yl)amino]-5-methoxypyrimidin-4-yl}piperazin-1-yl)-N-isopropylacetamide | HRMS calc. 417.1816, observed 417.1810 |

-continued
| | | | |
|---|---|---|---|
| 53-5 | 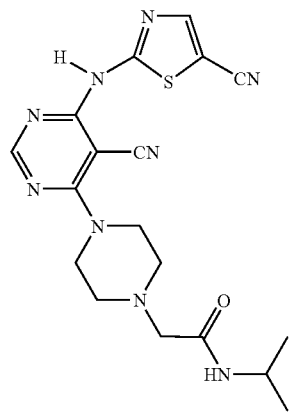 | 2-(4-{5-cyano-6-[(5-cyano-1,3-thiazol-2-yl)amino]pyrimidin-4-yl}piperazin-1-yl)-N-isopropylacetamide | HRMS calc. 412.1663, obs. 412.1640 |
| 53-6 | 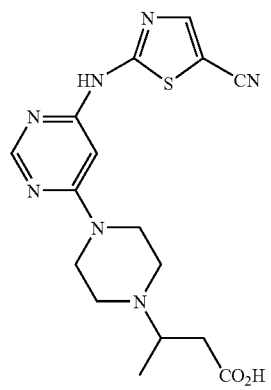 | 3-(4-{6-[(5-cyano-1,3-thiazol-2-yl)amino]pyrimidin-4-yl}piperazin-1-yl)butanoic acid | HRMS calc. 374.1394, obs. 374.1398 |
| 53-7 | 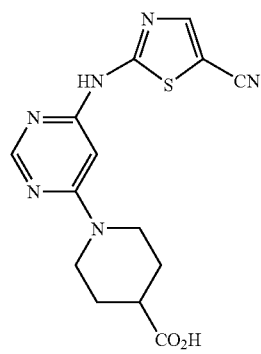 | 1-{6-[(5-cyano-1,3-thiazol-2-yl)amino]pyrimidin-4-yl}piperidine-4-carboxylic acid | HRMS calc. 331.0972, obs. 331.0980 |
| 53-8 | 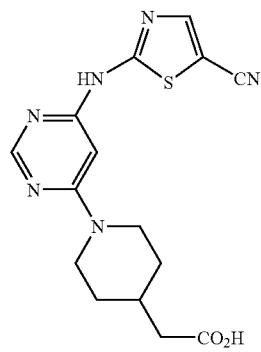 | (1-{6-[(5-cyano-1,3-thiazol-2-yl amino]pyrimidin-4-yl}piperidin-4-yl)acetic acid | FAB MS: M + 1 = 345 |

-continued

| | | | |
|---|---|---|---|
| 53-9 | 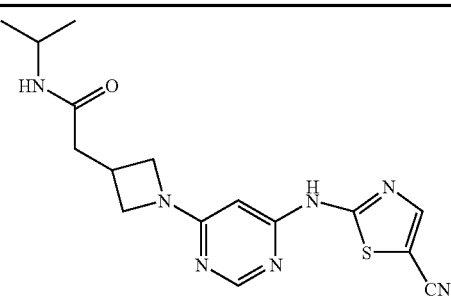 | 2-(1-{6-[(5-cyano-1,3-thiazol-2-yl)amino]pyrimidin-4-yl}azetidin-3-yl)-N-isopropyl acetamide | Hi-Res MS: calc: 358.1445 found: 358.1449 |
| 53-10 | 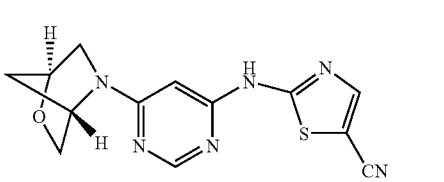 | 2-({6-[(1S,4S)-2-oxa-5-azabicyclo[2.2.1]hept-5-yl]pyrimidin-4-yl}amino)-1,3-thiazole-5-carbonitrile | Hi-Res MS: calc: 301.0866 found: 301.0873 |
| 53-11 | 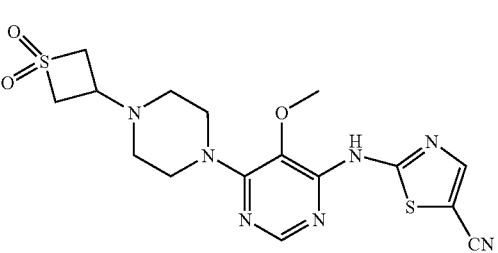 | 2-({6-[4-(1,1-Dioxidothietan-3-yl)piperazin-1-yl]-5-methoxypyrimidin-4-yl}amino)-1,3-thiazole-5-carbonitrile | Hi-Res MS: calc: 422.1064 found: 422.1062 |
| 53-12 | 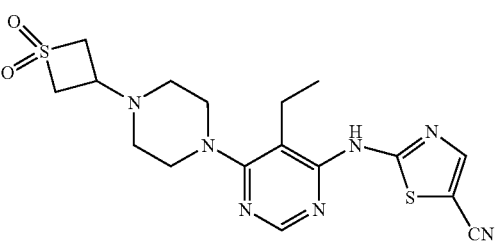 | 2-({6-[4-(1,1-Dioxidothietan-3-yl)piperazin-1-yl]-5-ethylpyrimidin-4-yl}amino)-1,3-thiazole-5-carbonitrile | Hi-Res MS: calc: 420.1271 found: 420.1257 |
| 53-13 | 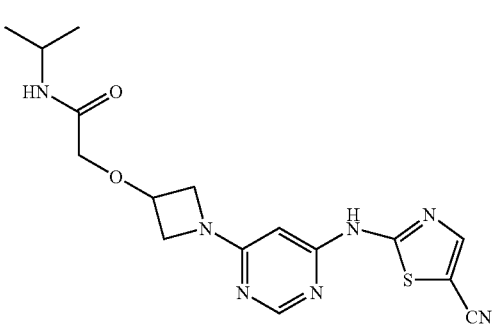 | 2-[(1-{6-[(5-Cyano-1,3-thiazol-2-yl)amino]pyrimidin-4-yl}azetidin-3-yl)oxy]-N-isopropylacetamide | Hi-Res MS: calc: 374.1934 found: 374.1374 |

The corresponding N-oxides of the compounds exemplified above, such as 54-1 through 54-4 shown below, can be readily made by reacting with the appropriate oxidizing agent.
54-1
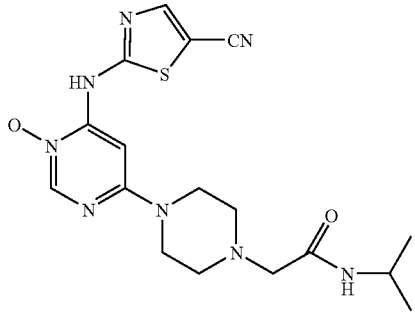
54-2
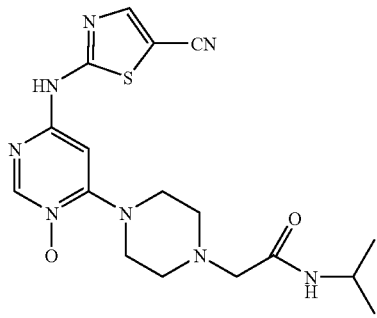
54-3
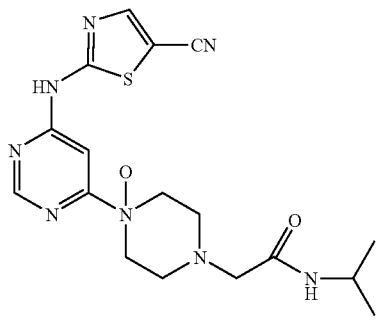
54-4
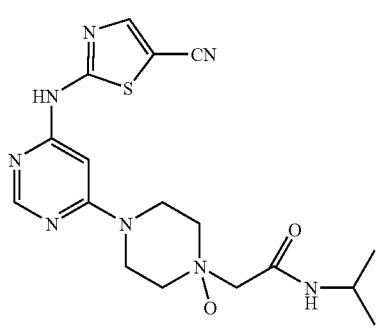
The compounds of Formula A below can also be made by simple modifications of the procedures described above in addition to other procedures known in the art.
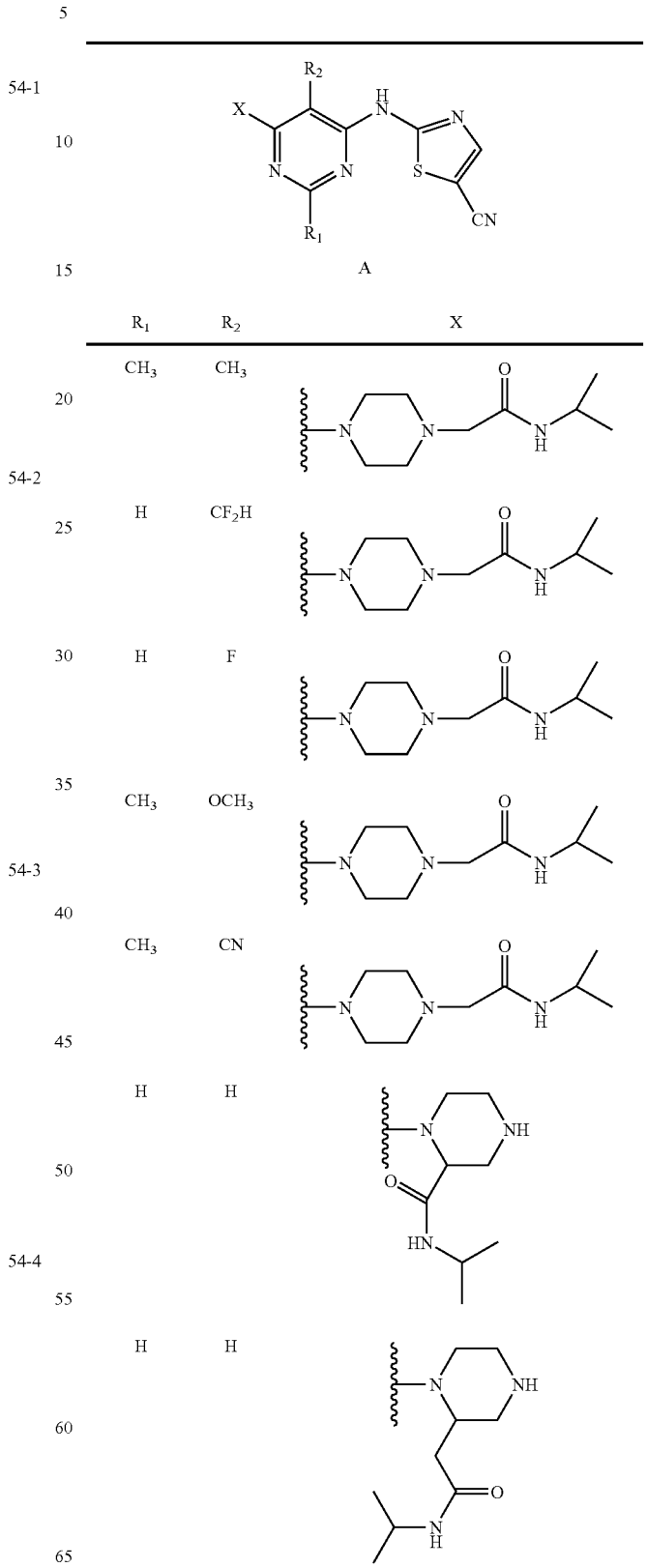

-continued

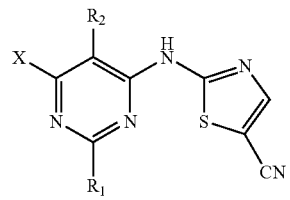

A

| R₁ | R₂ | X |
|---|---|---|
| H | H | piperazine-C(CH₃)₂-C(O)NH-iPr |
| H | H | piperazine N-oxide-CH₂-C(O)NH-iPr |
| H | H | piperidine-4-C(O)NH-iPr |
| H | H | 4-methylpiperidine-4-COOH |
| H | H | 4-methylpiperidine-4-C(O)NH-iPr |
| H | H | 4-methylpiperidine-4-CH₂-C(O)NH-iPr |
| H | H | 4-methylpiperidine-4-CH₂-COOH |
| H | H | 4-amino-piperidine-4-COOH |
| CH₃ | H | azetidine-3-CH₂-C(O)NH-iPr |

-continued

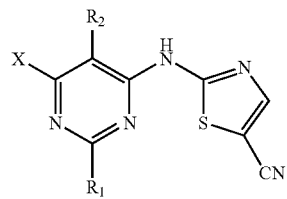

A

| R₁ | R₂ | X |
|---|---|---|
| H | CH₃ | azetidine-3-CH₂-C(O)NH-iPr |
| CH₃ | CH₃ | azetidine-3-CH₂-C(O)NH-iPr |
| H | OCH₃ | azetidine-3-CH₂-C(O)NH-iPr |
| H | CN | azetidine-3-CH₂-C(O)NH-iPr |
| H | C₂H₅ | azetidine-3-CH₂-C(O)NH-iPr |
| H | CF₂H | azetidine-3-CH₂-C(O)NH-iPr |
| H | H | azetidine-3-CH₂-C(O)NH-iPr |
| CH₃ | H | piperazine-(2-oxopiperidin-3-yl) |
| H | CH₃ | piperazine-(2-oxopiperidin-3-yl) |

107

-continued

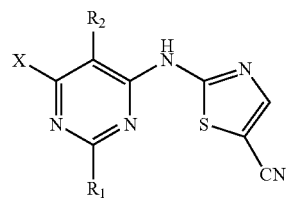

A

| R₁ | R₂ | X |
|---|---|---|
| CH₃ | CH₃ | piperazine-piperidinone |
| H | OCH₃ | piperazine-piperidinone |
| H | CN | piperazine-piperidinone |
| H | C₂H₅ | piperazine-piperidinone |
| H | CF₂H | piperazine-piperidinone |
| H | H | piperazine-piperidinone |
| H | H | piperazine-pyrrolidinone |
| H | H | piperazine-azepanone |
| CH₃ | H | tetrahydrothiophene-3-yl SO₂ |

108

-continued

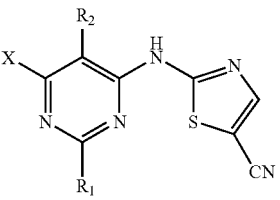

A

| R₁ | R₂ | X |
|---|---|---|
| H | CH₃ | tetrahydrothiophene-3-yl SO₂ |
| CH₃ | CH₃ | tetrahydrothiophene-3-yl SO₂ |
| H | OCH₃ | tetrahydrothiophene-3-yl SO₂ |
| H | CN | tetrahydrothiophene-3-yl SO₂ |
| H | C₂H₅ | tetrahydrothiophene-3-yl SO₂ |
| H | CF₂H | tetrahydrothiophene-3-yl SO₂ |
| CH₃ | H | tetrahydrothiophene-2-yl SO₂ |
| H | CH₃ | tetrahydrothiophene-2-yl SO₂ |
| CH₃ | CH₃ | tetrahydrothiophene-2-yl SO₂ |
| H | OCH₃ | tetrahydrothiophene-2-yl SO₂ |
| H | CN | tetrahydrothiophene-2-yl SO₂ |

-continued

| $R_1$ | $R_2$ | X |
|---|---|---|
| H | $C_2H_5$ | 2-(tetrahydrothiophene-1,1-dioxide)yl |
| H | $CF_2H$ | 2-(tetrahydrothiophene-1,1-dioxide)yl |
| $CH_3$ | H | 3-(thietane-1,1-dioxide)yl |
| H | $CH_3$ | 3-(thietane-1,1-dioxide)yl |
| $CH_3$ | $CH_3$ | 3-(thietane-1,1-dioxide)yl |
| H | $OCH_3$ | 3-(thietane-1,1-dioxide)yl |
| H | CN | 3-(thietane-1,1-dioxide)yl |
| H | $C_2H_5$ | 3-(thietane-1,1-dioxide)yl |
| H | $CF_2H$ | 3-(thietane-1,1-dioxide)yl |

What is claimed is:

1. A compound of Formula I or a pharmaceutically acceptable salt or stereoisomer thereof, wherein A and B are independently N or $N^+$—$O^-$;

Y is O, S or N—$R^4$;

$R^1$ and $R^2$ are independently:
1) H,
2) $O_r(C_1-C_6)$perfluoroalkyl,
3) OH,
4) CN,
5) halogen,
6) (C=O)$_r$O$_s$(C$_1$–C$_{10}$)alkyl,
7) (C=O)$_r$O$_s$(C$_2$–C$_{10}$)alkenyl,
8) (C=O)$_r$O$_s$(C$_2$–C$_{10}$)alkynyl,
9) (C=O)$_r$O$_s$aryl,
10) (C=O)$_r$O$_s$heterocyclyl,
11) (C$_0$–C$_6$)alkyl-NR$^a$R$^b$, or
12) (C$_1$–C$_6$)heterocyclyl, wherein r and s are independently 0 or 1, and said alkyl, alkenyl, alkynyl, aryl, and heterocyclyl is optionally substituted with one or more substituents selected from $R^7$;

$R^4$ is H, aryl or (C$_1$–C$_6$)alkyl;

$R^5$ is:
1) H,
2) SO$_2$R$^c$,
3) (C=O)$_r$R$^c$, wherein r is 0 or 1, or
4) CO$_2$R$^c$;

$R^6$ is:
1) phenyl,
2) CN,
3) halogen, or
4) heterocyclyl, wherein said phenyl and heterocyclyl are optionally substituted with one or more substituents selected from $R^7$;

$R^7$ is:
1) O$_r$(C=O)SNR$^a$R$^b$,
2) (C=O)$_r$O$_s$aryl,
3) (C=O)$_r$O$_s$-heterocyclyl,
4) halogen,
5) OH,
6) oxo,
7) O(C$_1$–C$_3$)perfluoroalkyl,
8) (C$_1$–C$_3$)perfluoroalkyl,
9) (C=O)$_r$O$_s$(C$_1$–C$_6$)alkyl,
10) CHO,
11) CO$_2$H,
12) CN,
13) (C$_1$–C$_6$)alkyl-NR$^a$R$^b$, or
14) (C$_1$–C$_6$)alkyl-heterocyclyl, wherein r and s are independently 0 or 1, and said aryl, heterocyclyl and alkyl are optionally substituted with one to three substituents selected from $R^d$;

$R^a$ and $R^b$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^d$;

$R^c$ is $(C_1–C_6)$alkyl, aryl, or heterocyclyl; and $R^d$ is:
1) $(C=O)_rO_s(C_1–C_{10})$alkyl, wherein r and s are independently 0 or 1, optionally substituted with up to three substituents selected from OH, $(C_1–C_6)$alkoxy, halogen, heterocyclyl, CN, oxo, $N(R^e)_2$ and $S(O)_2R^c$,
2) $O_r(C_1–C_3)$perfluoroalkyl,
3) $(C_0–C_6)$alkylene-$S(O)_mR^c$, wherein m is 0, 1, or 2,
4) oxo,
5) OH,
6) halo,
7) CN,
8) $(C_0–C_6)$alkylene-aryl, optionally substituted with up to three substituents selected from $R^e$,
9) $(C_0–C_6)$alkylene-heterocyclyl, optionally substituted with up to three substituents selected from $R^e$,
10) $C(O)R^c$,
11) $CO_2R^c$,
12) $C(O)H$,
13) $N(R^e)_2$, or
14) $CO_2H$;

$R^e$ is:
1) H,
2) $(C_1–C_6)$alkyl, optionally substituted with one or more substituents selected from OH, heterocyclyl, $(C_1–C_6)$alkoxy, halogen, CN, oxo, $N(R^f)_2$ and $S(O)_2R^c$,
3) aryl, optionally substituted with one or more substituents selected from OH, heterocyclyl, $(C_1–C_6)$alkoxy, halogen, CN, $N(R^f)_2$ and $S(O)_2R^c$,
4) heterocyclyl, optionally substituted with one or more substituents selected from OH, heterocyclyl, $(C_1–C_6)$alkoxy, halogen, CN, oxo, $N(R^f)_2$ and $S(O)_2R^c$, or
6) $S(O)_2R^c$, or
if two $R^e$'s are on a nitrogen atom, they can be taken together with the nitrogen to form a heterocycle with 5–7 atoms, optionally containing, in addition to the nitrogen, one or two additional heteroatoms selected from N, O and S, said heterocycle optionally substituted with one or more substituents selected from OH, $(C_1–C_6)$alkoxy, halogen, CN, oxo, $N(R^f)_2$ and $S(O)_2R^c$; and $R^f$ is H, aryl or $(C_1–C_6)$alkyl.

2. The compound of claim 1, wherein

Y is S;

$R^1$ is H, $(C_1–C_6)$alkyl, or $O(C_1–C_6)$alkyl;

$R^2$ is:
1) H, provided that both $R^1$ and $R^2$ are not H at the same time,
2) $O_r(C_1–C_6)$perfluoroalkyl,
3) OH,
4) CN,
5) halogen,
6) $(C=O)_rO_s(C_1–C_{10})$alkyl,
7) $(C=O)_rO_s(C_2–C_{10})$alkenyl,
8) $(C=O)_rO_s(C_2–C_{10})$alkynyl,
9) $(C=O)_rO_s$aryl,
10) $(C=O)_rO_s$heterocyclyl,
11) $(C_0–C_6)$alkyl-$NR^aR^b$, or
12) $(C_1–C_6)$heterocyclyl,
wherein r and s are independently 0 or 1, and said alkyl, alkenyl, alkynyl, aryl, and heterocyclyl is optionally substituted with one or more substituents selected from $R^7$;

$R^6$ is:
1) phenyl,
2) CN,
3) halogen, or
4) heterocyclyl,
wherein said phenyl and heterocyclyl are optionally substituted with one to three substituents selected from $R^7$;

$R^7$ is:
1) $O_r(C=O)_sNR^aR^b$,
2) $(C=O)_rO_s$aryl,
3) $(C=O)_rO_s$-heterocyclyl,
4) halogen,
5) OH,
6) oxo,
7) $O(C_1–C_3)$perfluoroalkyl,
8) $(C_1–C_3)$perfluoroalkyl,
9) $(C=O)_rO_s(C_1–C_6)$alkyl,
10) CHO,
11) $CO_2H$,
12) CN,
13) $(C_1–C_6)$alkyl-$NR^aR^b$, or
14) $(C_1–C_6)$alkyl-heterocyclyl,
wherein r and s are independently 0 or 1, and said aryl, heterocyclyl and alkyl are optionally substituted with one to three substituents selected from $R^d$;

$R^a$ and $R^b$ are taken together with the nitrogen to which they are attached to form a monocyclic 5–7 membered heterocycle optionally containing, in addition to the nitrogen, one or two additional heteroatoms selected from N, O and S, said heterocycle optionally substituted with one to three substituents selected from $R^d$; and $R^d$ is:
1) $(C=O)_rO_s(C_1–C_6)$alkyl, wherein r and s are independently 0 or 1, optionally substituted with up to three substituents selected from OH, $(C_1–C_6)$alkoxy, halogen, CN, oxo, $N(R^e)_2$ and $S(O)_2R^c$,
2) $O_r(C_1–C_3)$perfluoroalkyl,
3) $(C_0–C_6)$alkylene-$S(O)_mR^c$, wherein m is 0, 1, or 2,
4) oxo,
5) OH,
6) halo,
7) CN,
8) $(C_0–C_6)$alkylene-aryl, optionally substituted with up to three substituents selected from $R^e$,
9) $(C_0–C_6)$alkylene-heterocyclyl, optionally substituted with up to three substituents selected from $R^e$,
10) $(C_0–C_6)$alkylene-$N(R^e)_2$,
11) $C(O)R^c$,
12) $CO_2R^c$,
13) $C(O)H$, or
14) $CO_2H$.

3. The compound of claim 2, wherein A and B are N; and $R^6$ is phenyl, halogen, CN, or pyridyl, said phenyl and pyridyl are optionally substituted with one to three substituents selected from $R^7$.

4. The compound of claim 3 wherein $R^1$ is H and $R^2$ is $O_s(C_1–C_6)$alkyl, wherein s is 0 or 1, optionally substituted with one to three substituents selected from $R^7$, or $(C_0–C_6)$alkyl-$NR^aR^b$.

5. A compound selected from:

2-({6-[4-(2-morpholin-4-ylethyl)piperazin-1-yl]pyrimidin-4-yl}amino)-1,3-thiazole-5-carbonitrile;

2-({6-[4-(2-morpholin-4-yl-2-oxoethyl)piperazin-1-yl]pyrimidin-4-yl}amino)-1,3-thiazole-5-carbonitrile;

N-(tert-butyl)-2-(4-{6-[(5-cyano-1,3-thiazol-2-yl)amino]pyrimidin-4-yl}piperazin-1-yl)acetamide;

2-({6-[4-(1,1-dioxidotetrahydrothien-3-yl)piperazin-1-yl]pyrimidin-4-yl}amino)-1,3-thiazole-5-carbonitrile;

2-(4-{6-[(5-cyano-1,3-thiazol-2-yl)amino]pyrimidin-4-yl}piperazin-1-yl)-N-isopropylacetamide;

2-(1-{6-[(5-cyano-1,3-thiazol-2-yl)amino]pyrimidin-4-yl}piperidin-4-yl)-N-isopropylacetamide; and 2-({6-[4-(2-oxopiperidin-3-yl)piperazin-1-yl]pyrimidin-4-yl}amino)-1,3-thiazole-5-carbonitrile;

or a pharmaceutically acceptable salt or stereoisomer thereof.

6. A compound which is 2-({6-[4-(1,1-dioxidotetrahydrothien-3-yl)piperazin-1-yl]pyrimidin-4-yl}amino)-1,3-thiazole-5-carbonitrile

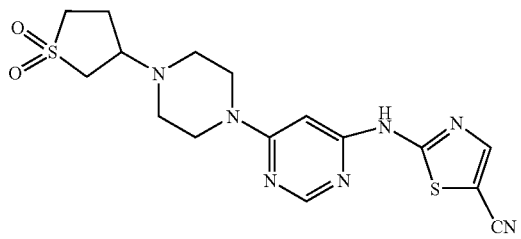

or a pharmaceutically acceptable salt or stereoisomer thereof.

7. A compound which is N-(tert-butyl)-2-(4-{6-[(5-cyano-1,3-thiazol-2-yl)amino]pyrimidin-4-yl}piperazin-1-yl)acetamide

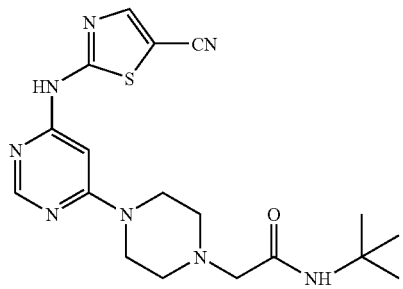

or a pharmaceutically acceptable salt thereof.

8. A compound which is the (R) or (S) enantiomer of 2-({6-[4-(1,1-dioxidotetrahydrothien-3-yl)piperazin-1-yl]pyrimidin-4-yl}amino)-1,3-thiazole-5-carbonitrile in enantiomerically pure form as characterized by an enatiomeric excess of at least 98%, or a pharmaceutically acceptable salt thereof.

9. A compound which is 2-(4-{6-[(5-cyano-1,3-thiazol-2-yl)amino]pyrimidin-4-yl}piperazin-1-yl)-N-isopropylacetamide

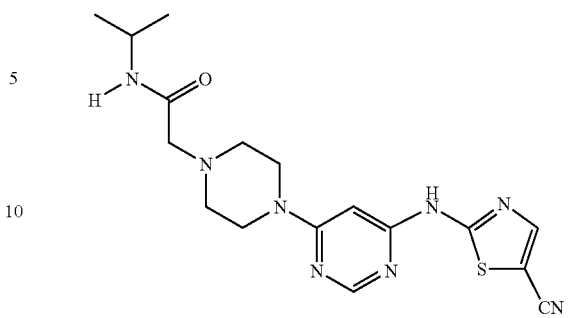

or a pharmaceutically acceptable salt thereof.

10. A pharmaceutical composition which is comprised of a compound in accordance with claim 1 and a pharmaceutically acceptable carrier.

11. A pharmaceutical composition made by combining the compound of claim 1 and a pharmaceutically acceptable carrier.

12. A process for making a pharmaceutical composition which comprises combining a compound of claim 1 with a pharmaceutically acceptable carrier.

13. The composition of claim 10 further comprising a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor,
10) another angiogenesis inhibitor, and
11) a PPAR-γ agonist.

14. The composition of claim 13, wherein the second compound is another angiogenesis inhibitor selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-(chloroacetyl-carbonyl)-fumagillol, thalidomide, angiostatin, troponin-1, and an antibody to VEGF.

15. The composition of claim 13, wherein the second compound is an estrogen receptor modulator selected from tamoxifen and raloxifene.

16. The composition of claim 10 further comprising a steroidal anti-inflammatory compound.

17. The composition of claim 10 further comprising an anti-hypertensive compound.

18. A method of treating cancer in a mammal in need of such treatment which is comprised of administering to said mammal a therapeutically effective amount of a compound of claim 1, wherein said cancer is selected from cancers of the brain, genitourinary tract, lymphatic system, stomach, larynx and lung.

19. A method of treating cancer in a mammal in need of such treatment which is comprised of administering to said mammal a therapeutically effective amount of a compound of claim 1, wherein said cancer is selected from histiocytic lymphoma, lung adenocarcinoma, small cell lung cancers, pancreatic cancer, glioblastomas and breast carcinoma.

20. A method of treating cancer in a mammal in need of such treatment which is comprised of administering to said mammal a therapeutically effective amount of a compound of claim 1, wherein said cancer is selected from colorectal cancer, prostate cancer, breast cancer, and lung cancer.

21. A method of treating a disease in which angiogenesis is implicated, said disease is an ocular disease, which is comprised of administering to a mammal in need of such treatment a therapeutically effective amount of a compound of claim 1.

22. A method of treating retinal vascularization which is comprised of administering to a mammal in need of such treatment a therapeutically effective amount of compound of claim 1.

23. A method of treating diabetic retinopathy which is comprised of administering to a mammal in need of such treatment a therapeutically effective amount of compound of claim 1.

24. The method of claim 21 further comprising the use of photodynamic therapy with a photosensitive drug.

25. The method of claim 24 wherein the photosensitive drug is verteoporfin.

26. A method of treating inflammatory diseases said diseases selected from rheumatoid arthritis, psoriasis, contact dermatitis and delayed hypersensitivity reactions, which comprises administering to a mammal in need of such treatment a therapeutically effective amount of a compound of claim 1.

27. A method of treating bone associated pathologies selected from osteosarcoma, osteoarthritis, and rickets which comprises administering to a mammal in need of such treatment a therapeutically effective amount of a compound of claim 1.

28. A method of reducing tissue damage following a cerebral ischemic event which comprises administering to a mammal in need of such treatment a therapeutically effective amount of a compound of claim 1.

29. A method to treat endometrioses which comprises administering to a mammal in need of such treatment a therapeutically effective amount of a compound of claim 1.

30. A method of treating diabetic retinopathy which comprises administering to a mammal in need of such treatment a therapeutically effective amount of a compound of claim 1 in combination with a PPAR-γ agonist.

31. A method of treating acute myeloid leukemia which comprises administering a therapeutically effective amount of a compound of claim 1.

* * * * *